(12) United States Patent
Buffham et al.

(10) Patent No.: US 9,464,060 B2
(45) Date of Patent: Oct. 11, 2016

(54) COMPOUNDS

(71) Applicant: TAKEDA PHARMACEUTICAL COMPANY LIMITED, Osaka (JP)

(72) Inventors: William Buffham, Cambridge (GB); Hannah Canning, Cambridge (GB); Richard Davenport, Cambridge (GB); William Farnaby, Cambridge (GB); Stephen Mack, Cambridge (GB); Alka Parmar, Cambridge (GB); Susanne Wright, Cambridge (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/463,780

(22) Filed: Aug. 20, 2014

(65) Prior Publication Data

US 2015/0057298 A1    Feb. 26, 2015

(30) Foreign Application Priority Data

Aug. 20, 2013  (GB) .................................. 1314926.5

(51) Int. Cl.
| | | |
|---|---|---|
| *C07D 239/34* | (2006.01) | |
| *C07D 213/78* | (2006.01) | |
| *C07D 213/81* | (2006.01) | |
| *C07C 235/52* | (2006.01) | |
| *C07C 235/46* | (2006.01) | |

(52) U.S. Cl.
CPC ........... *C07D 239/34* (2013.01); *C07C 235/46* (2013.01); *C07C 235/52* (2013.01); *C07D 213/78* (2013.01); *C07D 213/81* (2013.01); *C07C 2101/02* (2013.01); *C07C 2101/04* (2013.01)

(58) Field of Classification Search
None
See application file for complete search history.

(56) References Cited

U.S. PATENT DOCUMENTS

2004/0176446 A1   9/2004  Alonso-Alija et al.

FOREIGN PATENT DOCUMENTS

| EP | 1229034 B1 | 4/2005 |
|---|---|---|
| EP | 1550461 A1 | 7/2005 |
| EP | 1553075 A1 | 7/2005 |
| EP | 2481725 A1 | 8/2012 |

OTHER PUBLICATIONS

Kozian, D. H. et al., "Selective non-lipid modulator of LPA5 activity in human platelets," *Bioorganic & Medicinal Chemistry Letters*, 22, pp. 5239-5243, 2012.
XP-002730136 Database accession No. 1576424-65-5, dated Mar. 28, 2014.
XP-002730137 Database accession No. 1574161-26-4, dated Mar. 26, 2014
XP-002730138 Database accession No. 1571641-85-4, dated Mar. 21, 2014.
XP-002730139 Database accession No. 1568813-80-8, dated Mar. 14, 2014.
XP-002730140 Database accession No. 1573280-07-5, dated Mar. 25, 2014.
U.S. Appl. No. 14/913,135, filed Feb. 19, 2016.
International Search Report and Written Opinion, International Application No. PCT/GB2014/052558, dated Oct. 30, 2014.

*Primary Examiner* — Nyeemah A Grazier
(74) *Attorney, Agent, or Firm* — Finnegan, Henderson, Farabow, Garrett & Dunner LLP.

(57) ABSTRACT

The present invention provides compounds of formula (I) and pharmaceutically acceptable salts thereof,

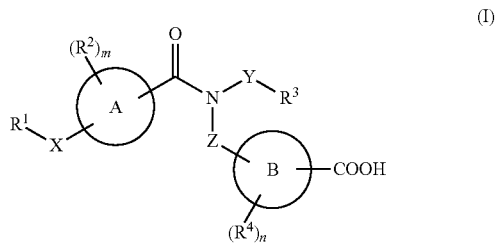

wherein $R^1$, X, m, $R^2$, Y, $R^3$, Z, n, $R^4$, A and B are as defined in the specification, processes for their preparation, pharmaceutical compositions containing them and their use in therapy.

25 Claims, No Drawings

COMPOUNDS

This application claims priority of Great Britain Patent Application No. 1314926.5, filed on 20 Aug. 2013. The contents of this application is incorporated herein by reference.

The present invention relates to amide derivatives, processes for their preparation, pharmaceutical compositions containing them and their use in therapy, particularly as lysophosphatidic acid receptor antagonists.

Lysophosphatidic acid (LPA) is a bioactive lipid mediator that interacts with G protein-coupled transmembrane LPA receptors to affect fundamental cellular functions including proliferation, differentiation, survival, migration, adhesion, invasion and morphogenesis. The effects of LPA at physiological concentrations are mediated by six high affinity cognate LPA receptors (LPA1-6) and potentially at least three additional putative LPA receptors. All known LPA receptors are type 1, rhodopsin-like G protein-coupled receptors (GPCRs) that differ in their tissue distribution and downstream signalling pathways.

LPAR1 was the first high affinity LPA receptor identified. Along with LPAR2 and 3, LPAR1 is one of the Endothelial Differentiation Gene (EDG) LPA receptors. The LPAR1 gene is widely expressed in adult mice, with presence demonstrated in brain, uterus, testis, lung, small intestine, heart, stomach, kidney, spleen, thymus, placenta and skeletal muscle. Expression is also widespread in humans. LPAR1 couples with and activates G$\alpha$i/o, G$\alpha$q/11 and G$\alpha$12/13 G proteins to induce a range of cellular responses. Studies with mice lacking functional LPA1 receptor alleles have implicated LPAR1 in the development of pulmonary fibrosis and neuropathic pain. Intrathecal injection of LPA causes allodynia, hyperalgesia and demyelination of the dorsal root in a LPAR1-dependent manner.

LPAR2 has approximately 60% amino acid homology to LPAR1 and in mouse is expressed in kidney, uterus, testis and lung with lower levels of expression in stomach, spleen, thymus brain and heart. In human tissues high expression is detected in testis and leukocytes and moderate expression in prostate, spleen, thymus and pancreas. LPAR2 couples with G$\alpha$i/o, G$\alpha$q/11 and G$\alpha$12/13 G proteins with signalling associated with processes such as cell survival and cell migration which makes LPAR2 a potential factor for cancer metastasis. In cancer cells, aberrant expression of LPAR2 has been reported, suggesting a tumour promoting role.

Expression of LPAR3 has been seen in human heart, testis, prostate, pancreas, lung, ovary and brain and most abundantly in mouse testis, kidney, lung, small intestine, heart, stomach, spleen, brain and thymus. LPAR3 is able to couple with G$\alpha$i/o, G$\alpha$q/11 to and is also a potential factor for cancer metastasis.

LPA receptors 4, 5 and 6 constitute the non-EDG family of LPA receptors. LPAR4 (P2Y9/GPR23) is more closely related to P2Y purinoreceptors. LPAR4 appears to be broadly expressed in humans with particular abundance in ovary, and is present in mouse heart, skin, thymus and ovary. As with other LPA receptors this GPCR can signal via several pathways, namely G$\alpha$s, G$\alpha$i, G$\alpha$q/11 and G$\alpha$12/13.

Formerly an orphan GPCR, GPR92 was identified at the fifth LPA receptor and renamed LPAR5. Human LPAR5 is located on chromosome 12p13.31 and encodes an approximately 41 kDa protein. LPAR5 is broadly expressed in murine tissues such as small intestine, skin, spleen, stomach, thymus, lung, heart, liver, bladder urothelium, dorsal root ganglion and spinal cord. LPA induces neurite retraction and stress fibre formation in LPAR5-expressing cells through coupling to G$\alpha$12/13 and is also able to activate G$\alpha$s and G$\alpha$q/11. It has been shown that LPAR5 can be activated by ligands other than LPA, namely endogenous by-products of cholesterol synthesis such as farnesyl pyrophosphate (FPP) and N-arachidonylglycine (NAG). Activation of GPR92/LPAR5 by FPP increases inositol phosphate production, cAMP levels, and Ca$^{2+}$ levels in a concentration-dependent manner. There is evidence of a role for LPAR5 in pain since it is highly expressed in and largely co-localized with TRPV1 in mouse and human dorsal root ganglion, as well as the fact that FPP induces calcium influx in DRG neurons in a LPAR5-specific manner. The targeted deletion of LPAR5 in mice produces an analgesic phenotype, with LPAR5 homozygotic mice being less sensitive to touch and pain stimuli in a number of tests and also resistant to development of neuropathic pain. Additionally, LPAR5 knock-out mice display a urological phenotype consistent with changes in sensory signalling. LPA causes aggregation of human platelets at concentrations that are present in atheromatous legions; LPAR5 has been shown to have an intrinsic role in this process.

Most recently, P2Y5 was named as the sixth LPA receptor. This member of the purinergic receptor family is more closely related to LPAR4 and 5 than LPA1-3. This receptor has been identified as a critical mediator of human hair growth.

EP-A-1,553,075 (Ono Pharmaceutical Co., Ltd.) discloses LPA receptor antagonists of general formula

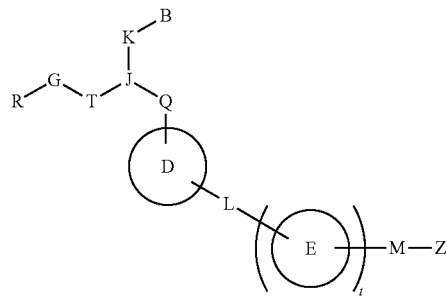

wherein R represents an aliphatic hydrocarbon group which may be substituted, or a cyclic group which may have a substituent(s);

G represents a bond or a spacer having from 1 to 8 atoms in its principle chain;

T represents —CH$_2$—, or a spacer having one atom in its principle chain, the principle chain containing a hydrogen bond acceptable group which may have a substituent(s);

J represents a nitrogen atom or a carbon atom;

B represents an aliphatic hydrocarbon group which may be substituted, or a cyclic group which may have a substituent(s);

K represents (1) a bond, or (2) a spacer having from 1 to 8 atoms in its principle chain which may form a ring together with a substituent of the cyclic group in R, the ring D or a substituent on the ring D;

Q represents (1) a bond, or (2) a spacer having from 1 to 8 atoms in its principle chain which may form a ring together with the cyclic group in R, a substituent of the cyclic group in R or K;

ring D represents a cyclic group which may have an additional substituent(s);

L represents a bond, or a spacer having from 1 to 3 atoms in its principle chain;

ring E represents a cyclic group which may have an additional substituent(s);

M represents a bond, or a spacer having from 1 to 8 atoms in its principle chain;

Z represents an acidic group; and t represents 0 or 1, or a salt thereof.

EP-A-2,481,725 (Astellas Pharma Inc.) discloses LPA receptor antagonists of general formula

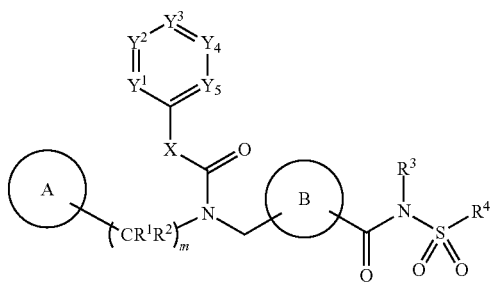

wherein A is an aryl which may be substituted or a hetero ring group which may be substituted, B is a 5-membered aromatic hetero ring group which may be substituted, X is a single bond or —$(CR^{X1}R^{X2})_n$—, n is 1, 2, 3 or 4, $R^{X1}$ and $R^{X2}$ are the same or different from each other, and are H, halogen, OH, —O-(lower alkyl which may be substituted), or lower alkyl which may be substituted, or $R^{X1}$ and $R^{X2}$ are combined with each other to form oxo (=O), or $R^{X1}$ and $R^{X2}$ are combined with each other to form $C_{2-5}$ alkylene which may be substituted, in which when n is 2, 3 or 4, $R^{X1}$ may be combined with adjacent $R^{X1}$ to form a new bond, $Y^1$, $Y^2$, $Y^3$, $Y^4$ and $Y^5$ are the same as or different from each other, and are $CR^Y$ or N, $R^Y$'s are the same as or different from each other, and are H, OH, halogen, —O-(lower alkyl which may be substituted), —S-(lower alkyl which may be substituted), lower alkyl which may be substituted, lower alkenyl which may be substituted, or cycloalkyl which may be substituted, m is 1, 2 or 3, $R^3$ is H, or lower alkyl which may be substituted, $R^4$ is lower alkyl which may be substituted, lower alkenyl which may be substituted, cycloalkyl which may be substituted, aryl which may be substituted, a hetero ring group which may be substituted, or $NR^{101}R^{102}$, or $R^3$ and $R^4$ may be combined with each other to form $C_{2-5}$ alkylene which may be substituted, and $R^{101}$ and $R^{102}$ are the same as or different from each other, and are H, OH, —O-(lower alkyl which may be substituted), —C(=O)-(lower alkyl which may be substituted), —C(=O)—O-(lower alkyl which may be substituted), —NH—C(=O)-(lower alkyl which may be substituted), lower alkyl which may be substituted, lower alkenyl which may be substituted, cycloalkyl which may be substituted, aryl which may be substituted, or a hetero ring group which may be substituted, or $R^{101}$ and $R^{102}$ may be combined with nitrogen atoms to which they are bonded to form a nitrogen-containing monocyclic saturated hetero ring group, in which when $R^4$ is $NR^{101}R^{102}$, at least one of $R^3$, $R^{101}$ and $R^{102}$ is H.

In addition EP-A-1,229,034 describes certain amide derivatives as PDE4 inhibitors for treating respiratory diseases and US 2004/0176446 describes certain amide derivatives for use in treating cardiovascular disorders.

There are currently very few potent LPAR5-selective antagonists. 'LPA5-antagonist 4' has been published by Sanofi-Aventis (Kozian et al, 2012, Bioorg Med Chem Lett., 22(16):5239-43) and is reported to be of low potency against LPAR5 (0.8 µM).

It would be desirable to develop compounds that are potent against LPAR5 and/or LPAR1 for use in treating pain disorders and diseases such as atherosclerosis in which these receptors are believed to play a role.

In accordance with the present invention, there is therefore provided a compound of formula (I)

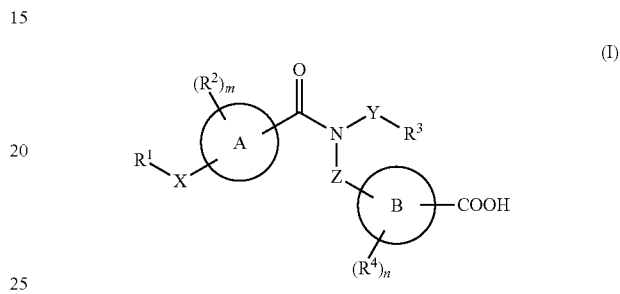

wherein $R^1$ represents a $C_5$-$C_{10}$ aryl group substituted by at least one substituent independently selected from halogen, cyano, nitro, carboxyl, hydroxyl, $C_3$-$C_6$ cycloalkyl, $C_1$-$C_6$ alkoxy, $C_1$-$C_6$ alkoxycarbonyl, $C_1$-$C_6$ alkoxycarbonylamino, $C_1$-$C_6$ haloalkoxy, —$NR^5R^6$, $C_3$-$C_6$ cycloalkylamino, $C_1$-$C_6$ alkylthio, $C_1$-$C_6$ alkylcarbonyl, $C_1$-$C_6$ alkylcarbonyloxy, $C_1$-$C_6$ alkylcarbonylamino, sulphonamido (—$SO_2NH_2$), $C_1$-$C_6$ alkylsulphonyl, $C_1$-$C_6$ alkylsulphonylamino, —$C(O)NR^7R^8$, $C_1$-$C_6$ alkyl which alkyl group may in turn be optionally substituted by at least one halogen, hydroxyl, carboxyl or $C_1$-$C_6$ alkoxycarbonyl group, and a saturated or unsaturated 5- to 6-membered ring which may comprise at least one ring heteroatom independently selected from nitrogen, oxygen and sulphur, the ring itself being optionally substituted by at least one substituent independently selected from halogen, hydroxyl, oxo (=O), carboxyl, cyano, $C_1$-$C_6$ alkyl, $C_1$-$C_6$ alkoxycarbonyl and $C_1$-$C_6$ hydroxyalkyl;

X represents an oxygen atom or a group —$CH_2$—, —$OCH_2$—, —$CH_2O$—, —$CH_2CH_2$—, —$CH_2NR^{17}$—, —$NR^{17}CH_2$—, —CHF— or —$CF_2$—;

m is 0, 1 or 2;

each $R^2$ independently represents a halogen atom or a hydroxyl, $C_1$-$C_6$ alkyl, difluoromethyl, trifluoromethyl, $C_1$-$C_6$ alkoxy, difluoromethoxy, trifluoromethoxy or $NR^{15}R^{16}$ group;

Y represents $CR^9R^{10}$ in which $R^9$ and $R^{10}$ each independently represent a hydrogen atom or a methyl group;

$R^3$ represents $C_1$-$C_8$ alkyl, $C_2$-$C_8$ alkenyl, or a saturated or unsaturated 3- to 10-membered ring system which may comprise at least one ring heteroatom independently selected from nitrogen, oxygen and sulphur, each of the preceding groups being optionally substituted by at least one substituent independently selected from halogen, cyano, hydroxyl. $C_3$-$C_6$ cycloalkyl, $C_1$-$C_6$ alkoxy, $C_5$-$C_6$ aryloxy, $C_5$-$C_6$aryl$C_1$-$C_6$alkyloxy, $C_1$-$C_6$ alkoxycarbonyl, $C_1$-$C_6$ alkoxycarbonylamino, $C_1$-$C_6$ alkoxycarbonyloxy, $C_1$-$C_6$ haloalkyl, $C_1$-$C_6$ haloalkoxy, —$NR^{13}R^{14}$, $C_3$-$C_6$ cycloalkylamino, $C_1$-$C_6$ alkylthio, $C_1$-$C_6$ alkylcarbonyl, $C_1$-$C_6$ alkylcarbonyloxy, $C_1$-$C_6$ alkylcarbonylamino, sulphonamido (—$SO_2NH_2$), $C_1$-$C_6$ alkylsulphonyl, $C_1$-$C_6$ alkylsulphonylamino, $C_1$-$C_6$ alkyl, and a saturated or unsaturated 3- to 10-membered ring system which may comprise at least one ring heteroatom independently selected from nitrogen, oxygen and sulphur, the ring system itself being optionally substituted by least one substituent independently selected from halogen, hydroxyl, oxo (=O), carboxyl, cyano, $C_1$-$C_6$ alkyl. $C_1$-$C_6$ alkoxy. $C_1$-$C_6$ alkoxycarbonyl and $C_1$-$C_6$ hydroxyalkyl;

Z represents $CR^{11}R^{12}$ in which $R^{11}$ and $R^{12}$ each independently represent a hydrogen atom or a methyl group but cannot both simultaneously represent a methyl group;

n is 0, 1 or 2;

each $R^4$ independently represents a halogen atom or a hydroxyl, $C_1$-$C_6$ alkyl, difluoromethyl, trifluoromethyl, $C_1$-$C_6$ alkoxy, difluoromethoxy, trifluoromethoxy or $NR^{18}R^{19}$ group;

$R^5$ and $R^6$ each independently represent a hydrogen atom or a $C_1$-$C_6$ alkyl group, or $R^5$ and $R^6$ together with the nitrogen atom to which they are attached form a 4- to 7-membered saturated heterocycle;

$R^7$ and $R^8$ each independently represent a hydrogen atom or a $C_1$-$C_6$ alkyl group, or $R^7$ and $R^8$ together with the nitrogen atom to which they are attached form a 4- to 7-membered saturated heterocycle;

$R^{13}$ and $R^{14}$ each independently represent a hydrogen atom or a $C_1$-$C_6$ alkyl group, or $R^{13}$ and $R^{14}$ together with the nitrogen atom to which they are attached form a 4- to 7-membered saturated heterocycle;

$R^{15}$ and $R^{16}$ each independently represent a hydrogen atom or a $C_1$-$C_6$ alkyl group, or $R^{15}$ and $R^{16}$ together with the nitrogen atom to which they are attached form a 4- to 7-membered saturated heterocycle;

$R^{17}$ represents a hydrogen atom or a $C_1$-$C_6$ alkyl group;

$R^{18}$ and $R^{19}$ each independently represent a hydrogen atom or a $C_1$-$C_6$ alkyl group, or $R^{18}$ and $R^{19}$ together with the nitrogen atom to which they are attached form a 4- to 7-membered saturated heterocycle; and rings A and B each independently represent a saturated or unsaturated 5- to 10-membered ring system which may comprise at least one ring heteroatom independently selected from nitrogen, oxygen and sulphur;

or a pharmaceutically acceptable salt thereof.

Without being bound to any particular theory, the compounds of the invention have been found to possess dual LPAR5/LPAR1 antagonist properties. Such dual antagonist properties would be expected to be particularly beneficial in the treatment of conditions such as fibrosis.

In the context of the present specification, unless otherwise stated, an "alkyl" or "alkenyl" substituent group or an "alkyl" or "alkenyl" moiety in a substituent group may be linear or branched. Examples of $C_1$-$C_8$ alkyl groups/moieties include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl, n-hexyl, n-heptyl and n-octyl. Examples of $C_2$-$C_8$ alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1-hexadienyl.

A "$C_1$-$C_6$ haloalkyl" or "$C_1$-$C_6$ haloalkoxy" substituent group/moiety will comprise at least one halogen atom, e.g. one, two, three, four or five halogen atoms, examples of which include trifluoromethyl, trifluoromethoxy or pentafluoroethyl.

A "$C_1$-$C_6$ hydroxyalkyl" substituent group/moiety will comprise at least one hydroxyl group, e.g. one, two, three or four hydroxyl groups, examples of which include —$CH_2OH$, —$CH_2CH_2OH$, —$CH_2CH_2CH_2OH$, —$CH(OH)CH_2OH$, —$CH(CH_3)OH$ and —$CH(CH_2OH)_2$.

A "cycloalkyl" substituent group/moiety is a saturated hydrocarbyl ring containing, for example, from 3 to 8 carbon atoms, examples of which include cyclopropyl, cyclobutyl, cyclopentyl and cyclohexyl.

As used herein, "aryl" is intended to mean any stable monocyclic or bicyclic aromatic hydrocarbon system containing up to 10 carbon atoms, e.g. from 5 to 10 carbon atoms, such as phenyl or naphthyl.

In the definition of $R^1$, the saturated or unsaturated 5- to 6-membered ring which may comprise at least one ring heteroatom independently selected from nitrogen, oxygen and sulphur may have alicyclic or aromatic properties. An unsaturated ring will be partially or fully unsaturated. Similar comments apply to the saturated or unsaturated 3- to 10-membered ring systems defined in $R^3$. In either case, it should be understood that the invention does not encompass any unstable ring structures or any O—O, O—S or S—S bonds and that a substituent, if present, may be attached to any suitable ring atom.

When any of $R^5$ and $R^6$, $R^7$ and $R^8$, $R^{13}$ and $R^{14}$, $R^{15}$ and $R^{16}$ or $R^{18}$ and R represents a 4- to 7-membered saturated heterocycle, it should be understood that the heterocycle may contain one or more further heteroatoms (e.g. nitrogen, oxygen or sulphur atoms) in addition to the nitrogen atom to which $R^5$ and $R^6$, $R^7$ and $R^8$, $R^{13}$ and $R^{14}$, $R^{15}$ and $R^{16}$ or $R^{18}$ and $R^{19}$ are attached.

When any chemical moiety or group in formula (I) is described as being optionally substituted, it will be appreciated that the moiety or group may be either unsubstituted or substituted by one or more of the specified substituents. It will be appreciated that the number and nature of substituents will be selected so as to avoid sterically undesirable combinations.

$R^1$ represents a $C_5$-$C_{10}$ or $C_5$-$C_6$ aryl group substituted by at least one substituent, e.g. one, two, three or four substituents, independently selected from
(i) halogen (e.g. fluorine, chlorine, bromine or iodine),
(ii) cyano,
(iii) nitro,
(iv) carboxyl,
(v) hydroxyl,
(vi) $C_3$-$C_6$ or $C_5$-$C_6$ cycloalkyl,
(vii) $C_1$-$C_6$, or $C_1$-$C_4$, or $C_1$-$C_2$ alkoxy,
(viii) $C_1$-$C_6$, or $C_1$-$C_4$, or $C_1$-$C_2$ alkoxycarbonyl,
(ix) $C_1$-$C_6$, or $C_1$-$C_4$, or $C_1$-$C_2$ alkoxycarbonylamino,
(x) $C_1$-$C_6$, or $C_1$-$C_4$, or $C_1$-$C_2$ haloalkoxy,
(xi) —$NR^5R^6$,
(xii) $C_3$-$C_6$ or $C_5$-$C_6$ cycloalkylamino,
(xiii) $C_1$-$C_6$, or $C_1$-$C_4$, or $C_1$-$C_2$ alkylthio,
(xiv) $C_1$-$C_6$, or $C_1$-$C_4$, or $C_1$-$C_2$ alkylcarbonyl,
(xv) $C_1$-$C_6$, or $C_1$-$C_4$, or $C_1$-$C_2$ alkylcarbonyloxy,
(xvi) $C_1$-$C_6$, or $C_1$-$C_4$, or $C_1$-$C_2$ alkylcarbonylamino,
(xvii) sulphonamido,
(xviii) $C_1$-$C_6$, or $C_1$-$C_4$, or $C_1$-$C_2$ alkylsulphonyl,
(xix) $C_1$-$C_6$, or $C_1$-$C_4$, or $C_1$-$C_2$ alkylsulphonylamino,
(xx) —$C(O)NR^7R^8$, (xxi) $C_1$-$C_6$, or $C_1$-$C_4$, or $C_1$-$C_2$ alkyl which alkyl group may in turn be optionally substituted by at least one substituent, e.g. one, two, three or four substituents, independently selected from halogen (e.g. fluorine, chlorine, bromine or iodine), hydroxyl, carboxyl and $C_1$-$C_6$, or $C_1$-$C_4$, or $C_1$-$C_2$ alkoxycarbonyl, and (xxii) a saturated or unsaturated 5- to 6-membered ring which may comprise at least one ring heteroatom, e.g one, two, three or four ring heteroatoms, independently selected from nitrogen, oxygen and sulphur (preferably nitrogen or oxygen), the ring itself being optionally substituted by at least one substituent, e.g. one, two, three or four substituents, independently selected from halogen (e.g. fluorine, chlorine, bromine or iodine), hydroxyl, oxo, carboxyl, cyano, $C_1$-$C_6$, or $C_1$-$C_4$, or $C_1$-$C_2$ alkyl, $C_1$-$C_6$, or $C_1$-$C_4$, or $C_1$-$C_2$ alkoxycarbonyl and $C_1$-$C_6$, or $C_1$-$C_4$, or $C_1$-$C_2$ hydroxyalkyl. Examples of saturated or unsaturated 5- to 6-membered rings include hydrocarbyl rings such as phenyl and heterocyclic rings such as pyrrolidinyl, piperidinyl, morpholinyl, tetrahydropyranyl, oxadiazolyl, pyrrolyl, imidazolyl, pyridinyl, pyrazinyl, pyridazinyl, pyrimidinyl, thienyl and furanyl.

The at least one substituent in $R^1$ is preferably attached in an ortho position relative to the point of attachment of $R^1$ to X. For example, if $R^1$ is phenyl, then the preferred carbon atoms to which a substituent is attached are shown by the asterisks in the structure below:

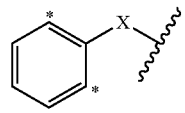

In an embodiment of the invention, $R^1$ represents a $C_5$-$C_6$ aryl (preferably phenyl) group substituted by at least one substituent, e.g. one, two, three or four substituents, independently selected from
  (i) halogen (e.g. fluorine, chlorine, bromine or iodine),
  (ii) cyano,
  (iii) nitro,
  (iv) carboxyl,
  (v) hydroxyl,
  (vi) $C_1$-$C_6$, or $C_1$-$C_4$, or $C_1$-$C_2$ alkoxy,
  (vii) $C_1$-$C_6$, or $C_1$-$C_4$, or $C_1$-$C_2$ alkoxycarbonyl,
  (viii) $C_1$-$C_6$, or $C_1$-$C_4$, or $C_1$-$C_2$ alkoxycarbonylamino,
  (ix) $C_1$-$C_6$, or $C_1$-$C_4$, or $C_1$-$C_2$ haloalkoxy,
  (x) —$NR^5R^6$,
  (xi) $C_3$-$C_6$ or $C_5$-$C_6$ cycloalkylamino,
  (xii) $C_1$-$C_6$, or $C_1$-$C_4$, or $C_1$-$C_2$ alkylthio,
  (xiii) $C_1$-$C_6$, or $C_1$-$C_4$, or $C_1$-$C_2$ alkylcarbonyl,
  (xiv) $C_1$-$C_6$, or $C_1$-$C_4$, or $C_1$-$C_2$ alkylcarbonyloxy,
  (xv) $C_1$-$C_6$, or $C_1$-$C_4$, or $C_1$-$C_2$ alkylcarbonylamino,
  (xvi) $C_1$-$C_6$, or $C_1$-$C_4$, or $C_1$-$C_2$ alkylsulphonyl,
  (xvii) $C_1$-$C_6$, or $C_1$-$C_4$, or $C_1$-$C_2$ alkylsulphonylamino,
  (xviii) —$C(O)NR^7R^8$,
  (xix) $C_1$-$C_6$, or $C_1$-$C_4$, or $C_1$-$C_2$ alkyl which alkyl group may in turn be optionally substituted by at least one substituent, e.g. one, two, three or four substituents, independently selected from halogen (e.g. fluorine, chlorine, bromine or iodine), hydroxyl, carboxyl and $C_1$-$C_6$, or $C_1$-$C_4$, or $C_1$-$C_2$ alkoxycarbonyl, and
  (xx) a saturated or unsaturated 5- to 6-membered ring which may comprise at least one ring heteroatom, e.g one, two, three or four ring heteroatoms, independently selected from nitrogen, oxygen and sulphur (preferably nitrogen or oxygen), the ring itself being optionally substituted by at least one substituent, e.g. one, two, three or four substituents, independently selected from halogen (e.g. fluorine, chlorine, bromine or iodine), hydroxyl, oxo, carboxyl, cyano, $C_1$-$C_6$, or $C_1$-$C_4$, or $C_1$-$C_2$ alkyl, $C_1$-$C_6$, or $C_1$-$C_4$, or $C_1$-$C_2$ alkoxycarbonyl and $C_1$-$C_6$, or $C_1$-$C_4$, or $C_1$-$C_2$ hydroxyalkyl.

In another embodiment of the invention, $R^1$ represents a $C_5$-$C_6$ aryl group substituted by one or two substituents independently selected from
  (i) halogen (e.g. fluorine, chlorine, bromine or iodine),
  (ii) cyano,
  (iii) nitro,
  (iv) carboxyl,
  (v) hydroxyl,
  (vi) $C_1$-$C_2$ alkoxy,
  (vii) $C_1$-$C_2$ alkoxycarbonyl,
  (viii) $C_1$-$C_2$ alkoxycarbonylamino,
  (ix) $C_1$-$C_2$ haloalkoxy,
  (x) —$NR^5R^6$,
  (xi) $C_5$-$C_6$ cycloalkylamino,
  (xii) $C_1$-$C_2$ alkylthio,
  (xiii) $C_1$-$C_2$ alkylcarbonyl,
  (xiv) $C_1$-$C_2$ alkylcarbonyloxy,
  (xv) $C_1$-$C_2$ alkylcarbonylamino,
  (xvi) $C_1$-$C_2$ alkylsulphonyl,
  (xvii) $C_1$-$C_2$ alkylsulphonylamino,
  (xviii) —$C(O)NR^7R^8$,
  (xix) $C_1$-$C_2$ alkyl which alkyl group may in turn be optionally substituted by at least one halogen atom, preferably from 1 to 3 halogen atoms (particularly fluorine atoms), and
  (xx) a saturated or unsaturated 5- to 6-membered ring which may comprise at least one ring heteroatom, e.g one, two, three or four ring heteroatoms, independently selected from nitrogen, oxygen and sulphur (preferably nitrogen or oxygen), the ring itself being optionally substituted by at least one substituent, e.g. one, two, three or four substituents, independently selected from halogen (e.g. fluorine, chlorine, bromine or iodine), hydroxyl, oxo, carboxyl, cyano, $C_1$-$C_2$ alkyl, $C_1$-$C_2$ alkoxycarbonyl and $C_1$-$C_2$ hydroxyalkyl.

In still another embodiment of the invention, $R^1$ represents a phenyl group substituted by one or two substituents independently selected from
  (i) halogen (e.g. fluorine or chlorine),
  (ii) cyano,
  (iii) $C_1$-$C_2$ alkoxy (particularly methoxy), and
  (iv) $C_1$-$C_2$ alkyl which alkyl group may in turn be optionally substituted by at least one halogen atom, preferably from 1 to 3 halogen atoms (particularly fluorine atoms).

In yet another embodiment, $R^1$ represents fluorophenyl (in particular 2-fluorophenyl), chlorophenyl (in particular 2-chlorophenyl or 3-chlorophenyl), difluorophenyl (in particular 2,6-difluorophenyl), chlorofluorophenyl (in particular 2-chloro-6-fluorophenyl), fluoromethylphenyl (in particular 2-fluoro-6-methylphenyl), methylphenyl (in particular 2-methylphenyl), dimethylphenyl (in particular 2,6-dimethylphenyl), cyanophenyl (in particular 2-cyanophenyl), trifluoromethylphenyl (in particular 2-trifluoromethylphenyl), methoxyphenyl (e.g. 2-methoxyphenyl, 3-methoxyphenyl or 4-methoxyphenyl), ethoxyphenyl (in particular 2-ethoxyphenyl), 2-fluoro-6-methoxyphenyl, 3-fluoro-2-methoxyphenyl, 4-fluoro-2-methoxyphenyl or 5-fluoro-2-methoxyphenyl.

In an embodiment of the invention, X represents an oxygen atom or a group —CH$_2$—, —OCH$_2$— or —CH$_2$O—.

In another embodiment, X represents an oxygen atom or —CH$_2$O— (where it will be understood that the oxygen atom is attached to the ring A in formula (I)).

In yet another embodiment, X represents an oxygen atom.

In a further embodiment, X represents —CH$_2$O—.

In a still further embodiment, X represents —CH$_2$NR$^{17}$—, in particular —CH$_2$NH—.

When m is 1 or 2, each R$^2$ independently represents a halogen atom (e.g. fluorine, chlorine, bromine or iodine) or a hydroxyl, C$_1$-C$_6$, or C$_1$-C$_4$, or C$_1$-C$_2$ alkyl, difluoromethyl, trifluoromethyl, C$_1$-C$_6$, or C$_1$-C$_4$, or C$_1$-C$_2$ alkoxy, difluoromethoxy, trifluoromethoxy or NR$^{15}$R$^{16}$ group. Preferably, R$^2$ represents a halogen atom (particularly fluorine) or a C$_1$-C$_6$, or C$_1$-C$_4$, or C$_1$-C$_2$ alkyl (particularly methyl) group.

In one embodiment of the invention, m is 1 and R$^2$ represents a halogen atom (particularly fluorine).

In a further embodiment, m is 2 and each R$^2$ independently represents a C$_1$-C$_6$, or C$_1$-C$_4$, or C$_1$-C$_2$ alkyl (particularly methyl) group.

In a still further embodiment, m is 0 and the ring A has no R$^2$ substituents.

In one aspect, Y represents CH$_2$ or CH(CH$_3$), preferably CH$_2$.

R$^3$ represents C$_1$-C$_8$, or C$_1$-C$_6$, or C$_1$-C$_4$, or C$_1$-C$_2$ alkyl, C$_2$-C$_8$, or C$_2$-C$_6$, or C$_2$-C$_4$ alkenyl, or a saturated or unsaturated 3- to 10-membered (e.g. 3-, 4-, 5- or 6- to 7-, 8-, 9- or 10-membered) ring system which may comprise at least one ring heteroatom (e.g. one, two, three or four ring heteroatoms) independently selected from nitrogen, oxygen and sulphur, each of the preceding groups being optionally substituted by at least one substituent (e.g. one, two, three or four substituents) independently selected from
(i) halogen (e.g. fluorine, chlorine, bromine or iodine),
(ii) cyano,
(iii) hydroxyl,
(iv) C$_3$-C$_6$ or C$_5$-C$_6$ cycloalkyl,
(v) C$_1$-C$_6$, or C$_1$-C$_4$, or C$_1$-C$_2$ alkoxy,
(vi) C$_5$-C$_6$ aryloxy,
(vii) C$_5$-C$_6$arylC$_1$-C$_6$, or C$_1$-C$_4$, or C$_1$-C$_2$ alkyloxy,
(viii) C$_1$-C$_6$, or C$_1$-C$_4$, or C$_1$-C$_2$ alkoxycarbonyl,
(ix) C$_1$-C$_6$, or C$_1$-C$_4$, or C$_1$-C$_2$ alkoxycarbonylamino,
(x) C$_1$-C$_6$, or C$_1$-C$_4$, or C$_1$-C$_2$ alkoxycarbonyloxy,
(xi) C$_1$-C$_6$, or C$_1$-C$_4$, or C$_1$-C$_2$ haloalkyl,
(xii) C$_1$-C$_6$, or C$_1$-C$_4$, or C$_1$-C$_2$ haloalkoxy,
(xiii) —NR$^{13}$R$^{14}$
(xiv) C$_3$-C$_6$ or C$_5$-C$_6$ cycloalkylamino,
(xv) C$_1$-C$_6$, or C$_1$-C$_4$, or C$_1$-C$_2$ alkylthio,
(xvi) C$_1$-C$_6$, or C$_1$-C$_4$, or C$_1$-C$_2$ alkylcarbonyl,
(xvii) C$_1$-C$_6$, or C$_1$-C$_4$, or C$_1$-C$_2$ alkylcarbonyloxy,
(xviii) C$_1$-C$_6$, or C$_1$-C$_4$, or C$_1$-C$_2$ alkylcarbonylamino,
(xix) sulphonamido,
(xx) C$_1$-C$_6$, or C$_1$-C$_4$, or C$_1$-C$_2$ alkylsulphonyl,
(xxi) C$_1$-C$_6$, or C$_1$-C$_4$, or C$_1$-C$_2$ alkylsulphonylamino,
(xxii) C$_1$-C$_6$, or C$_1$-C$_4$, or C$_1$-C$_2$ alkyl, and
(xxiii) a saturated or unsaturated 3- to 10-membered (e.g. 3-, 4-, 5- or 6- to 7-, 8-, 9- or 10-membered) ring system which may comprise at least one ring heteroatom (e.g. one, two, three or four ring heteroatoms) independently selected from nitrogen, oxygen and sulphur, the ring system itself being optionally substituted by least one substituent (e.g. one, two, three or four substituents) independently selected from halogen (e.g. fluorine, chlorine, bromine or iodine), hydroxyl, oxo, carboxyl, cyano, C$_1$-C$_6$, or C$_1$-C$_4$, or C$_1$-C$_2$ alkyl, C$_1$-C$_6$, or C$_1$-C$_4$, or C$_1$-C$_2$ alkoxy, C$_1$-C$_6$, or C$_1$-C$_4$, or C$_1$-C$_2$ alkoxycarbonyl and C$_1$-C$_6$, or C$_1$-C$_4$, or C$_1$-C$_2$ hydroxyalkyl.

Examples of saturated or unsaturated 3- to 10-membered ring systems that may be used, which may be monocyclic or polycyclic (e.g. bicyclic) in which the two or more rings may be fused, bridged or spiro include one or more (in any combination) of cyclopropyl, cyclobutyl, cyclopentyl, cyclohexyl, bicyclo[2.2.1]heptyl, cyclopentenyl, cyclohexenyl, phenyl, pyrrolidinyl, piperidinyl, piperazinyl, morpholinyl, thiomorpholinyl, oxadiazolyl (e.g. 1,2,4-oxadiazolyl), tetrahydrofuranyl, diazabicyclo[2.2.1]hept-2-yl, naphthyl, benzofuranyl, benzothienyl, benzodioxolyl, benzoxazolyl, quinolinyl, oxazolyl, thiadiazolyl (e.g. 1,2,3-thiadiazolyl), 2,3-dihydrobenzofuranyl, tetrahydropyranyl, pyrazolyl, imidazo[1,2-a]pyridinyl, pyrazinyl, thiazolidinyl, indanyl, thienyl, isoxazolyl, pyridazinyl, pyrrolyl, furanyl, thiazolyl, isothiazolyl, indolyl, isoindolyl, imidazolyl, pyrimidinyl, benzimidazolyl, triazolyl, tetrazolyl and pyridinyl.

Preferred ring systems include phenyl, cyclopropyl, cyclobutyl, cyclopentyl, cyclohexyl and thienyl.

In one aspect of the invention, R$^3$ represents C$_1$-C$_4$, or C$_1$-C$_3$, or C$_1$-C$_2$ alkyl, C$_2$-C$_4$ alkenyl, or a saturated or unsaturated 3-, 4-, 5- or 6-membered ring system which may comprise at least one ring heteroatom (e.g. one, two, three or four ring heteroatoms) independently selected from nitrogen, oxygen and sulphur, each of the preceding groups being optionally substituted by at least one substituent (e.g. one, two, three or four substituents) independently selected from
(i) halogen (e.g. fluorine, chlorine, bromine or iodine),
(ii) cyano,
(iii) hydroxyl,
(iv) C$_3$-C$_6$ or C$_5$-C$_6$ cycloalkyl,
(v) C$_1$-C$_2$ alkoxy,
(vi) C$_5$-C$_6$ aryloxy,
(vii) C$_5$-C$_6$arylC$_1$-C$_2$ alkyloxy,
(viii) C$_1$-C$_2$ alkoxycarbonyl,
(ix) C$_1$-C$_2$ alkoxycarbonylamino,
(x) C$_1$-C$_2$ alkoxycarbonyloxy,
(xi) C$_1$-C$_2$ haloalkyl,
(xii) C$_1$-C$_2$ haloalkoxy,
(xiii) —NR$^{13}$R$^{14}$
(xiv) C$_3$-C$_6$ or C$_5$-C$_6$ cycloalkylamino,
(xv) C$_1$-C$_2$ alkylthio,
(xvi) C$_1$-C$_2$ alkylcarbonyl,
(xvii) C$_1$-C$_2$ alkylcarbonyloxy,
(xviii) C$_1$-C$_2$ alkylcarbonylamino,
(xix) sulphonamido,
(xx) C$_1$-C$_2$ alkylsulphonyl,
(xxi) C$_1$-C$_2$ alkylsulphonylamino,
(xxii) C$_1$-C$_2$ alkyl, and
(xxiii) a saturated or unsaturated 3-, 4-, 5- or 6-membered ring system which may comprise at least one ring heteroatom (e.g. one, two, three or four ring heteroatoms) independently selected from nitrogen, oxygen and sulphur, the ring system itself being optionally substituted by least one substituent (e.g. one, two, three or four substituents) independently selected from halogen (e.g. fluorine, chlorine, bromine or iodine), hydroxyl, oxo, carboxyl, cyano, C$_1$-C$_2$ alkyl, C$_1$-C$_2$ alkoxy, C$_1$-C$_2$ alkoxycarbonyl and C$_1$-C$_2$ hydroxyalkyl.

In a further aspect of the invention, R$^3$ represents C$_1$-C$_4$, or C$_1$-C$_3$, or C$_1$-C$_2$ alkyl, C$_2$-C$_4$ alkenyl, or a saturated or unsaturated 3-, 4-, 5- or 6-membered hydrocarbyl ring system (e.g. cyclopropyl, cyclobutyl, cyclopentyl, cyclohexyl or phenyl), each of the preceding groups being optionally substituted by at least one substituent (e.g. one, two, three or four substituents) independently selected from
(i) halogen (e.g. fluorine or chlorine),
(ii) hydroxyl,
(iii) $C_3$-$C_6$ cycloalkyl,
(iv) $C_1$-$C_2$ alkoxy,
(v) $C_5$-$C_6$ aryloxy,
(vi) $C_5$-$C_6$aryl$C_1$-$C_2$ alkyloxy,
(vii) $C_1$-$C_2$ haloalkyl,
(viii) $C_1$-$C_2$ alkyl, and
(ix) a saturated or unsaturated 3-, 4-, 5- or 6-membered ring system which may comprise at least one ring heteroatom (e.g. one or two ring heteroatoms) independently selected from nitrogen, oxygen and sulphur (e.g. cyclopropyl, cyclobutyl, cyclopentyl, cyclohexyl, phenyl and thienyl), the ring system itself being optionally substituted by least one substituent (e.g. one, two, three or four substituents) independently selected from halogen (e.g. fluorine or chlorine), $C_1$-$C_2$ alkyl and $C_1$-$C_2$ alkoxy.

In a still further aspect, $R^3$ represents $C_1$-$C_4$, or $C_1$-$C_3$, or $C_1$-$C_2$ alkyl, or a saturated or unsaturated 3-, 4-, 5- or 6-membered hydrocarbyl ring system (e.g. cyclopropyl, cyclobutyl, cyclopentyl, cyclohexyl or phenyl), each of the preceding groups being optionally substituted by at least one substituent (e.g. one, two, three or four substituents) independently selected from
(i) fluorine
(ii) chlorine,
(iii) hydroxyl,
(iv) $C_3$-$C_6$ cycloalkyl,
(v) $C_1$-$C_2$ alkoxy,
(vi) phenoxy,
(vii) benzyloxy,
(viii) trifluoromethyl,
(ix) $C_1$-$C_2$ alkyl, and
(x) a saturated or unsaturated 3-, 4-, 5- or 6-membered ring system which may comprise at least one ring heteroatom (e.g. one or two ring heteroatoms) independently selected from nitrogen, oxygen and sulphur (e.g. cyclopropyl, cyclobutyl, cyclopentyl, cyclohexyl, phenyl and thienyl), the ring system itself being optionally substituted by least one substituent (e.g. one, two, three or four substituents) independently selected from halogen (e.g. fluorine or chlorine), $C_1$-$C_2$ alkyl and $C_1$-$C_2$ alkoxy.

In still another aspect, $R^3$ represents $C_1$-$C_4$, or $C_1$-$C_3$, or $C_1$-$C_2$ alkyl, cyclopropyl, cyclobutyl or phenyl, each of the preceding groups being optionally substituted by at least one substituent (e.g. one, two, three or four substituents) independently selected from
(i) fluorine,
(ii) hydroxyl,
(iii) methoxy,
(iv) cyclopropyl,
(v) cyclobutyl, and
(vi) phenyl optionally substituted by least one halogen (e.g. fluorine or chlorine) atom.

In a particular embodiment of the invention, $R^3$ represents any one of the following moieties or is selected from a group containing any two or more of such moieties:
(i) methyl,
(ii) difluoromethyl,
(iii) trifluoromethyl,
(iv) ethyl,
(v) difluoroethyl (e.g. 1,1-difluoroethyl),
(vi) trifluoroethyl (e.g. 2,2,2,-trifluoroethyl),
(vii) —$CH_2CH_2CH_3$
(ix) —$CH_2CH(CH_3)_2$,
(x) cyclopropyl,
(xi) cyclopropylmethyl,
(xii) cyclobutyl,
(xiii) cyclobutylmethyl,
(xiv) 3-methoxycyclobutyl,
(xv) phenyl,
(xvi) 2-fluorophenyl,
(xvii) 3-methoxyphenyl,
(xviii) 4-methoxyphenyl,
(xix) benzyl,
(xx) phenylethyl,
(xxi) (2-fluorophenyl)ethyl,
(xxii) (3-fluorophenyl)ethyl,
(xxiii) phenylpropyl,
(xxiv) phenylcyclopropyl,
(xxv) —$CH(OH)CH_2$-phenyl.

Z represents $CH_2$ or $CH(CH_3)$, preferably $CH_2$.

When n is 1 or 2, each $R^4$ independently represents a halogen atom (e.g. fluorine, chlorine, bromine or iodine) or a hydroxyl, $C_1$-$C_6$, or $C_1$-$C_4$, or $C_1$-$C_2$ alkyl, difluoromethyl, trifluoromethyl, $C_1$-$C_6$, or $C_1$-$C_4$, or $C_1$-$C_2$ alkoxy, difluoromethoxy, trifluoromethoxy or $NR^{18}R^{19}$ group.

In one embodiment, n is 1 and $R^4$ represents a halogen atom (particularly fluorine) or a $C_1$-$C_6$, or $C_1$-$C_4$, or $C_1$-$C_2$ alkyl (particularly methyl) or a $C_1$-$C_6$, or $C_1$-$C_4$, or $C_1$-$C_2$ alkoxy (particularly methoxy) group.

In another embodiment, n is 0 and the ring B has no $R^4$ substituents.

$R^5$ and $R^6$ each independently represent a hydrogen atom or a $C_1$-$C_6$, or $C_1$-$C_4$, or $C_1$-$C_2$ alkyl group, or $R^5$ and $R^6$ together with the nitrogen atom to which they are attached form a 4- to 7-membered saturated heterocycle (e.g. pyrrolidinyl, morpholinyl, piperazinyl or piperidinyl).

$R^7$ and $R^8$ each independently represent a hydrogen atom or a $C_1$-$C_6$, or $C_1$-$C_4$, or $C_1$-$C_2$ alkyl group, or $R^7$ and $R^8$ together with the nitrogen atom to which they are attached form a 4- to 7-membered saturated heterocycle (e.g. pyrrolidinyl, morpholinyl, piperazinyl or piperidinyl).

$R^{13}$ and $R^{14}$ each independently represent a hydrogen atom or a $C_1$-$C_6$, or $C_1$-$C_4$, or $C_1$-$C_2$ alkyl group, or $R^{13}$ and $R^{14}$ together with the nitrogen atom to which they are attached form a 4- to 7-membered saturated heterocycle (e.g. pyrrolidinyl, morpholinyl, piperazinyl or piperidinyl).

$R^{15}$ and $R^{16}$ each independently represent a hydrogen atom or a $C_1$-$C_6$, or $C_1$-$C_4$, or $C_1$-$C_2$ alkyl group, or $R^{15}$ and $R^{16}$ together with the nitrogen atom to which they are attached form a 4- to 7-membered saturated heterocycle (e.g. pyrrolidinyl, morpholinyl, piperazinyl or piperidinyl).

$R^{17}$ represents a hydrogen atom or a $C_1$-$C_6$, or $C_1$-$C_4$, or $C_1$-$C_2$ alkyl (particularly methyl or ethyl) group, especially a hydrogen atom.

$R^{18}$ and $R^{19}$ each independently represent a hydrogen atom or a $C_1$-$C_6$, or $C_1$-$C_4$, or $C_1$-$C_2$ alkyl group, or $R^{18}$ and $R^{19}$ together with the nitrogen atom to which they are attached form a 4- to 7-membered saturated heterocycle (e.g. pyrrolidinyl, morpholinyl, piperazinyl or piperidinyl).

Rings A and B each independently represent a saturated or unsaturated 5-, 6-, 7-, 8-, 9- or 10-membered ring system which may comprise at least one ring heteroatom (e.g. one, two, three or four heteroatoms) independently selected from nitrogen, oxygen and sulphur.

Examples of saturated or unsaturated 5- to 10-membered ring systems that may be used, which may be monocyclic or polycyclic (e.g. bicyclic) in which the two or more rings are fused include one or more (in any combination) of cyclopentyl, cyclohexyl, cyclopentenyl, cyclohexenyl, phenyl, pyrrolidinyl, piperidinyl, piperazinyl, morpholinyl, thiomorpholinyl, oxadiazolyl (e.g. 1,2,4-oxadiazolyl), tetrahydrofuranyl, naphthyl, benzofuranyl, benzothienyl, benzodioxolyl, benzoxazolyl, quinolinyl, oxazolyl, thiadiazolyl (e.g. 1,2,3-thiadiazolyl), 2,3-dihydrobenzofuranyl, tetrahydropyranyl, pyrazolyl, imidazo[1,2-a]pyridinyl, pyrazinyl, thiazolidinyl, indanyl, thienyl, isoxazolyl, pyridazinyl, pyrrolyl, furanyl, thiazolyl, isothiazolyl, indolyl, isoindolyl, imidazolyl, pyrimidinyl, benzimidazolyl, triazolyl, tetrazolyl and pyridinyl. Preferred ring systems include 5- or 6-membered ring systems such as phenyl, pyridinyl, pyrimidinyl, thienyl and cyclohexyl.

In an embodiment of the invention, ring A is selected from phenyl, pyridinyl, pyrimidinyl, thienyl and cyclohexyl. Examples of ring A showing the points of attachment of $R^1$—X—, $R^2$ and C(O) to the ring are shown below:

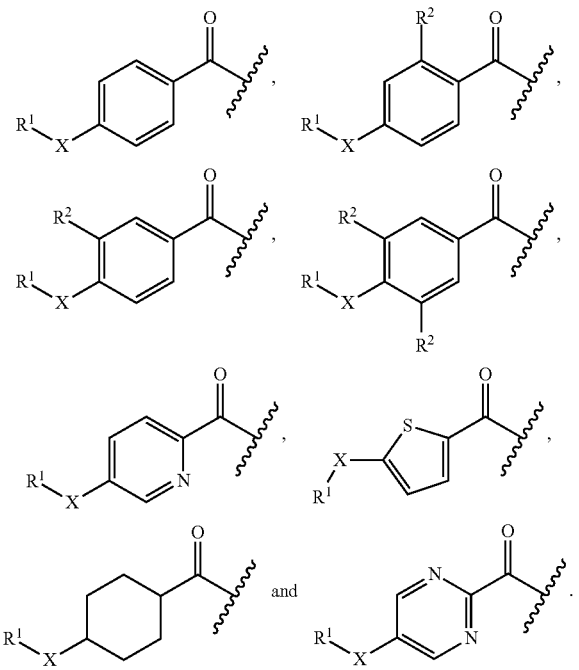

In another embodiment of the invention, ring B is selected from phenyl, thienyl and cyclohexyl. Examples of ring B showing the points of attachment of Z, $R^4$ and C(O)OH to the ring are shown below:

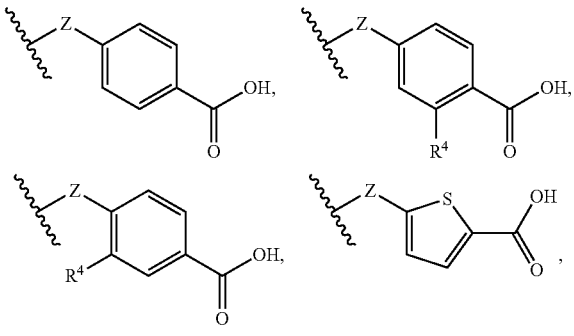

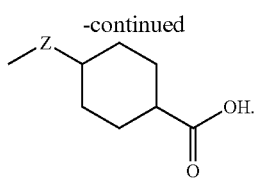

In a further embodiment, rings A and B are both phenyl.
In a preferred embodiment of the invention:
$R^1$ represents a phenyl group substituted by one or two substituents independently selected from halogen, cyano, $C_1$-$C_2$ alkoxy, and $C_1$-$C_2$ alkyl which alkyl group may in turn be optionally substituted by at least one halogen atom;
X represents an oxygen atom or —$CH_2O$—;
m is 0 or 1;
if present, $R^2$ represents a halogen atom;
Y represents $CH_2$;
$R^3$ represents $C_1$-$C_4$ alkyl, or a saturated or unsaturated 3-, 4-, 5- or 6-membered hydrocarbyl ring system, each of the preceding groups being optionally substituted by at least one substituent independently selected from fluorine, hydroxyl, $C_1$-$C_2$ alkoxy, and a saturated or unsaturated 3-, 4-, 5- or 6-membered ring system which may comprise at least one ring heteroatom independently selected from nitrogen, oxygen and sulphur, the ring system itself being optionally substituted by least one substituent independently selected from halogen atoms;
Z represents $CH_2$;
n is 0 or 1;
if present, R represents a halogen atom; and
rings A and B each independently represent a saturated or unsaturated 5- or 6-membered ring system which may comprise at least one ring heteroatom independently selected from nitrogen, oxygen and sulphur.
Examples of compounds of the invention include:
4-((N-Ethyl-4-(2-fluorophenoxy)benzamido)methyl)benzoic acid,
4-((N-(2,2-Difluoroethyl)-4-(2-fluorophenoxy)benzamido)methyl)benzoic acid,
4-((4-(2-Fluorophenoxy)-N-(2,2,2-trifluoroethyl)benzamido)methyl)benzoic acid,
4-((4-(2-Fluorophenoxy)-N-isobutylbenzamido)methyl)benzoic acid,
4-((N-(Cyclopropylmethyl)-4-(2-fluorophenoxy)benzamido)methyl)benzoic acid,
4-((N-(Cyclobutylmethyl)-4-(2-fluorophenoxy)benzamido)methyl)benzoic acid,
4-((4-(2-Fluorophenoxy)-N-((3-methoxycyclobutyl)methyl)benzamido)-methyl)benzoic acid,
4-((4-(2-Fluorophenoxy)-N-isopentylbenzamido)methyl)benzoic acid,
4-((N-(2-Cyclopropylethyl)-4-(2-fluorophenoxy)benzamido)methyl)benzoic acid,
4-((N-(2-Cyclobutylethyl)-4-(2-fluorophenoxy)benzamido)methyl)benzoic acid,
4-((N-Benzyl-4-(2-fluorophenoxy)benzamido)methyl)benzoic acid,
4-((N-(2-Fluorobenzyl)-4-(2-fluorophenoxy)benzamido)methyl)benzoic acid,
4-((4-(2-Fluorophenoxy)-N-(3-methoxybenzyl)benzamido)methyl)benzoic acid,
4-((4-(2-Fluorophenoxy)-N-(4-methoxybenzyl)benzamido)methyl)benzoic acid, 4-((4-(2-Fluorophenoxy)-N-phenethylbenzamido)methyl) benzoic acid,
4-((4-(2-Fluorophenoxy)-N-(3-(2-fluorophenyl)propyl)benzamido)methyl)benzoic acid,
4-((4-(2-Fluorophenoxy)-N-(3-(3-fluorophenyl)propyl)benzamido)methyl)benzoic acid,
4-((4-(2-Fluorophenoxy)-N-((trans-2-phenylcyclopropyl)methyl)benzamido)-methyl)benzoic acid,
(S)-4-((4-(2-Fluorophenoxy)-N-(2-hydroxy-3-phenylpropyl)-benzamido)methyl)benzoic acid,
(R)-4-((4-(2-Fluorophenoxy)-N-(2-hydroxy-3-phenylpropyl)benzamido)-methyl)benzoic acid,
4-((4-(2-Fluorophenoxy)-N-(4-phenylbutyl)benzamido)methyl)benzoic acid,
4-((N-(Cyclopropylmethyl)-4-(o-tolyloxy)benzamido)methyl)benzoic acid,
4-((N-(Cyclobutylmethyl)-4-(o-tolyloxy)benzamido)methyl)benzoic acid,
4-((N-Benzyl-4-(o-tolyloxy)benzamido)methyl)benzoic acid,
4-((N-Phenethyl-4-(o-tolyloxy)benzamido)methyl)benzoic acid,
4-((N-Phenethyl-4-(2-(trifluoromethyl)phenoxy)benzamido)methyl)benzoic acid,
4-((N-Benzyl-4-(2-cyanophenoxy)benzamido)methyl)benzoic acid,
4-((N-Ethyl-4-(2-methoxyphenoxy)benzamido)methyl)benzoic acid,
4-((N-(2,2-Difluoroethyl)-4-(2-methoxyphenoxy)benzamido)methyl)benzoic acid,
4-((N-Isobutyl-4-(2-methoxyphenoxy)benzamido)methyl)benzoic acid,
4-((N-(Cycopropylmethyl)-4-(2-methoxyphenoxy)benzamido)methyl)benzoic acid,
4-(((4-(2-Methoxyphenoxy)-N-(3-phenylpropyl)benzamido)methyl)benzoic acid,
4-((N-(3-(3-Fluorophenyl)propyl) 4-(2-methoxyphenoxy)benzamido)-methyl)benzoic acid,
4-((N-(Cyclopropylmethyl)-4-(2-ethoxyphenoxy)benzamido)methyl)benzoic acid,
4-((4-(2-Chlorophenoxy)-N-(cyclopropylmethyl)benzamido)methyl)benzoic acid,
4-((4-(2-Chlorophenoxy)-N-phenethylbenzamido)methyl) benzoic acid,
4-((N-(Cyclopropylmethyl)-4-(2,6-difluorophenoxy)benzamido)methyl)benzoic acid,
4-((N-(2-Cyclopropylethyl)-4-(2,6-difluorophenoxy)benzamido)methyl)benzoic acid,
4-((N-Benzyl-4-(2,6-difluorophenoxy)benzamido)methyl) benzoic acid,
4-((N-(Cyclopropylmethyl)-4-(2-fluoro-6-methylphenoxy)benzamido)-methyl)benzoic acid,
4-((N-(Cyclobutylmethyl)-4-(2-fluoro-6-methylphenoxy)benzamido)-methyl)benzoic acid,
4-((4-(2-Chloro-6-fluorophenoxy)-N-(cyclopropylmethyl)benzamido)-methyl)benzoic acid,
4-((4-(2-Chloro-6-fluorophenoxy)-N-(2-cyclopropylethyl)benzamido)-methyl)benzoic acid,
4-((N-Benzyl-4-(2-chloro-6-fluorophenoxy)benzamido) methyl)benzoic acid,
4-((4-(2,6-Dimethylphenoxy)-N-isopentylbenzamido)methyl)benzoic acid,
4-((N-Benzyl-4-(2,6-dimethylphenoxy)benzamido)methyl) benzoic acid,
4-((4-(2,6-Dimethylphenoxy)-N-phenethylbenzamido)methyl)benzoic acid,
4-((4-(3-Methoxyphenoxy)-N-phenethylbenzamido)methyl)benzoic acid,
4-((4-(4-Methoxyphenoxy)-N-phenethylbenzamido)methyl)benzoic acid,
4-((4-(3-Chlorophenoxy)-N-phenethylbenzamido)methyl) benzoic acid,
4-((N-(Cyclopropylmethyl)-4-((2-fluorobenzyl)oxy)benzamido)methyl)benzoic acid,
4-((N-(Cyclobutylmethyl)-4-((2-fluorobenzyl)oxy)benzamido)methyl)benzoic acid,
4-((N-Benzyl-4-((2-fluorobenzyl)oxy)benzamido)methyl) benzoic acid,
4-((N-(Cyclopropylmethyl)-2-fluoro-4-(2-fluorophenoxy)-benzamido)methyl)benzoic acid,
4-((N-Benzyl-4-(2-fluorophenoxy)cyclohexanecarboxamido)methyl)benzoic acid,
trans-4-((N-Benzyl-4-(2-methoxyphenoxy)cyclohexanecarboxamido)-methyl)benzoic acid,
cis-4-((N-(3-(3-Fluorophenyl)propyl)-4-(2-methoxyphenoxy)cyclohexanecarboxamido)methyl)benzoic acid,
trans-4-((N-(3-(3-Fluorophenyl)propyl)-4-(2-methoxyphenoxy)cyclohexanecarboxamido)methyl)benzoic acid
2-Fluoro-4-((4-(2-fluorophenoxy)-N-(3-methoxybenzyl) benzamido)methyl)benzoic acid,
4-((4-(2-Fluorophenoxy)-N-propylbenzamido)methyl)benzoic acid,
4-((4-(2-Methoxyphenoxy-N-(2,2,2-trifluoroethyl)benzamido)methyl)benzoic acid,
4-((4-(2-methoxyphenoxy-N-propylbenzamido)methyl) benzoic acid,
4-((N-(2,2-difluoropropyl)-4-(2-methoxyphenoxy)-benzamido)ethyl)benzoic acid,
4-((4-(2-methoxyphenoxy)-N-(3,3,3-trifluoropropyl)-benzamido)methyl)benzoic acid,
4-((N-butyl-4-(2-methoxyphenoxy)benzamido)methyl)benzoic acid,
4-((N-(cyclopropylmethyl)-2-fluoro-4-(2-methoxyphenoxy)-benzamido)methyl)benzoic acid,
4-((N-(cyclopropylmethyl)-4-(2-fluoro-6-methoxyphenoxy)-benzamido)methyl)benzoic acid,
4-((N-(cyclopropylmethyl)-4-(4-fluoro-2-methoxyphenoxy)-benzamido)methyl)benzoic acid,
4-((N-(cyclopropylmethyl)-5-(2-methoxyphenoxy)-picolinamido)methyl)benzoic acid,
4-((4-(o-Tolyloxy)-N-(2,2,2-trifluoroethyl)benzamido) methyl)benzoic acid,
4-((4-(2-Fluorophenoxy)-N-(3,3,3-trifluoropropyl)benzamido)methyl)benzoic acid,
4-((4-(2-Chlorophenoxy)-N-(2,2,2-trifluoroethyl)benzamido)methyl)benzoic acid,
4-((N-Ethyl-4-(o-tolyloxy)benzamido)methyl)benzoic acid,
4-((N-(2,2-Difluoropropyl)-4-(2-fluorophenoxy)benzamido)methyl)benzoic acid,
4-((N-Butyl-4-(2-fluorophenoxy)benzamido)methyl)benzoic acid,
4-((4-(2-Chlorophenoxy)-N-ethylbenzamido)methyl)benzoic acid,
4-((N-(Cyclopropylmethyl)-5-(2-fluorophenoxy)picolinamido)methyl)benzoic acid,
4-((4-(2-Chlorophenoxy)-N-2,2-difluoroethyl)benzamido) methyl)benzoic acid,
4-((N-(Cyclopropylmethyl)-4-(5-fluoro-2-methoxyphenoxy)-benzamido)methyl)benzoic acid,
4-((4-(4-Fluoro-2-methoxyphenoxy)-N-propylbenzamido) methyl)benzoic acid,
4-((4-(5-Fluoro-2-methoxyphenoxy)-N-propylbenzamido) methyl)benzoic acid, 4-((N-(Cyclopropylmethyl)-4-(3-fluoro-2-methoxyphenoxy)benzamido)methyl)benzoic acid,
4-((N-(Cyclopropylmethyl)-5-(2-fluorophenoxy)pyrimidine-2-carboxamido)methyl)benzoic acid,
4-((N-(Cyclopropylmethyl)-5-(2-methoxyphenoxy)pyrimidine-2-carboxamido)methyl)benzoic acid,
4-((5-(2-Methoxyphenoxy)-N-propylpyrimidine-2-carboxamido)methyl)benzoic acid,
and pharmaceutically acceptable salts of any one thereof.

It should be noted that each of the chemical compounds listed above represents a particular and independent aspect of the invention.

The present invention further provides a process for the preparation of a compound of formula (I) or a pharmaceutically acceptable salt thereof as defined above which comprises hydrolysing a compound of formula (II)

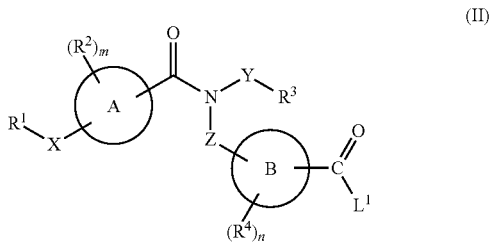
(II)

wherein $L^1$ represents a leaving group (e.g. alkoxy such as methoxy) and $R^1$, X, m, $R^2$, Y, $R^3$, Z, n, $R^4$, A and B are as defined in formula (I), in the presence of a suitable base; and optionally thereafter carrying out one or more of the following procedures:
converting a compound of formula (I) into another compound of formula (I)
removing any protecting groups
forming a pharmaceutically acceptable salt.

The process is conveniently carried out using a base such as lithium hydroxide or sodium hydroxide in a solvent such as 1,4-dioxane or a solvent mixture such as water and tetrahydrofuran, at room temperature or at elevated temperature, e.g. in the range from 20° C. to 100° C.

Compounds of formula (II) may be prepared by reacting a compound of formula (III)

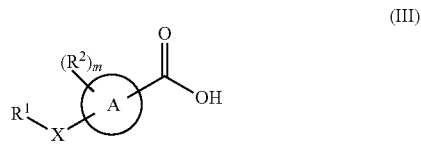
(III)

wherein $R^1$, X, min, $R^2$ and A are as defined in formula (II), with a compound of formula (IV), or a salt (e.g. hydrochloride salt) thereof,

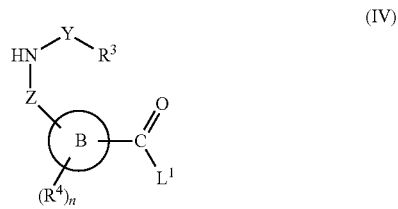
(IV)

wherein $L^1$, Y, $R^3$, Z, n, $R^4$ and B are as defined in formula (II). The reaction is conveniently carried out in the presence of an organic solvent such as tetrahydrofuran or N,N-dimethylformamide, a base such as diisopropylethylamine and an amide coupling agent such as 1-ethyl-3-(3-dimethylaminopropyl)carbodiimide (EDC), O-(7-azabenzotriazol-1-yl)-N,N,N',N'-tetramethyluronium hexafluorophosphate (HATU) or O-(benzotriazol-1-yl)-N,N,N',N'-tetramethyluronium hexafluorophosphate (HBTU).

Compounds of formula (III) may be prepared by oxidising the corresponding aldehyde of formula (V)

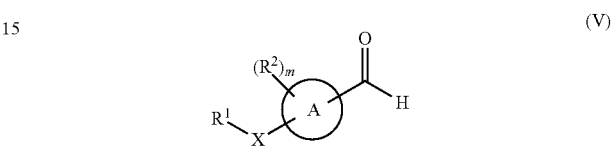
(V)

wherein $R^1$, X, m, $R^2$ and A are as defined in formula (III). Suitable oxidising agents include sodium chlorite.

Compounds of formula (V) in which X represents an oxygen atom or —$CH_2O$— may be prepared by reacting a compound of formula (VI), $R^1$—$(CH_2)_pX'H$, in which p is 0 or 1, X' is oxygen and $R^1$ is as defined in formula (V) with a compound of formula (VII)

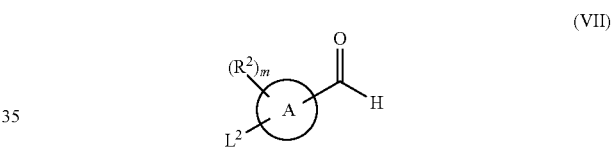
(VII)

in which $L^2$ represents a leaving group (e.g. a halogen atom such as fluorine) and m, $R^2$ and A are as defined in formula (V).

Compounds of formula (III) in which X represents —$CH_2$— may be prepared by reacting a compound of formula (VIII)

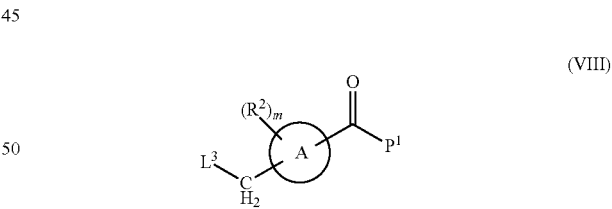
(VIII)

in which $L^3$ represents a leaving group (e.g. a halogen atom such as bromine), $P^1$ represents a suitable protecting group (e.g. an alkoxy group such as methoxy) and m, $R^2$ and A are as defined in formula (III), with a compound of formula (IX), $R^1$—$B(OH)_2$, in which $R^1$ is as defined in formula (III), in the presence of a suitable palladium catalyst, e.g. [1,1'-bis(diphenylphosphino)ferrocene]palladium(II) chloride complex with dichloromethane (see, for example, WO 2012/080221 in the name of Katholieke Universiteit Leuven), followed by ester hydrolysis.

Compounds of formula (III) in which X represents —$CH_2CH_2$— may be prepared by a Heck Reaction by reacting a compound of formula (X)

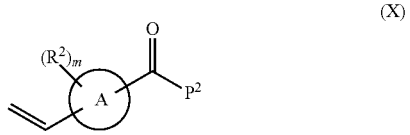

(X)

in which P² is as defined for P¹ above and m, R² and A are as defined in formula (III), with a compound of formula (XI), R¹-L⁴, in which L⁴ represents a leaving group (e.g. a halogen atom such as iodine) and R¹ is as defined in formula (III), in the presence of a suitable palladium catalyst, followed by a hydrogenation reaction and then ester hydrolysis.

Compounds of formula (III) in which X represents —OCH₂— may be prepared by reacting a compound of formula (VIII) as defined above with a compound of formula (XII), R¹—X'H, wherein R¹ and X' are as defined in formula (VI), in the presence of a base such as potassium carbonate and in a solvent such as N,N-dimethylformamide (see, for example, WO 2012/007868 in the name of Pfizer Limited), followed by ester hydrolysis.

Compounds of formula (V) in which X represents —CH₂NR¹⁷ may be prepared by reacting a compound of formula (VII) as defined above with a compound of formula (XIII), R¹—CH²NR¹⁷H, in which R¹ and R¹⁷ are as defined in formula (V), in the presence of a suitable copper catalyst such as copper (I) iodide (see, for example. Kwong et al., Organic Letters, 2002, volume 4, pages 581 to 584).

Compounds of formula (I) in which X represents —NR¹⁷CH₂— may be prepared by reacting a compound of formula (VIII) as defined above with a compound of formula (XIV). R¹—NR¹⁷H, wherein R¹ and R¹⁷ are as defined in formula (III), in the presence of a base such as calcium carbonate and a solvent such as iosbutyramide (see, for example, WO 2007/120096 in the names of AstraZeneca AB and Astex Therapeutics Limited), followed by ester hydrolysis.

Compounds of formula (II) in which X represents —CHF— may be prepared by reacting a compound of formula (XV)

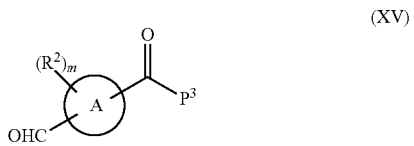

(XV)

in which P³ is as defined for P¹ above and m, R² and A are as defined in formula (III), with a compound of formula (XI) as defined above in the presence of an organolithium such as phenyllithium, followed by a fluorination reaction using, for example, diethylaminosulfur trifluoride and then ester hydrolysis.

Compounds of formula (III) in which X represents —CF₂— may be prepared by reacting a compound of formula (VIIa)

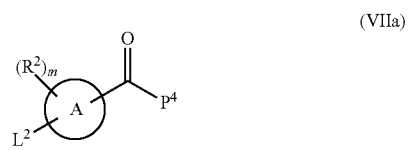

(VIIa)

in which P⁴ is as defined for P¹ above and m, R² and A are as defined in formula (VII), with a compound of formula (IX) as defined above, in the presence of carbon monoxide and a suitable palladium catalyst such as tris-(dibenzylideneacetone)dipalladium (0), followed by a fluorination reaction using, for example, diethylaminosulfur trifluoride and then ester hydrolysis.

Compounds of formula (IV) in which Z is CH₂ or CH(CH₃) may be prepared by reacting a compound of formula (XVI), R³—Y—NH₂, in which R³ and Y are as defined in formula (IV), with a compound of formula (XVII)

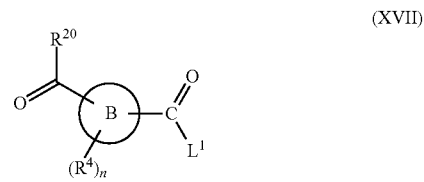

(XVII)

in which R²⁰ represents hydrogen or methyl, and L¹, n, R⁴ and B are as defined in formula (IV), in the presence of a reducing agent such as sodium triacetoxyborohydride.

Compounds of formulae (V) to (XVII) are either commercially available, are well known in the literature or may be prepared using known techniques.

It will be appreciated by those skilled in the art that it may be necessary or desirable at any stage in the synthesis of the compounds of the invention to protect one or more sensitive groups, so as to prevent undesirable side reactions. In particular, it may be necessary or desirable to protect certain functional groups such as hydroxyl, carboxyl or amino groups. Thus, the preparation of the compounds of formula (I) may involve, at an appropriate stage, the introduction and/or removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-napthoate (xinafoate), methanesulphonate or p-toluenesulphonate salt.

In one aspect of the invention, compounds of formula (I) may bear one or more radiolabels. Such radiolabels may be introduced by using radiolabel-containing reagents in the synthesis of the compounds of formula (I), or may be introduced by coupling the compounds of formula (I) to chelating moieties capable of binding to a radioactive metal atom. Such radiolabeled versions of the compounds may be used, for example, in diagnostic imaging studies.

Unless stated otherwise, any atom specified herein may also be an isotope of said atom. For example, the term "hydrogen" encompasses ¹H, ²H and ³H. Similarly carbon atoms are to be understood to include ¹²C, ¹³C and ¹⁴C, nitrogen atoms are to be understood to include ¹⁴N and ¹⁵N, and oxygen atoms are to be understood to include ¹⁶O, ¹⁷O and ¹⁸O.

In a further aspect of the invention, compounds of formula (I) may be isotopically labelled. As used herein, an "isotopically labelled" compound is one in which the abundance of a particular nuclide at a particular atomic position within the molecule is increased above the level at which it occurs in nature.

Compounds of formula (I) and their salts may be in the form of hydrates or solvates which form an aspect of the present invention. Such solvates may be formed with common organic solvents, including but not limited to, alcoholic solvents e.g. methanol, ethanol or isopropanol.

Where compounds of formula (I) are capable of existing in stereoisomeric forms, it will be understood that the invention encompasses the use of all geometric and optical isomers (including atropisomers) of the compounds of formula (I) and mixtures thereof including racemates. The use of tautomers and mixtures thereof also forms an aspect of the present invention. Enantiomerically pure forms are particularly desired.

Compounds of formula (I) and their salts may be amorphous or in a polymorphic form or a mixture of any of these, each of which forms an aspect of the present invention.

The compounds of formula (I) and their pharmaceutically acceptable salts have activity as pharmaceuticals, in particular as modulators (e.g. antagonists) of LPAR5 and, optionally also, as modulators (e.g. antagonists) of LPAR1, and thus may be used in the treatment of: fibrosis of organs such as liver, kidney, skin, lung, heart and the like; liver diseases (acute hepatitis, chronic hepatitis, liver fibrosis, liver cirrhosis, portal hypertension, regenerative failure, non-alcoholic steato hepatitis (NASH), liver hypofunction, hepatic blood flow disorder, and the like); cardiovascular disorders (restenosis, atherosclerosis, heart failure, cardiomyopathy, myocardial infarction, myocardial remodelling, vascular remodelling, hypertension, peripheral arterial occlusive disease, thrombosis, vascular permeability disorders, and the like); cell proliferative disease (cancer (solid tumour, solid tumour metastasis, vascular fibroma, myeloma, multiple myeloma, Kaposi's sarcoma, leukaemia, chronic lymphocytic leukaemia (CLL) and the like) and invasive metastasis of cancer cell, and the like); inflammatory disease (rheumatoid arthritis, osteoarthritis, psoriasis, nephropathy, pneumonia and the like); transplant rejection; gastrointestinal tract disease (irritable bowel syndrome (IBS), inflammatory bowel disease (IBD), abnormal pancreatic secretion, and the like); renal disease; urinary tract-associated disease (benign prostatic hyperplasia or symptoms associated with neuropathic bladder disease, spinal cord tumour, hernia of intervertebral disk, spinal canal stenosis, symptoms derived from diabetes, lower urinary tract disease (obstruction of lower urinary tract, and the like); inflammatory disease of lower urinary tract (dysuria; overactive bladder, interstitial cystitis, frequent urination and the like); pancreas disease; abnormal angiogenesis associated disease (arterial obstruction and the like); systemic sclerosis including localised scleroderma; brain associated disease (cerebral infarction, cerebral hemorrhage, and the like); pain (neuropathic pain, peripheral neuropathy, lightning pains, phantom pains, shooting pains, acute pain, inflammatory pain, neuralgia, tissue injury pain and the like); ocular disease (choroidal neovascularisation, age related macular degeneration (AMD), diabetic retinopathy, proliferative vitreoretinopathy (PVR), cicatricial pemphigold, glaucoma filtration surgery scarring and the like); pulmonary disease (chronic obstructive pulmonary disease, asthma, acute respiratory distress syndrome); psychiatric disorders; neurodegenerative diseases; cerebral and peripheral nerve disorders; scarring disorders; and wound healing.

Thus, the present invention provides a compound of formula (I) or a pharmaceutically acceptable salt thereof as hereinbefore defined for use in therapy, in particular for the treatment of conditions whose development or symptoms are linked to LPAR5 or LPAR1 activity.

The present invention also provides the use of a compound of formula (I) or a pharmaceutically acceptable salt thereof as hereinbefore defined for the preparation of a medicament for the treatment of conditions whose development or symptoms are linked to LPAR5 or LPAR1 activity.

In the context of the present specification, the terms "therapy" and "treatment" also include "prophylaxis" unless there are specific indications to the contrary. The terms "therapeutic", "therapeutically" and "treating" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

In particular, the compounds of the invention (including pharmaceutically acceptable salts) may be used in the treatment of pain (such as neuropathic pain), atherosclerosis and fibrosis.

"Pain" means the more or less localised sensation of discomfort, distress or agony resulting from the stimulation of specialised nerve endings. There are many types of pain (as illustrated above) and the goal of treatment of pain is to reduce the degree or severity of pain perceived by a treatment subject.

The invention also provides a method of treating pain (e.g. neuropathic pain), atherosclerosis or fibrosis which comprises administering to a patient in need thereof a therapeutically effective amount of a compound of formula (I) or a pharmaceutically acceptable salt thereof as hereinbefore defined.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore the present invention further provides a pharmaceutical composition comprising a compound of formula (I) or a pharmaceutically acceptable salt thereof as hereinbefore defined, in association with a pharmaceutically acceptable adjuvant, diluent or carrier.

The invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins, such as human serum albumin, buffer substances such as phosphates, glycerine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, topically, parenterally, by inhalation spray, rectally, nasally, buccally, vaginally or via an implanted reservoir. Oral or topical administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of the invention (that is, compounds of formula (I) and pharmaceutically acceptable salts thereof) may also be administered in conjunction with other compounds used for the treatment of the above conditions.

The invention therefore further relates to combination therapies wherein a compound of the invention or a pharmaceutical composition or formulation comprising a compound of the invention is administered concurrently, sequentially or as a combined preparation with another therapeutic agent or agents, for the treatment of one or more of the conditions previously indicated. Such therapeutic agents may be selected from the following:

(i) opioid agonists, partial agonists or antagonists such as, for example, morphine, buprenorphine, alfentanil, fentanyl, pethidine, oxycodone, tramadol and codeine, and equivalents and pharmaceutically active isomer(s) and/or metabolite(s) thereof;

(ii) antidepressants such as, for example, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robaizotan, sertraline, sibutramine, thionisoxetine, tranylcypromaine, trazodone, trimipramine, venlafaxine, ketamine, vortioxetine, and equivalents and pharmaceutically active isomer(s) and/or metabolite(s) thereof;

(iii) anxiolytics including, for example, alnespirone, azapirones, benzodiazepines, barbiturates, and equivalents and pharmaceutically active isomer(s) and/or metabolite(s) thereof. Example anxiolytics include adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, and zolazepam; and equivalents and pharmaceutically active isomer(s) and/or metabolite(s) thereof;

(iv) anticonvulsants including, for example, carbamazepine, valproate, lamotrigine, and gabapentin, and equivalents and pharmaceutically active isomer(s) and/or metabolite(s) thereof;

(v) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, and zomitriptan, and equivalents and pharmaceutically active isomer(s) and/or metabolite(s) thereof;

(vi) stroke therapies including, for example, abciximab, activase, NXY-059, citicoline, crobenetine, desmoteplase, repinotan, traxoprodil, and equivalents and pharmaceutically active isomer(s) and/or metabolite(s) thereof;

(vii) urinary incontinence therapies including, for example, darafenacin, falvoxate, oxybutynin, propiverine, robalzotan, solifenacin, and tolterodine, and equivalents and pharmaceutically active isomer(s) and/or metabolite(s) thereof;

(viii) neuropathic pain therapies including, for example, gabapentin, lidoderm, and pregablin, and equivalents and pharmaceutically active isomer(s) and/or metabolite(s) thereof; and (ix) nociceptive pain therapies such as, for example, celecoxib, etoricoxib, lumiracoxib, rofecoxib, valdecoxib, diclofenac, loxoprofen, naproxen, and paracetamol, and equivalents and pharmaceutically active isomer(s) and/or metabolite(s) thereof.

Such combination products employ the compounds of this invention within the dosage range described herein and the other pharmaceutically active agent within approved dosage ranges.

The present invention will now be further explained by reference to the following illustrative examples. In the illustrative examples, the compounds synthesised are both named and illustrated structurally. Whilst every effort has been made to ensure that the chemical names and the chemical structures are consistent, if any inconsistencies occur the illustrated chemical structure should be taken to be correct, unless the illustrated chemical structure is chemically impossible.

Nuclear magnetic resonance (NMR) spectra were typically recorded at 400 MHz; the chemical shifts ($\delta$) are reported in parts per million. Spectra were recorded using a Bruker 400 Avance instrument fitted with a 5 mm BBFO probe or DUL probe. Instrument control was by Bruker TopSpin 2.1 software, unless stated otherwise.

Purity was assessed using UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of MeCN or MeOH mixed with water containing either 0.05% formic acid or 0.025% $NH_4OH$. Mass spectra were recorded with a Waters SQD single quadrupole mass spectrometer using atmospheric pressure ionisation, unless stated otherwise.

Compounds were purified using normal phase chromatography on silica or alumina, or by reverse-phase chromatographic methods, using Biotage or Isolute KPNH Cartridge, SCX cartridge and SCX-2 solid phase extraction cartridges.

Preparative HPLC was typically performed using an Agilent Technologies 1100 Series system or a Waters autopurification LC/MS system typically using Waters 19 mm id×100 mm long C18 columns such as XBridge or SunFire 5 μm materials at room temperature. Mobile phases typically consisted of MeCN or MeOH mixed with water containing either 0.1% formic acid or 0.1% $NH_4OH$, unless stated otherwise.

The compound names were generated using ChemBioDraw Ultra 12.0 (Perkin Elmer Inc.).

Generally:

(i) Operations were typically carried out at ambient temperature, i.e. in the range 15-25° C., and under an atmosphere of an inert gas such as nitrogen or argon unless otherwise stated.

(ii) Inorganic solutions were aqueous unless otherwise stated.

(iii) Drying of solutions was carried out with magnesium sulfate or sodium sulfate, or using a phase-separating cartridge.

(iv) Concentration was typically carried out by rotary evaporation under vacuum.

(v) Column chromatography and high pressure liquid chromatography (HPLC) were performed on silica or reverse-phase C18 silica; unless otherwise stated, preparative HPLC was carried out using MeCN/water (both with 0.1% $NH_4OH$).

(vi) Yields, where present, are not necessarily the maximum attainable.

(vii) In general, the structures of the end-products of the Formula I were confirmed by nuclear magnetic resonance (NMR) and/or mass spectral (MS) techniques; electrospray ionization (in positive or negative mode, $ES^+$ or $ES^-$) mass spectral data were obtained using a Waters Amity SQD spectrometer and, where appropriate, either positive ion data or negative ion data were collected; NMR chemical shift values were measured on the delta scale; the following abbreviations have been used: s, singlet; m, multiplet; br, broad; br s, broad singlet.

(viii) Intermediates were not necessarily fully purified but their structures and purity were assessed by thin layer chromatography (TLC), HPLC, infra-red (IR) and/or NMR analysis.

The following abbreviations are used:

bp boiling point
DBU 1,8-diazabicyclo[5.4.0]undec-7-ene
DCM dichloromethane
DIPEA diisopropylethylamine
DMF N,N-dimethylformamide
DMSO dimethyl sulfoxide
DMSO-$d_6$ deuterated dimethyl sulfoxide
eq equivalent(s)
Et ethyl
$Et_2O$ diethyl ether
EtOAc ethyl acetate
EtOH ethanol
h hour(s)
HATU O-(7-azabenzotriazol-1-yl)-N,N,N',N'-tetramethyluronium hexafluorophosphate
HBTU O-(benzotriazol-1-yl)-N,N,N',N'-tetramethyluronium hexafluorophosphate
HCl hydrochloric acid
IMS industrial methylated spirit
iPr isopropyl
M molar
Me methyl
MeCN acetonitrile MeOH methanol
mmHg millimeters of mercury
mmol millimoles
NaOH sodium hydroxide
petrol petroleum ether, typically bp 40-60° C.
RT room temperature, typically 15-25° C.
THF tetrahydrofuran A. Preparation of Acid Intermediates

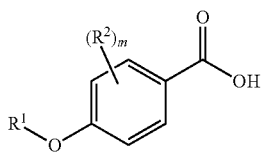

(A)

Intermediate A1: 4-(2-Fluorophenoxy)benzoic acid

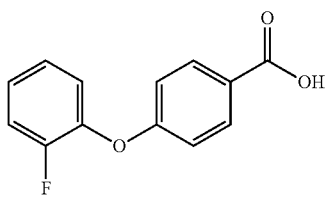 [SMILES: O=C(O)c1ccc(Oc2ccccc2F)cc1]

Step (i) Potassium carbonate (31.1 g, 225 mmol) was added to a solution of 4-fluorobenzaldehyde (7.96 mL, 75 mmol) and 2-fluorophenol (9 mL, 98 mmol) in DMF (100 mL). The mixture was heated at 100° C. under nitrogen for 24 h. After cooling to RT, the mixture was partitioned between EtOAc (200 mL) and water (150 mL). The aqueous phase was extracted with EtOAc (200 mL). The combined organic phases were washed with brine (3×50 mL), dried and concentrated. The residue was purified by silica chromatography (0-20% EtOAc/petrol) to give 4-(2-fluorophenoxy)benzaldehyde (crude, 17.7 g) which was used in the next step (ii) without further purification or characterisation.

Step (ii) 4-(2-Fluorophenoxy)benzaldehyde (crude, 17.7 g) was dissolved in THF (100 mL), tert-butanol (100 mL) and water (50 mL), and the mixture cooled in an ice-water bath. 2-Methyl-2-butene (43.3 mL, 409 mmol), potassium dihydrogen phosphate (27.8 g, 205 mmol) and sodium chlorite (23.12 g, 205 mmol) were added sequentially and the mixture was stirred at RT for 18 h. The mixture was partitioned between water (100 mL) and Et$_2$O (200 mL), and the aqueous phase extracted with Et$_2$O (200 mL). The combined organic phases were washed sequentially with saturated sodium thiosulfate solution (100 mL) and brine (100 mL), dried and concentrated. Addition of EtOAc and petrol resulted in a precipitate which was isolated by filtration and air-dried to give the title compound (11.95 g, 63%) as a pale yellow solid.

MS ES$^-$: 231

Intermediate A2: 4-(2,6-Dimethylphenoxy)benzoic acid

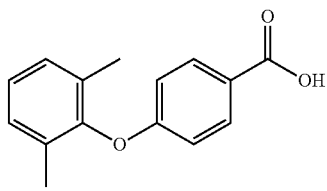 [SMILES: Cc1cccc(C)c1Oc1ccc(C(=O)O)cc1]

Step (i) Tripotassium phosphate (9.27 g, 43.7 mmol) and palladium(II) acetate (0.490 g, 2.18 mmol) were added to a solution of ethyl 4-bromobenzoate (5 g, 21.8 mmol) and 2,6-dimethylphenol (3.73 g, 30.6 mmol) in toluene (40 mL). The mixture was degassed for about 5 minutes and purged with nitrogen. A solution of di-tert-butyl(2',4',6'-triisopropylbiphenyl-2-yl)phosphine (1.390 g, 3.27 mmol) in toluene (5 mL) was added. The mixture was degassed for a further 2 minutes, purged with nitrogen, and heated under reflux for 1.5 h. The mixture was partitioned between water and EtOAc (50 mL each), and the organic phase dried and concentrated. The residue was purified by silica chromatography (0-20% EtOAc/petrol) to give ethyl 4-(2,6-dimethylphenoxy)benzoate (crude, 2 g) which was used in the next step (ii) without further purification or characterisation.

Step (ii) Ethyl 4-(2,6-dimethylphenoxy)benzoate (crude, 2 g) was dissolved in MeOH (7 mL). NaOH (2 M, 7 mL) was added, and the mixture heated under microwave irradiation at 120° C. for 20 minutes. The mixture was acidified to pH 1 (2 M HCl), diluted with water (50 mL) and extracted with EtOAc (50 mL). The organic phase was dried and concentrated. The residue was dissolved/suspended in EtOAc (50 mL) and the mother liquor concentrated. This process was repeated with Et$_2$O:EtOAc (4:1, 20 mL) and then Et$_2$O (20 mL) to give the title compound (crude, 800 mg) which was used in the next step without further purification or characterisation.

Intermediate A3: 4-(2,6-Difluorophenoxy)benzoic acid

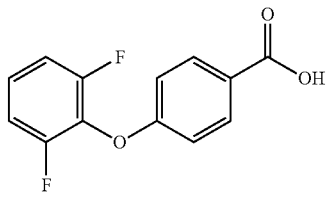 [SMILES: O=C(O)c1ccc(Oc2c(F)cccc2F)cc1]

Step (i) 4-(2,6-Difluorophenoxy)benzaldehyde was prepared as described for 4-(2-fluorophenoxy)benzaldehyde (Intermediate A1, step (i)) from 4-fluorobenzaldehyde and 2,6-difluorophenol, except with 2 eq potassium carbonate and 1.2 eq of the phenol.

$^1$H NMR (400 MHz, DMSO-d$_6$) δ ppm 7.12-7.21 (m, 2H) 7.32-7.50 (m, 3H) 7.90-7.99 (m, 2H) 9.94 (s, 1H)

Step (ii) 4-(2,6-Difluorophenoxy)benzaldehyde (0.500 g, 2.14 mmol) was dissolved in tert-butanol (6 mL) and water (3 mL). 2-Methyl-2-butene (2 M in THF, 5.34 mL, 10.67 mmol), potassium dihydrogen phosphate (0.73 g, 5.34 mmol) and sodium chlorite (0.72 g, 2.14 mmol) were added sequentially and the mixture was stirred at RT for 4 h. The mixture was partitioned between water (30 mL) and Et$_2$O (30 mL). The aqueous phase was acidified with HCl (2 M, 10 mL) and extracted with Et$_2$O (30 mL). The combined organic phases were washed sequentially with saturated sodium thiosulfate solution (15 mL) and brine (15 mL), dried and concentrated. The residue was loaded onto an anion exchange cartridge. After washing with MeCN, the product was eluted with 2 M HCl/MeCN then concentrated to give the title compound (0.367 g, 69%) as a white solid.

MS ES$^-$: 249

Intermediate A4:
4-(2-Fluoro-6-methylphenoxy)benzoic acid

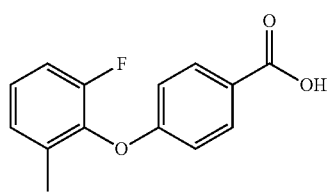 [SMILES: Cc1cccc(F)c1Oc1ccc(C(=O)O)cc1]

Step (i) 4-(2-Fluoro-6-methylphenoxy)benzaldehyde was prepared as described for 4-(2-fluorophenoxy)benzaldehyde (Intermediate A1, step (i)) from 4-fluorobenzaldehyde and 2-fluoro-6-methylphenol, and used in the next step (ii) without further purification or characterisation.

Step (ii) The title compound was prepared as described for 4-(2-fluorophenoxy)benzoic acid (Intermediate A1, step (ii)) from 4-(2-fluoro-6-methylphenoxy)benzaldehyde (step (i) above), with recrystallisation of the product from EtOAc/petrol, and used in the next step without further purification or characterisation.

Intermediate A5:
4-(2-Chloro-6-fluorophenoxy)benzoic acid

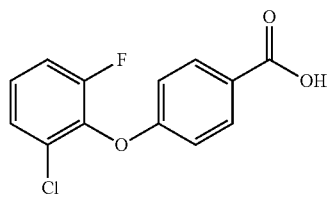 [SMILES: O=C(O)c1ccc(Oc2c(F)cccc2Cl)cc1]

Step (i) 4-(2-Chloro-6-fluorophenoxy)benzaldehyde was prepared as described for 4-(2-fluorophenoxy)benzaldehyde (Intermediate A1, step (i)) from 4-fluorobenzaldehyde and 2-chloro-6-fluorophenol.

$^1$H NMR (400 MHz, DMSO-d$_6$) δ ppm 7.07-7.17 (m, 2H) 7.40-7.60 (m, 3H) 7.89-7.99 (m, 2H) 9.93 (s, 1H)

Step (ii) The title compound was prepared as described for 4-(2-fluorophenoxy)benzoic acid (Intermediate A1, step (ii)) from 4-(2-chloro-6-fluorophenoxy)benzaldehyde (step (i) above).

MS ES$^-$: 265

Intermediate A6:
2-Fluoro-4-(2-fluorophenoxy)benzoic acid

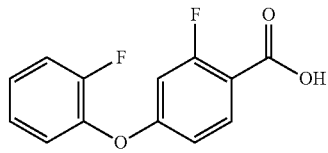 [SMILES: O=C(O)c1ccc(Oc2ccccc2F)cc1F]

Step (i) 2-Fluoro-4-(2-fluorophenoxy)benzaldehyde was prepared as described for 4-(2-fluorophenoxy)benzaldehyde (Intermediate A1, step (i)) from 2,4-difluorobenzaldehyde and 2-fluorophenol, except with 1 eq of the phenol and heating at 80° C.

MS ES$^+$: 235

Step (ii) The title compound was prepared as described for 4-(2-fluorophenoxy)benzoic acid (Intermediate A1, step (ii)) from 2-fluoro-4-(2-fluorophenoxy)benzaldehyde (step (i) above).

MS ES$^+$: 251

Intermediate A7: 4-((2-Fluorobenzyl)oxy)benzoic acid

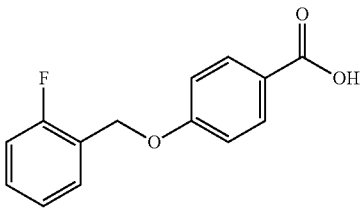 [SMILES: O=C(O)c1ccc(OCc2ccccc2F)cc1]

Step (i) Sodium hydride (60% dispersion in mineral oil, 0.177 g, 4.43 mmol) was added to a mixture of 4-fluorobenzaldehyde (0.437 mL, 4.03 mmol) and (2-fluorophenyl)methanol (0.508 g, 4.03 mmol) in DMF (20 mL). The reaction was stirred under nitrogen at room temperature for 18 h. The mixture was diluted with EtOAc and washed with sodium bicarbonate and then brine. The organic phase was dried and concentrated to give 4-((2-fluorobenzyl)oxy)benzaldehyde as a residue which was used in the next step (ii) without further purification or characterisation.

Step (ii) The title compound was prepared as described for 4-(2,6-difluorophenoxy)benzoic acid (Intermediate A3, step (ii)) from 4-((2-fluorobenzyl)oxy)benzaldehyde (step (i) above) and used in the next step without further purification or characterisation.

Intermediate A8:
2-Fluoro-4-(2-methoxyphenoxy)benzoic acid

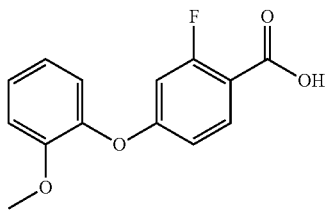 [SMILES: COc1ccccc1Oc1ccc(C(=O)O)c(F)c1]

Prepared by a two step process analogous to that described for Intermediate A1 in which, in the first step, 2,4-difluorobenzaldehyde was reacted with 2-methoxyphenol to yield 2-fluoro-4-(2-methoxyphenoxy)benzaldehyde which, without further purification or characterisation, was used in the second oxidation step to yield the titled compound.

The intermediates 4-(2-methylphenoxy)benzoic acid and 4-(2-chlorophenoxy)benzoic acid used in the preparation of several of the final compounds is known in the art and is commercially available from chemical suppliers such as Apollo Scientific.

B. Preparation of 4-(Aminomethyl)benzoates and analogues

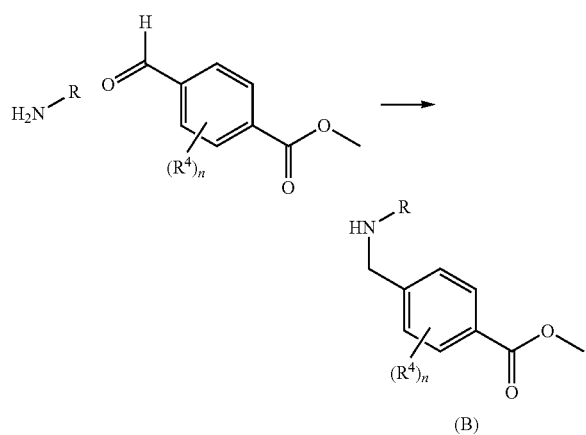

Intermediates of formula (B) shown in Table I below were prepared according to one of the following methods R1 to R6:

Method R1

A solution of the amine (50 mmol) and methyl 4-formylbenzoate (50 mmol) in IMS or EtOH (100 mL) was heated under reflux for 2 h. After cooling, the mixture was concentrated and the residue was dissolved in MeOH (400 mL). The resulting solution was cooled in an ice-water bath and sodium borohydride (40 mmol) was added, typically in several portions over 10 minutes. The mixture was stirred and allowed to warm to RT. After 2 h, the mixture was concentrated. The residue was stirred in water (20 mL). The mixture was acidified HCl (2 M) and extracted with DCM (3×20 mL). The aqueous phase was basified with solid NaOH and extracted with DCM (3×50 mL). The latter extracts were dried and concentrated to give the intermediate of formula (B).

Method R2

As for Method R1, except that after concentrating the sodium borohydride reaction, the residue was dissolved/suspended in HCl (2 M) or HCl (4 M in 1,4-dioxane). The resulting precipitate was filtered, washed with water, and dried to give the hydrochloride salt of the intermediate of formula (B).

Method R3

A solution of the amine (5 mmol) and methyl 4-formylbenzoate (5 mmol) was stirred in DCM (20 mL) for 2 h at RT. Sodium triacetoxyborohydride (10 mmol) was added, followed by acetic acid (6 mmol). After stirring for 2 h, the mixture was diluted with DCM (20 mL) and washed with NaOH (2 M, 20 mL) or saturated sodium bicarbonate solution (20 mL). The aqueous phase was extracted with DCM (20 mL), and the combined organic phases dried and concentrated to give the intermediate of formula (B).

Method R4

As for Method R1, except that after concentrating the sodium borohydride reaction and adding water and HCl, the mixture was basified with sodium hydrogencarbonate and extracted with EtOAc. The organic phase was dried and concentrated, and the residue was dissolved/suspended in an organic solvent, typically EtOAc or Et$_2$O. HCl (4 M in MeOH) was added, and the mixture stirred at RT. The resulting precipitate was filtered, and the filter cake air-dried to give the hydrochloride salt of the intermediate of formula (B).

Method R5

As for Method R1, except that (a) in the imine formation, triethylamine (typically 1 eq) was added, and (b) after concentrating the sodium borohydride reaction, the residue was partitioned between (i) sodium hydrogencarbonate or sodium hydroxide and (ii) EtOAc or DCM. The organic phase was dried and concentrated to give the intermediate of formula (B). In some cases, the residue was dissolved/suspended in an organic solvent, typically EtOAc or Et$_2$O. HCl (4 M in MeOH) was added, and the mixture stirred at RT. The resulting precipitate was filtered, and the filter cake air-dried to give the hydrochloride salt of the intermediate of formula (B). In some cases, the residue was dissolved/suspended in aqueous HCl (2 M). The resulting precipitate was filtered, washed with water, and dried to give the hydrochloride salt of the intermediate of formula (B).

Method R6

As for Method R1, except that after stirring the sodium borohydride reaction for 1 h, the mixture was quenched with HCl (2 M). The resulting precipitate was isolated by filtration and dried under vacuum to give the hydrochloride salt of the intermediate of formula (B).

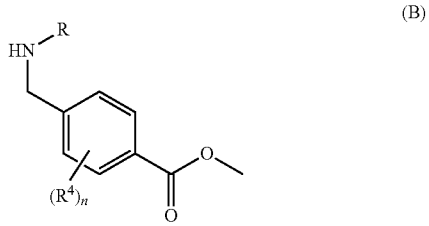

TABLE 1

| Intermediate | R | Product | Method | Data |
|---|---|---|---|---|
| B1 | CH$_2$CH$_3$ | methyl 4-((ethylamino)methyl)benzoate | R1, using 2M EtNH$_2$ in THF (1.8 eq) | MS ES$^+$: 194 |
| B2 | CH$_2$CHF$_2$ | methyl 4-(((2,2-difluoroethyl)amino)methyl)-benzoate | R1 | MS ES$^+$: 230 |
| B3 (HCl salt) | CH$_2$CF$_3$ | methyl 4-(((2,2,2-trifluoroethyl)amino)methyl)-benzoate hydrochloride | R2, using 5 eq NaBH$_4$ | MS ES$^+$: 248 |
| B4 (HCl salt) | CH$_2$iPr | methyl 4-((isobutylamino)methyl)-benzoate hydrochloride | R4 | n/a |
| B5 (HCl salt) | (cyclopropylmethyl) | methyl 4-(((cyclopropylmethyl)amino)-methyl)benzoate hydrochloride | R4 | MS ES$^+$: 220 |
| B6 (HCl salt) | (cyclobutylmethyl) | methyl 4-(((cyclobutylmethyl)amino)-methyl)benzoate hydrochloride | R5 from Amine 1* | MS ES$^+$: 234 |
| B7 (HCl salt) | (isopentyl) | methyl 4-((isopentylamino)methyl)-benzoate hydrochloride | R4 | MS ES$^+$: 236 |
| B8 (HCl salt) | (2-cyclopropylethyl) | methyl 4-(((2-cyclopropylethyl)amino)-methyl)benzoate hydrochloride | R4, from Amine 2** | MS ES$^+$: 234 |
| B9 (HCl salt) | (2-cyclobutylethyl) | methyl 4-(((2-cyclobutylethyl)amino)-methyl)benzoate hydrochloride | R4, from Amine 3*** | MS ES$^+$: 248 |
| B10 (HCl salt) | (benzyl) | methyl 4-((benzylamino)methyl)benzoate hydrochloride | R4 | MS ES$^+$: 256 |
| B11 (HCl salt) | (2-fluorobenzyl) | methyl 4-(((2-fluorobenzyl)amino)methyl)-benzoate hydrochloride | R2 | MS ES$^+$: 274 |
| B12 (HCl salt) | (3-methoxybenzyl) | methyl 4-(((3-methoxybenzyl)amino)-methyl)benzoate hydrochloride | R2 | MS ES$^+$: 286 |

TABLE 1-continued

| Intermediate | R | Product | Method | Data |
|---|---|---|---|---|
| B13 (HCl salt) | 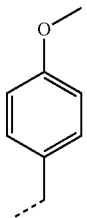 | methyl 4-(((4-methoxybenzyl)amino)methyl)benzoate hydrochloride | R2 | MS ES+: 286 |
| B14 | 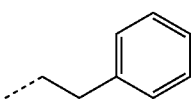 | methyl 4-((phenethylamino)methyl)benzoate | R3 | MS ES+: 270 |
| B15 (HCl salt) | 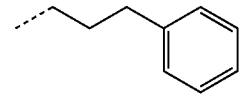 | methyl 4-(((3-phenylpropyl)amino)methyl)benzoate hydrochloride | R6 | MS ES+: 284 |
| B16 | 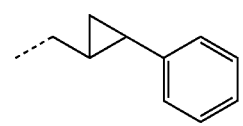 | methyl 4-((((trans-2-phenylcyclopropyl)methyl)amino)methyl)benzoate | R3 | MS ES+: 296 |
| B17 (HCl salt) | 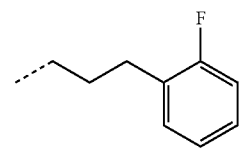 | methyl 4-(((3-(2-fluorophenyl)propyl)amino)methyl)benzoate hydrochloride | R5 | MS ES+: 302 |
| B18 (HCl salt) | 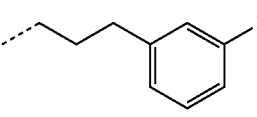 | methyl 4-(((3-(3-fluorophenyl)propyl)amino)methyl)benzoate hydrochloride | R5 | MS ES+: 302 |
| B19 (HCl salt) | 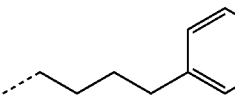 | methyl 4-(((4-phenylbutyl)amino)methyl)benzoate hydrochloride | R4 | n/a |
| B19a (HCl salt) | CH$_2$CH$_2$CH$_3$ | methyl 4-((propylamino)methyl)benzoate hydrochloride | R2 | n/a |
| B19b (HCl salt) | 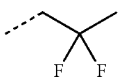 | methyl 4-(((2,2-difluoropropyl)amino)methyl)benzoate | R5 | MS ES+: 244 |
| B19c | 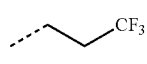 | methyl 4-(((3,3,3-trifluoropropyl)amino)methyl)benzoate | R5 | MS ES+: 262 |

TABLE 1-continued

| Intermediate | R | Product | Method | Data |
|---|---|---|---|---|
| B19d (HCl salt) |  | methyl 4-((butylamino)methyl)-benzoate hydrochloride | R2 | n/a |

*Amine 1: Cyclobutylmethanamine hydrochloride
A solution of borane in THF (1M, 296 mL, 296 mmol) was added to a solution of cyclobutanecarbonitrile (20 g, 247 mmol) in THF (60 mL) under argon, and the mixture heated under reflux overnight. The mixture was cooled in an ice-water bath and MeOH (120 mL) added dropwise while keeping the temperature of the mixture below 20° C. HCl in MeOH (4M, 300 mL) was added, again keeping the temperature below 20° C. The resulting solution was heated under reflux for 2.5 h. After cooling, the mixture was concentrated. The residue was diluted with MeOH (100 mL) and concentrated, and this process was repeated. Ether was added to the residue, and the mixture stirred for 30 minutes before filtering to give the title compound (25.9 g, 86%) as a white solid. $^1$H NMR (300 MHz, DMSO-$d_6$) δ ppm 1.70-1.86 (m, 4H) 1.97-2.04 (m, 2H) 2.46-2.61 (m, 1H) 2.75-2.84 (m, 2H) 8.02 (br s, 3H)

**Amine 2: 2-Cyclopropylethanamine
Sulfuric acid (17.25 mL, 324 mmol) was added dropwise to a suspension of lithium aluminium hydride (24.56 g, 647 mmol) in Et$_2$O (900 mL) in an ice-water bath under argon. The mixture was stirred at RT for 1 h. A solution of 2-cyclopropylacetonitrile (17.5 g, 216 mmol) in Et$_2$O (100 mL) was added and the mixture heated under reflux for 18 h, The mixture was cooled in an ice-water bath and sodium sulfate decahydrate was added until effervescence ceased. The mixture was filtered and concentrated to give the title compound (crude, 18.6 g) which was used without further purification or characterisation.

***Amine 3: 2-Cyclobutylethanamine
Prepared as described for Amine 2 from 2-cyclobutylacetonitrile and used in the next step without further purification or characterisation.

Intermediate B20: (S)-methyl 4-(((2-hydroxy-3-phenylpropyl)amino)methyl)benzoate

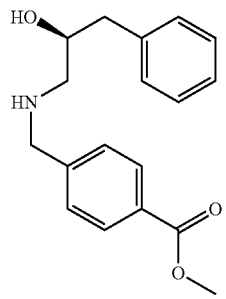

Step (i) (S,S)-(+)-N,N'-Bis(3,5-di-tert-butylsalicylidene)-1,2-cyclohexanediaminocobalt(II) (0.048 g, 0.080 mmol), THF (0.25 mL) and acetic acid (0.018 mL, 0.318 mmol) were added to 2-benzyloxirane (4.27 g, 31.8 mmol). The mixture was cooled in an ice-water bath and water (0.129 mL, 7.16 mmol) was added in one portion. After stirring at RT overnight, the mixture was distilled under vacuum (2 mmHg, bp 60-80° C.) to give (S)-2-benzyloxirane (crude, 2.74 g) which was used in the next step without further purification or characterisation.

Step (ii) (S)-2-Benzyloxirane (step (i) above) (2.74 g, 20.42 mmol) was added to a solution of methyl 4-(aminomethyl)benzoate hydrochloride (7.41 g, 36.8 mmol) and DIPEA (8.92 mL, 51.1 mmol) in MeOH (300 mL). After stirring for 3 days, the reaction mixture was concentrated. The residue was partitioned between saturated sodium hydrogencarbonate solution (200 mL) and DCM (2×200 mL). The aqueous phase was extracted with DCM (200 mL). The combined organic phases were concentrated and purified by silica chromatography (0-10% MeOH/DCM) and then reverse-phase chromatography on C18 silica (eluted with 0-95% MeOH/H$_2$O with 0.1% NH$_4$OH) to give the title compound (3.27 g, 53%) as a pale brown gum.

MS ES$^+$: 300

Intermediate B21: (R)-methyl 4-(((2-hydroxy-3-phenylpropyl)amino)methyl)benzoate

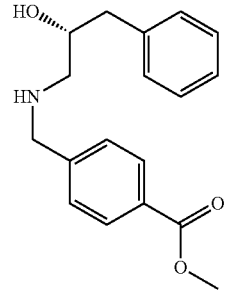 [SMILES: COC(=O)c1ccc(CNC[C@H](O)Cc2ccccc2)cc1]

Step (i) Prepared as described for (S)-2-benzyloxirane (Intermediate B48, step (i)), except using (R,R)-(−)-N,N'-bis(3,5-di-tert-butylsalicylidene)-1,2-cyclohexanediaminocobalt(II) to give (R)-2-benzyloxirane which was used in the next step without further purification or characterisation.

Step (ii) Prepared as described for (S)-methyl 4-(((2-hydroxy-3-phenylpropyl)amino)methyl)benzoate (Intermediate B20, step (ii)) from (R)-2-benzyloxirane (step (i) above) and methyl 4-(aminomethyl)benzoate hydrochloride to give the title compound as a pale brown gum.

MS ES$^+$: 300

C. Preparation of Intermediate Eaters

Intermediates of formula (C) shown in Tables 2 to 4 below were prepared according to one of the following methods E1 to E5:

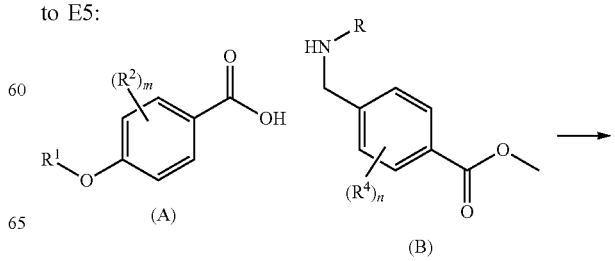

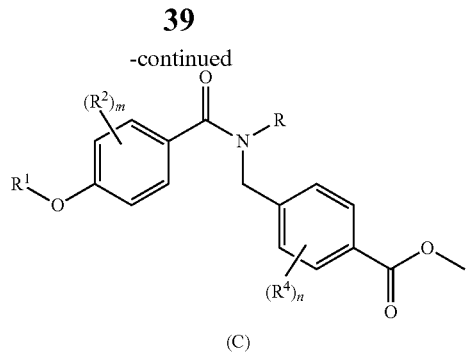

(C)

Method E1

Triethylamine (6 mmol), 1-hydroxy-7-azabenzotriazole (2.4 mmol) and 1-ethyl-3-(3-dimethylaminopropyl)carbodiimide (EDC) (2.4 mmol) were added to a solution/suspension of the relevant amine or amine hydrochloride (2 mmol) and 4-phenoxybenzoic acid (2 mmol) in THF (10 mL). The reaction was stirred at RT for 18 h. (In cases where the amine hydrochloride was used, an extra 2 mmol triethylamine was added.) The mixture was partitioned between (i) water or saturated sodium hydrogencarbonate solution (10 mL) and (ii) DCM or EtOAc (10 mL). The aqueous phase was extracted with further DCM or EtOAc, and the combined organic phases dried and concentrated. The residue was purified by silica chromatography (typically 0-100% EtOAc/petrol).

Method E2

DIPEA (2.2 mmol) and HBTU (1.1 mmol) were added to a solution of the relevant acid in DMF (5 mL) and the mixture stirred for 5 minutes at RT. The relevant amine or amine hydrochloride (0.95 mmol) and DBU (1.5 mmol) were added. The mixture was stirred for 1 h at RT. (In cases where the amine hydrochloride was used, an extra 1 mmol DIPEA was added.) The mixture was partitioned between EtOAc (30 mL) and either water or saturated sodium hydrogencarbonate solution (30 mL). In some cases the aqueous phase was further extracted with EtOAc. The combined organic phases were dried and concentrated. The residue was purified by silica chromatography (typically 0-100% EtOAc/petrol).

Method E3

Thionyl chloride or oxalyl chloride (3-12 mmol) was added to a solution of the acid (3 mmol) in DCM (10 mL) in an ice-water bath. In some cases, several drops of DMF were added. The reaction mixture was stirred at RT for 4 h and then concentrated to yield the crude acid chloride, which was dissolved in THF (3 mL) and added to a solution/suspension of the amine hydrochloride (2 mmol) and potassium carbonate (10 mmol) in THF (10 mL). The reaction was heated under reflux for 18 h. After cooling, the mixture was partitioned between water and EtOAc. The organic phase was dried and concentrated and the residue purified by silica chromatography (0-50% EtOAc/petrol).

Method E4

HATU (1.1 mmol) was added to a solution of the acid (1 mmol) and DIPEA (2.2 mmol) in DMF or THF (2 mL). The mixture was stirred at RT and allowed to stand. After 5 minutes, the relevant amine or amine hydrochloride (1.1 mmol) was added. (In some cases, 0.9 mmol of amine or amine hydrochloride was used.) When the amine hydrochloride was used, DBU (1.5 mmol) was added at this stage. After 10 minutes, the mixture was diluted with EtOAc or DCM (30 mL) and washed with either HCl (1 M, 20 mL) or saturated sodium bicarbonate solution (20 mL) or water (20 mL). In some cases, the aqueous phase was further extracted with EtOAc or DCM. The combined organic phases were washed with water (2×20 mL), dried and concentrated. In some cases further purification was carried out, by silica chromatography (typically 0-100% EtOAc/petrol), reverse-phase chromatography on C18 silica (typically eluting with 5-95% MeCN/water) or preparative HPLC.

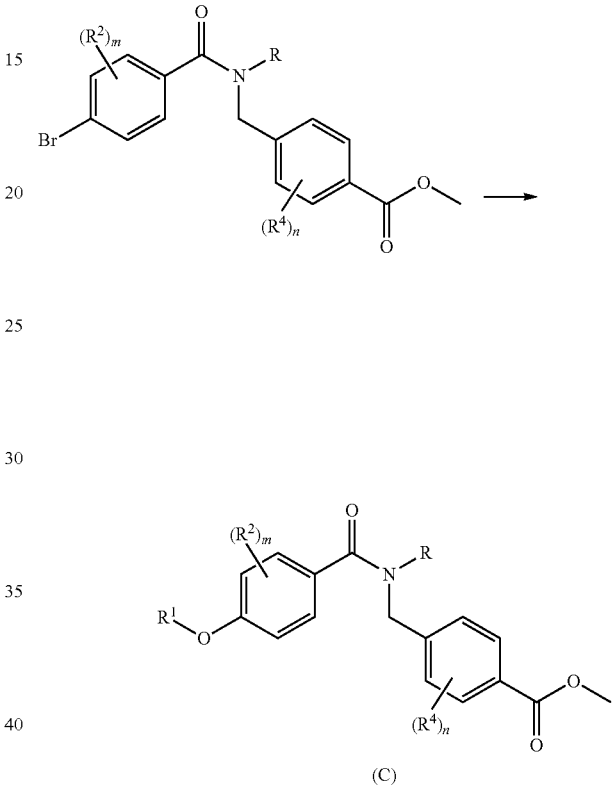

(C)

Method E5

Step (i) Triethylamine (1.351 mL, 9.69 mmol) was added slowly to a mixture of 4-bromobenzoyl chloride (0.851 g, 3.88 mmol) and methyl 4-((phenethylamino)methyl)-benzoate (Intermediate B14) (0.870 g, 3.23 mmol) in DCM (20 mL) at RT under nitrogen and the mixture stirred for 18 h. The mixture was diluted with DCM (30 mL), water (10 mL) and HCl (2 M, 10 mL), and the phases separated. The aqueous phase was extracted with DCM (30 mL) and the combined organic phases washed with water (10 mL), dried and concentrated. The residue was purified by silica chromatography (0-50% EtOAc/petrol) to give methyl 4-((4-bromo-N-phenethylbenzamido)methyl)benzoate (1.21 g, 83%) as a pale orange oil.

MS ES$^+$: 452, 454

Step (ii) Tripotassium phosphate (2 mmol), palladium(II) acetate (0.1 mmol) and di-tert-butyl(2',4',6'-triisopropylbiphenyl-2-yl)phosphine (0.15 mmol) were added to a solution of methyl 4-((4-bromo-N-phenethylbenzamido)methyl) benzoate (step (i) above) (1 mmol) and the relevant phenol (1.2 mmol) in toluene (5 mL). The mixture was degassed for about 5 minutes, purged with nitrogen and heated either thermally or under microwave irradiation at 120° C. for 20h. The mixture was filtered through diatomaceous earth, washing through with EtOAc. The filtrate was concentrated and purified either by silica chromatography (typically 0-100% EtOAc/petrol) or preparative HPLC.

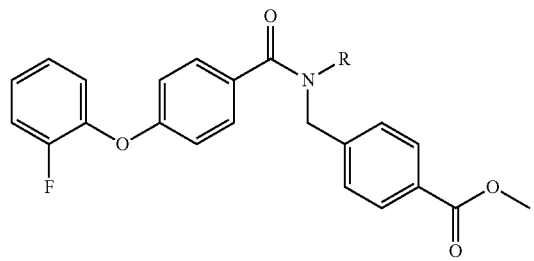

TABLE 2

| Intermediate | R | Product | Method | Data |
|---|---|---|---|---|
| C6 | $CH_2CH_3$ | methyl 4-((N-ethyl-4-(2-fluorophenoxy)benzamido)methyl)benzoate | E2 | MS ES$^+$: 408 |
| C7 | $CH_2CHF_2$ | methyl 4-((N-(2,2-difluoroethyl)-4-(2-fluorophenoxy)benzamido)methyl)benzoate | E2 | MS ES$^+$: 444 |
| C8 | $CH_2CF_3$ | methyl 4-((4-(2-fluorophenoxy)-N-(2,2,2-trifluoroethyl)benzamido)methyl)benzoate | E3 | MS ES$^+$: 462 |
| C9 | $CH_7iPr$ | methyl 4-((4-(2-fluorophenoxy)-N-isobutylbenzamido)methyl)benzoate | E1 | MS ES$^+$: 436 |
| C10 | cyclopropylmethyl | methyl 4-((N-(cyclopropylmethyl)-4-(2-fluorophenoxy)benzamido)methyl)benzoate | E1 | MS ES$^+$: 434 |
| C11 | cyclobutylmethyl | methyl 4-((N-(cyolobutylmethyl)-4-(2-fluorophenoxy)benzamido)methyl)benzoate | E4 | MS ES$^+$: 448 |
| C12 | isopentyl | methyl 4((4-(2-fluorophenoxy)-N-isopentylbenzamido)methyl)benzoate | E1 | MS ES$^+$: 450 |
| C13 | 2-cyclopropylethyl | methyl 4-((N-(2-cyclopropylethyl)-4-(2-fluorophenoxy)benzamido)methyl)benzoate | E1 | MS ES$^+$: 448 |
| C14 | 2-cyclobutylethyl | methyl 4-((N-(2-cyclobutylethyl)-4-(2-fluorophenoxy)benzamido)methyl)benzoate | E1 | MS ES$^+$: 462 |
| C15 | benzyl | methyl 4-((N-benzyl-4-(2-fluorophenoxy)benzamido)methyl)benzoate | E1 | MS ES$^+$: 470 |
| C16 | 2-fluorobenzyl | methyl 4-((N-(2-fluorobenzyl)-4-(2-fluorophenoxy)benzamido)methyl)benzoate | E4 | MS ES$^+$: 488 |
| C17 | 3-methoxybenzyl | methyl 4-((4-(2-fluorophenoxy)-N-(3-methoxybenzyl)benzamido)methyl)benzoate | E4 | n/a |

TABLE 2-continued

| Intermediate | R | Product | Method | Data |
|---|---|---|---|---|
| C18 | 4-methoxybenzyl group | methyl 4-((4-(2-fluorophenoxy)-N-(4-methoxybenzyl)benzamido)methyl)benzoate | E4 | n/a |
| C19 | phenethyl | methyl 4-((4-(2-fluorophenoxy)-N-phenethylbenzamido)methyl)benzoate | E4 | MS ES+: 484 |
| C20 | 3-(2-fluorophenyl)propyl | methyl 4-((4-(2-fluorophenoxy)-N-(3-(2-fluorophenyl)propyl)benzamido)methyl)benzoate | E4 | MS ES+: 516 |
| C21 | 3-(3-fluorophenyl)propyl | methyl 4-((4-(2-fluorophenoxy)-N-(3-(3-fluorophenyl)propyl)benzamido)methyl)benzoate | E4 | MS ES+: 516 |
| C22 | (trans-2-phenylcyclopropyl)methyl | methyl 4-((4-(2-fluorophenoxy)-N-((trans-2-phenylcyclopropyl)methyl)benzamido)-methyl)benzoate | E4 | MS ES+: 510 |
| C23 | (S)-2-hydroxy-3-phenylpropyl | (S)-methyl 4-((4-(2-fluorophenoxy)-N-(2-hydroxy-3-phenylpropyl)benzamido)methyl)benzoate | E4 | MS ES+: 514 |
| C24 | (R)-2-hydroxy-3-phenylpropyl | (R)-methyl 4-((4-(2-fluorophenoxy)-N-(2-hydroxy-3-phenylpropyl)benzamido)methyphenzoate | E4 | MS ES+: 514 |
| C25 | 4-phenylbutyl | methyl 4-((4-(2-fluorophenoxy)-N-(4-phenylbutyl)benzamido)methyl)benzoate | E2 | MS ES+: 512 |
| C25a | $CH_2CH_2CH_3$ | methyl 4-((4-(2-fluorophenoxy)-N-propylbenzamido)-methyl)benzoate | E4 | MS ES+: 422 |
| C25b | $CH_2CH_2CF_3$ | methyl 4-((4-(2-fluorophenoxy)-N-(3,3,3-trifluoropropyl)benzamido)methyl)benzoate | E4 | MS ES+: n/a |
| C25c | $CH_2CF_2CH_3$ | methyl 4-((N-(2,2-difluoropropyl)-4-(2-fluorophenoxy)benzamido)methyl)benzoate | E3 | MS ES+: n/a |
| C25d | butyl | methyl 4-((N-butyl-4-(2-fluorophenoxy)benzamido)methyl)benzoate | E4 | MS ES+: 436 |

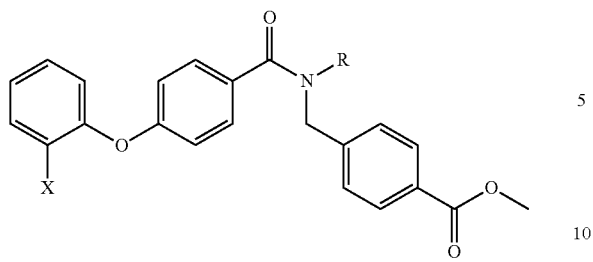

TABLE 3

| Intermediate | X | R | Product | Method | Data |
|---|---|---|---|---|---|
| C26 | Me | cyclopropylmethyl | methyl 4-((N-(cyclopropylmethyl)-4-(o-tolyloxy)benzamido)methyl)benzoate | E4 | MS ES+: 430 |
| C27 | Me | cyclobutylmethyl | methyl 4-((N-(cyclobutylmethyl)-4-(o-tolyloxy)benzamido)methyl)benzoate | E4 | MS ES+: 444 |
| C28 | Me | benzyl | methyl 4-((N-benzyl-4-(o-tolyloxy)benzamido)methyl)benzoate | E4 | MS ES+: 466 |
| C29 | Me | phenethyl | methyl 4-((N-phenethyl-4-(o-tolyloxy)benzamido)methyl)benzoate | E3 | MS ES+: 480 |
| C30 | $CF_3$ | phenethyl | methyl 4-((N-phenethyl-4-(2-(trifluoromethyl)phenoxy)benzamido)methyl)benzoate | E5 | MS ES+: 534 |
| C31 | CN | benzyl | methyl 4-((N-benzyl-4-(2-cyanophenoxy)benzamido)methyl)benzoate | E4 | MS ES+: 477 |
| C32 | OMe | $CH_2CH_3$ | methyl 4-((N-ethyl-4-(2-methoxyphenoxy)benzamido)methyl)benzoate | E2 | MS ES+: 420 |
| C33 | OMe | $CH_2CHF_2$ | methyl 4-((N-(2,2-difluoroethyl)-4-(2-methoxyphenoxy)benzamido)methyl)benzoate | E2 | MS ES+: 456 |
| C34 | OMe | $CH_2iPr$ | methyl 4-((N-isobutyl-4-(2-methoxyphenoxy)benzamido)methyl)benzoate | E4 | MS ES+: 448 |
| C35 | OMe | cyclopropylmethyl | methyl 4-((N-(cyclopropylmethyl)-4-(2-methoxyphenoxy)benzamido)methyl)benzoate | E4 | MS ES+: 446 |

TABLE 3-continued

| Inter-mediate | X | R | Product | Method | Data |
|---|---|---|---|---|---|
| C36 | OMe | 3-phenylpropyl | methyl 4-((4-(2-methoxyphenoxy)-N-(3-phenylpropyl)benzamido)-methyl)benzoate | E1 | MS ES+: 510 |
| C37 | OMe | 3-(3-fluorophenyl)propyl | methyl 4-((N-(3-(3-fluorophenyl)propyl)-4-(2-methoxyphenoxy)benzamido)methyl)-benzoate | E1 | MS ES+: 528 |
| C38 | OEt | cyclopropylmethyl | methyl 4-((N-cyclopropylmethyl)-4-(2-ethoxyphenoxy)benzamido)methyl)-benzoate | E5 | MS ES+: 460 |
| C39 | Cl | cyclopropylmethyl | methyl 4-((4-(2-chlorophenoxy)-N-(cyclopropylmethyl)benzamide)-methyl)benzoate | E4 | MS ES+: 450 |
| C40 | Cl | phenethyl | methyl 4-((4-(2-chlorophenoxy)-N-phenethylbenzamido)methyl)benzoate | E5 | MS ES+: 500 |
| C40a | OMe | CH$_2$CF$_3$ | methyl 4-((4-(2-methoxyphenoxy)-N-(2,2,2-trifluoroethyl)benzamido)-methyl)benzoate | E3 | MS ES+: n/a |
| C40b | OMe | CH$_2$CH$_2$CH$_3$ | methyl 4-((4-2-methoxyphenoxy)-N-propylbenzamido)methyl)benzoate | E4 | MS ES+: n/a |
| C40c | OMe | CH$_2$CF$_2$CH$_3$ | methyl 4-((N-(2,2-difluoropropyl)-4-(2-methoxyphenoxy)benzamido)methyl)-benzoate | E3 | MS ES+: n/a |
| C40d | OMe | CH$_2$CH$_2$CF$_3$ | methyl 4-((N-(3,3,3-trifluoropropyl)-4-(2-methoxyphenoxy)benzamido)-methyl)benzoate | E4 | MS ES+: 488 |
| C40e | OMe | butyl | methyl 4-((N-butyl-4-(2-methoxyphenoxy)benzamido)methyl)-benzoate | E4 | MS ES+: n/a |
| C40f | Me | CH$_2$CF$_3$ | methyl 4-((4-(o-tolyloxy)-N-(2,2,2-trifluoroethyl)benzamido)methyl)-benzoate | E3 | MS ES+: n/a |
| C40g | Cl | CH$_2$CF$_3$ | methyl 4-((4-(2-chlorophenoxy)-N-(2,2,2-trifluoroethyl)benzamido)-methyl)benzoate | E3 | MS ES+: n/a |
| C40h | Me | CH$_2$CH$_3$ | methyl 4-((N-ethyl-4-(o-tolyloxy)benzamido)methyl)benzoate | E4 | MS ES+: n/a |
| C40i | Cl | CH$_2$CH$_3$ | methyl 4-((4-(2-chlorophenoxy)-N-ethylbenzamido)methyl)benzoate | E4 | MS ES+: n/a |
| C40j | Cl | CH$_2$CHF$_2$ | methyl 4-((4-(2-chlorophenoxy)-N-(2,2-difluoroethyl)benzamido)methyl)-benzoate | E3 | MS ES+: n/a |

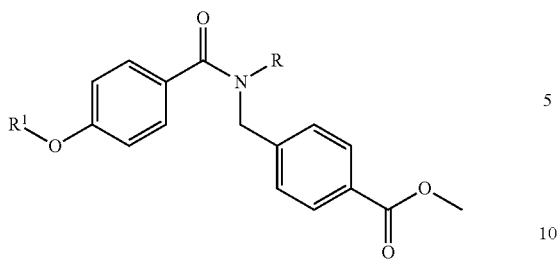

TABLE 4

| Intermediate | R¹ | R | Product | Method | Data |
|---|---|---|---|---|---|
| C41 | 2,6-difluorophenyl | cyclopropylmethyl | methyl 4-((N-(cyclopropylmethyl)-4-(2,6-difluorophenoxy)-benzamido)methyl)benzoate | E1 | MS ES⁺: 452 |
| C42 | 2,6-difluorophenyl | 2-cyclopropylethyl | methyl 4-((N-(2-cyclopropylethyl)-4-(2,6-difluorophenoxy)-benzamido)methyl)benzoate | E1 | MS ES⁺: 466 |
| C43 | 2,6-difluorophenyl | benzyl | methyl 4-((N-benzyl-4-(2,6-difluorophenoxy)benzamido)-methyl)benzoate | E1 | MS ES⁺: 488 |
| C44 | 2-fluoro-6-methylphenyl | cyclopropylmethyl | methyl 4-((N-(cyclopropylmethyl)-4-(2-fluoro-6-methylphenoxy)benzamido)-methyl)benzoate | E4 | MS ES⁺: 448 |
| C45 | 2-fluoro-6-methylphenyl | cyclobutylmethyl | methyl 4-((N-(cyclopropylmethyl)-4-(2-fluoro-6-methylphenoxy)-benzamido)methyl)benzoate | E4 | MS ES⁺: 462 |
| C46 | 2-chloro-6-fluorophenyl | cyclopropylmethyl | methyl 4-((4-(2-chloro-6-fluorophenoxy)-N-(cyclopropylmethyl)benzamido)-methyl)benzoate | E1 | MS ES⁺: 468 |
| C47 | 2-chloro-6-fluorophenyl | 2-cyclopropylethyl | methyl 4-((4-(2-chloro-6-fluorophenoxy)-N-(2-(cyclopropylmethyl)benzamido)-methyl)benzoate | E1 | MS ES⁺: 482 |

TABLE 4-continued

| Intermediate | R¹ | R | Product | Method | Data |
|---|---|---|---|---|---|
| C48 | 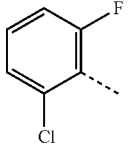 | 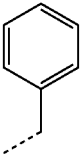 | methyl 4-((N-benzyl-4-(2-chloro-6-fluorophenoxy)benzamido)methyl)-benzoate | E1 | MS ES$^+$: 504 |
| C49 | 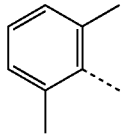 | 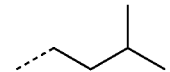 | methyl 4-((4-(2,6-dimethylphenoxy)-N-isopentylbenzamido)methyl)-benzoate | E4 | MS ES$^+$: 460 |
| C50 | 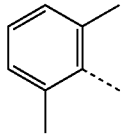 | 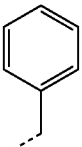 | methyl 4-((N-benzyl-4-(2,6-dimethylphenoxy)benzamido)-methyl)benzoate | E4 | MS ES$^+$: 480 |
| C51 | 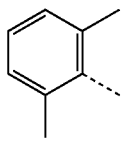 | 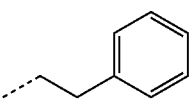 | methyl 4-((4-(2,6-dimethylphenoxy)-N-phenethylbenzamido)methyl)-benzoate | E4 | MS ES$^+$: 494 |
| C52 | 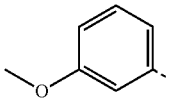 | 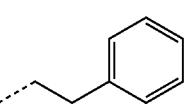 | methyl 4-((4-(3-methoxyphenoxy)-N-phenethylbenzamido)methyl)-benzoate | E5 | MS ES$^+$: 496 |
| C53 | 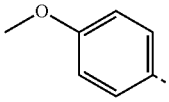 | 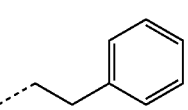 | methyl 4-((4-(4-methoxyphenoxy)-N-phenethylbenzamido)-methyl)benzoate | E5 | MS ES$^+$: 496 |
| C54 | 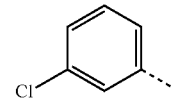 | 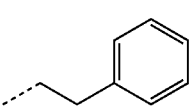 | methyl 4-((4-(3-chlorophenoxy)-N-phenethylbenzamido)methyl)-benzoate | E5 | MS ES$^+$: 500 |
| C55 | 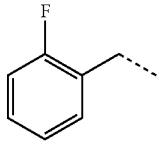 | 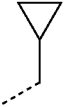 | methyl 4-((N-(cyclopropylmethyl)-4-((2-fluorobenzyl)oxy)benzamido)-methyl)benzoate | E4 | MS ES$^+$: 448 |
| C56 | 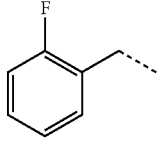 |  | methyl 4-((N-(cyclobutylmethyl)-4-((2-fluorobenzyl)oxy)benzamido)-methyl)benzoate | E4 | MS ES$^+$: 462 |
| C57 | 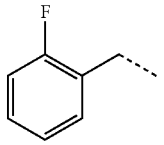 |  | methyl 4-((N-benzyl-4-((2-fluorobenzyl)oxy)benzamido)-methyl)benzoate | E4 | MS ES$^+$: 484 |

Intermediate C58: Methyl 4-((4-(2-fluorophenoxy)-N-((3-methoxycyclobutyl)methyl)benzamido)methyl)benzoate (mixture of cis and trans ring isomers)

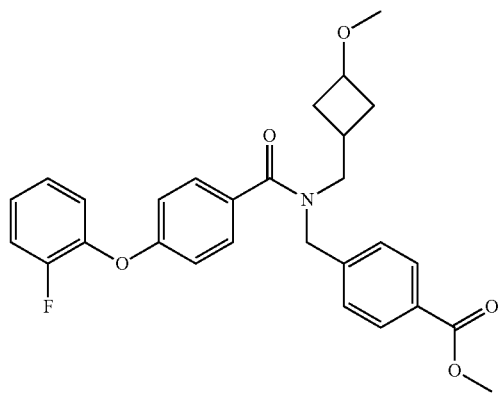 [SMILES: COC(=O)c1ccc(CN(CC2CC(OC)C2)C(=O)c2ccc(Oc3ccccc3F)cc2)cc1]

Step (i) Prepared using the HATU coupling procedure described in Method E4 above from 3-methoxycyclobutanecarboxylic acid (500 mg, 3.84 mmol) and (4-bromophenyl)methanamine hydrochloride (940 mg, 4.23 mmol) to give N-(4-bromobenzyl)-3-methoxycyclobutanecarboxamide (mixture of cis and trans ring isomers) (880 mg, 77%).
MS ES+: 298, 300

Step (ii) Lithium aluminium hydride (1 M solution in THF, 2.62 mL, 2.62 mmol) was added to a solution of N-(4-bromobenzyl)-3-methoxycyclobutanecarboxamide from step (i) above (780 mg, 2.62 mmol) in THF (20 mL) at RT. After stirring for 18 h, the mixture was quenched with saturated sodium sulfate dodecahydrate solution (5 mL), filtered and concentrated. The residue was dissolved in DCM (50 mL) and washed with NaOH (2 M, 50 mL). The organic phase was concentrated and the residue purified by silica chromatography (0-30% EtOAc/petrol) to give N-(4-bromobenzyl)-1-(3-methoxycyclobutyl)methanamine (mixture of cis and trans ring isomers) which was used in the next step without further purification or characterisation.

Step (iii) Prepared using the HATU coupling procedure described in Method E4 above from 4-(2-fluorophenoxy) benzoic acid (Intermediate A1) (310 mg, 1.337 mmol) and N-(4-bromobenzyl)-1-(3-methoxycyclobutyl)methanamine from step (ii) above (380 mg, 1.337 mmol) to give the desired compound, N-(4-bromobenzyl)-4-(2-fluorophenoxy)-N-((3-methoxycyclobutyl)methyl)benzamide (mixture of cis and trans ring isomers), along with the corresponding des-bromo analogue N-benzyl-4-(2-fluorophenoxy)-N-((3-methoxycyclobutyl)methyl)benzamide (also a mixture of cis and trans ring isomers). This material (approximately 1:1 mixture of bromo:des-bromo compound, 684 mg in total) was used in the next step without further purification. MS ES+: 498, 500

Step (iv) A solution of palladium(II) acetate (27.0 mg, 0.120 mmol), 1,3-bis(diphenylphosphino)propane (49.7 mg, 0.120 mmol), and N-(4-bromobenzyl)-4-(2-fluorophenoxy)-N-((3-methoxycyclobutyl)methyl)benzamide from step (iii) above (300 mg, 0.602 mmol) in MeOH (5 mL) and DMF (3 mL) was degassed and purged with nitrogen. Triethylamine (0.168 mL, 1.204 mmol) was added, the reaction mixture was evacuated and carbon monoxide passed through the solution. After stirring under carbon monoxide at 70° C. for 18 h, the mixture was MeOH-evaporated and the residue dissolved in DCM (20 mL). The organic phase was washed with water (20 mL) and concentrated. The resulting residue was purified by silica chromatography (0-30% EtOAc/petrol) to give the title compound (115 mg, 80% based on starting material being 50% pure).
MS ES+: 478

Intermediate C59: Methyl 4-((N-(cyclopropylmethyl)-2-fluoro-4-(2-fluorophenoxy)benzamido)methyl)benzoate

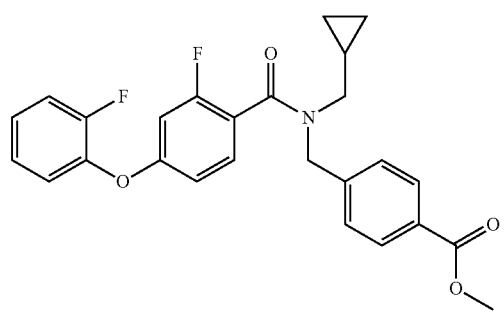 [SMILES: COC(=O)c1ccc(CN(CC2CC2)C(=O)c2ccc(Oc3ccccc3F)cc2F)cc1]

Prepared using the EDC coupling procedure described in Method E1 above from 2-fluoro-4-(2-fluorophenoxy)benzoic acid (Intermediate A6) and methyl 4-((cyclopropylmethylamino)methyl)benzoate hydrochloride (Intermediate B5).
MS ES+: 452

Intermediate C60: Methyl 4-((N-benzyl-4-(2-fluorophenoxy)-cyclohexanecarboxamido)methyl)benzoate (ca. 1:1 mixture of cis and trans ring isomers)

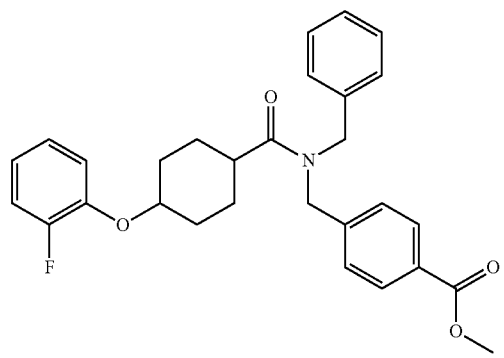 [SMILES: COC(=O)c1ccc(CN(Cc2ccccc2)C(=O)C2CCC(Oc3ccccc3F)CC2)cc1]

Step (i) 4-Toluenesulfonyl chloride (18.29 g, 96 mmol) was added in several portions to a solution of ethyl 4-hydroxycyclohexanecarboxylate (ca. 1:1 mixture of cis and trans ring isomers) (29.5 g, 90 mmol) in pyridine (100 mL) in an ice-water bath, and the mixture stirred, allowing to warm to RT. After the solid had dissolved, the mixture was allowed to stand. After 24 h, the mixture was concentrated and the residue partitioned between water and EtOAc (100 mL each). The organic phase was dried and concentrated to give ethyl 4-(tosyloxy)cyclohexanecarboxylate (ca. 1:1 mixture of cis and trans ring isomers) (crude, 29.5 g) as a colourless oil which was used in the next step without further purification.

¹H NMR (400 MHz, CDCl₃) δ ppm 1.20-1.30 (m, 3H) 1.44-2.08 (m, 8H) 2.21-2.43 (m, 1H) 2.48 (s, 3H) 4.08-4.20 (m, 2H) 4.40-4.50 and 4.70-4.78 (both m, total 1H) 7.28-7.40 (m, 2H) 7.78-7.86 (m, 2H)

Step (ii) 2-Fluorophenol (2.145 mL, 23.25 mmol) was added to a solution/suspension of ethyl 4-(tosyloxy)cyclohexanecarboxylate from step (i) above and cesium carbonate (7.58 g, 23.25 mmol) in DMF (100 mL) and the mixture stirred for 18 h at 80° C. After cooling, the mixture was diluted with EtOAc (200 mL) and washed with saturated sodium hydrogencarbonate solution (100 mL) and brine (100 mL). The organic phase was dried and concentrated, and the residue purified by silica chromatography (0-100%/EtOAc/petrol) to give ethyl 4-(2-fluorophenoxy)cyclohexanecarboxylate (ca. 1:1 mixture of cis and trans ring isomers) (crude, 3.41 g) which was used without further purification or characterisation.

Step (iii) Lithium hydroxide (0.307 g, 12.80 mmol) was added to a solution of ethyl 4-(2-fluorophenoxy)cyclohexanecarboxylate from step (ii) above (crude, 3.41 g) in 1,4-dioxane (30 mL) and water (30 mL), and the mixture heated under microwave irradiation at 100° C. for 15 minutes. The mixture was concentrated. The residue was loaded onto an anion exchange cartridge. After washing with MeCN, the product was eluted with 2 M HCl/MeCN and concentrated to give 4-(2-fluorophenoxy)cyclohexanecarboxylic acid (ca. 1:1 mixture of cis and trans ring isomers) (crude, 1.0 g) as a pale yellow solid which was used in the next step without further purification.

MS ES⁻: 237

Step (iv) The title compound was prepared using the HATU coupling procedure described in Method E4 above, from 4-(2-fluorophenoxy)cyclohexanecarboxylic acid from step (iii) above and methyl 4-((benzylamino)methyl)benzoate hydrochloride (Intermediate B10).

MS ES⁺: 476

Intermediate C61: Methyl 4-((trans-N-benzyl-4-(2-methoxyphenoxy)cyclohexanecarboxamido)methyl)benzoate

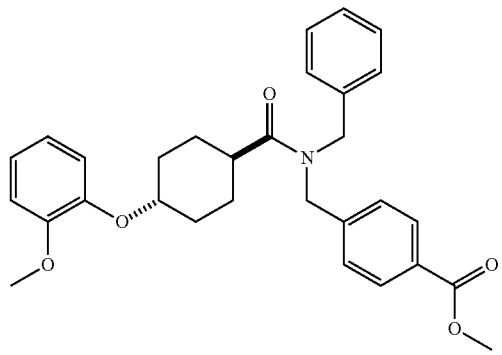

Step (i) A solution of ethyl 4-hydroxycyclohexanecarboxylate (ca. 1:1 mixture of cis and trans ring isomers) (5 g, 29 mmol), 2-methoxyphenol (3.96 g, 31.9 mmol), triphenylphosphine (8.38 g, 31.9 mmol) and trans-diisopropyl diazene-1,2-dicarboxylate (DIAD) (6.21 mL, 31.9 mmol) in THF (150 mL) was stirred at RT. The mixture was diluted with EtOAc (100 mL) and washed with saturated sodium hydrogencarbonate solution (50 mL) and brine (50 mL). The organic phase was dried and concentrated, and the residue purified by silica chromatography (0-100% EtOAc/petrol) to give ethyl 4-(2-methoxyphenoxy)cyclohexanecarboxylate (ca. 1:1 mixture of cis and trans ring isomers) (crude, 4.0 g) which was used without further purification or characterisation.

Step (ii) 4-(2-Methoxyphenoxy)cyclohexanecarboxylic acid was prepared as described for 4-(2-fluorophenoxy)cyclohexanecarboxylic acid (Intermediate C60, step (iii)) using ethyl 4-(2-methoxyphenoxy)cyclohexanecarboxylate from step (i) above.

MS ES⁺: 249

Step (iii) The title compound was prepared using the HATU coupling procedure described in Method E4 above from 4-(2-methoxyphenoxy)cyclohexanecarboxylic acid (step (ii) above) and methyl 4-((benzylamino)methyl)benzoate hydrochloride (Intermediate B10).

MS ES⁺: 488

Intermediate C62: Methyl 4-((cis-N-(3-(3-fluorophenyl)propyl)-4-(2-methoxyphenoxy)cyclohexanecarboxamido)methyl)benzoate and Intermediate C63: Methyl 4-((trans-N-(3-(3-fluorophenyl)propyl)-4-(2-methoxyphenoxy)cyclohexanecarboxamido)methyl)benzoate

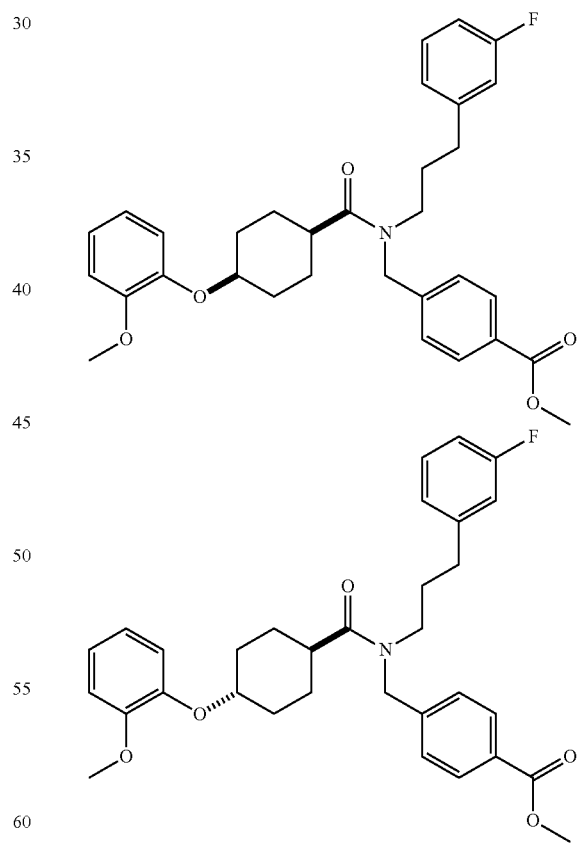

The title compounds were prepared using the HATU coupling procedure described in Method E4 above, from 4-(2-methoxyphenoxy)cyclohexanecarboxylic acid (ca. 1:1 mixture of cis and trans ring isomers) (Intermediate C61, step (ii)) and methyl 4-(((3-(3-fluorophenyl)propyl)amino)

methyl)benzoate hydrochloride (Intermediate B18), and separated by preparative HPLC.

MS ES+: 534 in both cases

Intermediate C64: Methyl 2-fluoro-4-((4-(2-fluorophenoxy)-N-(3-methoxybenzyl)benzamido)methyl)benzoate

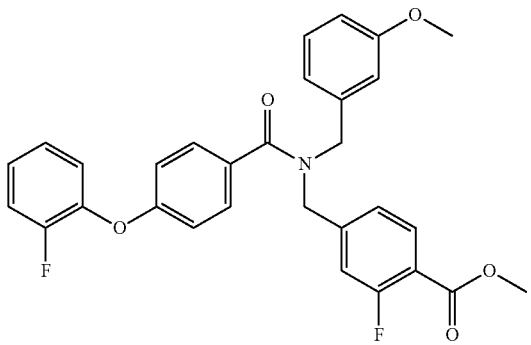 [SMILES: COC(=O)c1ccc(CN(Cc2cccc(OC)c2)C(=O)c2ccc(Oc3ccccc3F)cc2)cc1F]

Step (i) Potassium carbonate (3.70 g, 26.7 mmol) was added to a solution of 4-cyano-2-fluorobenzoic acid (4 g, 24.3 mmol) in DMF (350 mL). After stirring at RT for 15 minutes, iodomethane (1.66 mL, 26.7 mmol) was added. The flask was stoppered, and the mixture stirred at 40° C. for 2 h. The mixture was concentrated under reduced pressure and the residue partitioned between DCM (50 mL) and brine (50 mL). The organic phase was passed through silica and concentrated to give methyl 4-cyano-2-fluorobenzoate (4.1 g, 94%).

$^1$H NMR (300 MHz, CDCl$_3$) δ ppm 3.96 (s, 3H) 7.44-7.48 (m, 1H) 7.49-7.53 (m, 1H) 8.01-8.05 (m, 1H)

Step (ii) Raney nickel (2.0 g) was added to a solution of methyl 4-cyano-2-fluorobenzoate (obtained as described in step (i) above) (10.1 g, 61.6 mmol) in acetic acid (200 mL) and water (100 mL). The mixture was stirred at RT under argon at 20 bar. After 18 h the mixture was filtered through diatomaceous earth, washing through with water (1000 mL). The filtrate was extracted with EtOAc (3×300 mL). The combined organic phases were dried and concentrated, adding toluene to assist removal of acetic acid, to give methyl 2-fluoro-4-(hydroxymethyl)benzoate (crude, 6.06 g) which was used in the next step without further purification or characterisation.

Step (iii) Methyl 2-fluoro-4-(hydroxymethyl)benzoate (step (ii) above) (1 g, 5.4 mmol) was dissolved in chloroform (40 mL) and THF (5 mL). Manganese(IV) oxide (2.36 g, 27 mmol) was added and the mixture stirred at RT for 2 h and then at 60° C. for 1 h. Further manganese(IV) oxide (2.36 g, 27 mmol) was added and heating was continued at 60° C. After 18 h the mixture was filtered through diatomaceous earth to give methyl 2-fluoro-4-formylbenzoate which was used without further purification.

$^1$H NMR (300 MHz, CDCl$_3$) δ ppm 3.95 (s, 3H) 7.58-7.62 (m, 1H) 7.63-7.67 (m, 1H) 8.08-8.12 (m, 1H) 10.04 (s, 1H)

Step (iv) Methyl 2-fluoro-4-(((3-methoxybenzyl)amino) methyl)benzoate was prepared using the reductive amination procedure described in Method R3 above from (3-methoxyphenyl)methanamine and methyl 2-fluoro-4-formylbenzoate (step (iii) above).

MS ES+: 304

Step (v) Oxalyl chloride (0.30 mL, 3.51 mmol) was added to a solution of 4-(2-fluorophenoxy)benzoic acid (Intermediate A) (746 mg, 2.34 mmol) in DCM (10 mL) at RT. DMF (1 drop) was added, and the mixture stirred, allowing to warm to RT. After 2 h, the mixture was concentrated. The residue was dissolved in DCM (5 mL) and added to a solution of methyl 2-fluoro-4-(((3-methoxybenzyl)amino) methyl)benzoate (step (iv) above) (708 mg, 23.4 mmol) and triethylamine (0.49 mL, 3.51 mmol). After 2 h the mixture was partitioned between water (30 mL) and DCM (30 mL). The organic phase was washed sequentially with saturated sodium carbonate solution, citric acid (20% in water) and water, and then dried and concentrated. The residue was purified by silica chromatography (10-30% EtOAc/heptane) to give the title compound which was used in the next step without further purification or characterisation.

Intermediate C65: Methyl 4-((N-(cyclopropylmethyl)-2-fluoro-4-(2-methoxyphenoxy)benzamido) methyl)benzoate

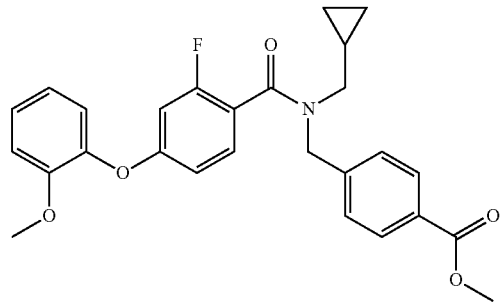 [SMILES: COC(=O)c1ccc(CN(CC2CC2)C(=O)c2ccc(Oc3ccccc3OC)cc2F)cc1]

Prepared using the HATU coupling procedure described in Method E4 above, from 2-fluoro-4-(2-methoxyphenoxy) benzoic acid (Intermediate A8) and methyl 4-(((cyclopropylmethyl)amino)methyl)benzoate hydrochloride (Intermediate B5). In this case, the acid, amine hydrochloride and DIPEA were combined in DMF first, and HATU added last.

MS ES+: 464

Intermediate C65a: Methyl 4-((4-bromo-N-(cyclopropylmethyl)benzamido)methyl)benzoate

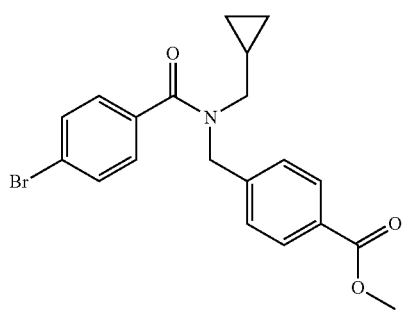 [SMILES: COC(=O)c1ccc(CN(CC2CC2)C(=O)c2ccc(Br)cc2)cc1]

Prepared using a coupling procedure analogous to that described in Method E5 above, from 4-bromobenzoyl chloride and methyl 4-(((cyclopropylmethyl)amino)methyl)benzoate hydrochloride (Intermediate B5).

MS ES+: 402, 404

Intermediate C65b: Methyl 4-((4-bromo-N-propylbenzamido)methyl)benzoate

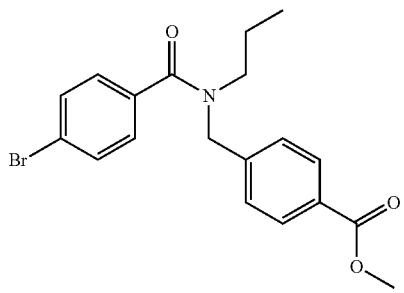 [SMILES: CCCN(Cc1ccc(C(=O)OC)cc1)C(=O)c1ccc(Br)cc1]

Prepared using a coupling procedure analogous to that described in Method E5 above, from 4-bromobenzoyl chloride and methyl 4-((propylamino)methyl)benzoate hydrochloride (Intermediate B19a).

MS ES+: 390, 392

Intermediate C66: Methyl 4-((N-(cyclopropylmethyl)-4-(2-fluoro-6-methoxyphenoxy)benzamido)methyl)benzoate

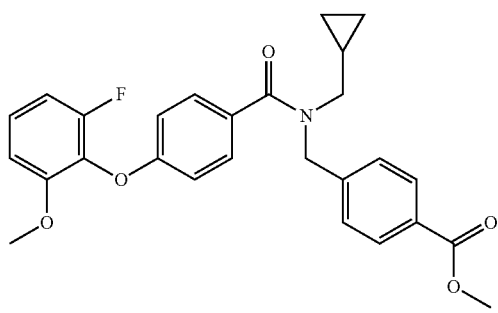 [SMILES: COC(=O)c1ccc(CN(CC2CC2)C(=O)c2ccc(Oc3c(F)cccc3OC)cc2)cc1]

A mixture of methyl 4-((4-bromo-N-(cyclopropylmethyl)benzamido)methyl)benzoate (Intermediate C65a) (300 mg (0.75 mmol), 2-fluoro-6-methoxyphenol (212 mg, 1.49 mmol) and copper(I) oxide (107 mg, 0.75 mmol) in 2,4,6-trimethylpyridine (3 mL) was heated under microwave irradiation at 220° C. for 2 h. Further 2-fluoro-6-methoxyphenol (212 mg, 1.49 mmol) was added, and the mixture heated under microwave irradiation at 220° C. for another 1 h. The mixture was diluted with water and EtOAc (20 mL each) and filtered through diatomaceous earth. The phases were separated. The aqueous phase was acidified to pH ~3 by addition of HCl (2 M) and extracted with EtOAc (3×50 mL). The combined organic phases were dried and concentrated. The residue was purified by silica chromatography (0-60% EtOAc/heptane) to give methyl 4-((N-(cyclopropylmethyl)-4-(2-fluoro-6-methoxyphenoxy)benzamido)methyl)benzoate (90 mg, 26%) as a colourless gum.

$^1$H NMR (400 MHz, CDCl$_3$) δ ppm −0.12-0.31 (m, 2H) 0.38-0.61 (m, 2H) 0.77-1.15 (m, 1H) 2.99-3.50 (m, 2H) 3.90 (s, 3H), 3.79 (s, 3H) 4.59-5.09 (m, 2H) 6.68-7.58 (m, 9H) 7.93-8.10 (m, 2H)

Intermediate C67: Methyl 4-((N-(cyclopropylmethyl)-4-(4-fluoro-2-methoxyphenoxy)benzamido)methyl)benzoate

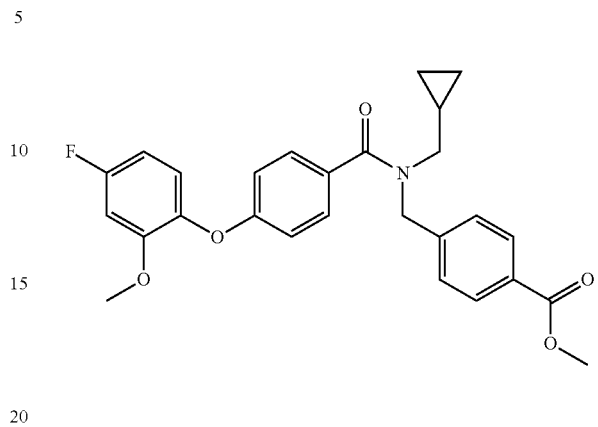

Prepared as described above for Intermediate C66 from methyl 4-((4-bromo-N-(cyclopropylmethyl)benzamido)methyl)benzoate (Intermediate C65a) and 4-fluoro-2-methoxyphenol, except that the mixture was heated under microwave irradiation at 220° C. for 1 h, no additional phenol was required, and slight modifications were made to the workup and purification. In this case the crude reaction mixture was poured into HCl (2 M, 30 mL) and the resulting mixture extracted with EtOAc (3×50 mL). The combined organic phases were washed with a mixture of NaOH (1 M) and brine (ca. 1:1, total 30 mL), dried and concentrated, and the residue was purified by silica chromatography (20-40% EtOAc/heptane).

$^1$H NMR (400 MHz, CDCl$_3$) δ ppm −0.15-0.30 (m, 2H) 0.40-0.59 (m, 2H) 0.78-1.01 (m, 1H) 2.98-3.45 (m, 2H) 3.78 (s, 3H) 3.91 (s, 3H) 4.64-5.05 (m, 2H) 6.58-7.50 (m, 9H) 7.96-8.10 (m, 2H)

Intermediate C67a: Methyl 4-((4-(4-fluoro-2-methoxyphenoxy)-N-propylbenzamido)methyl)benzoate

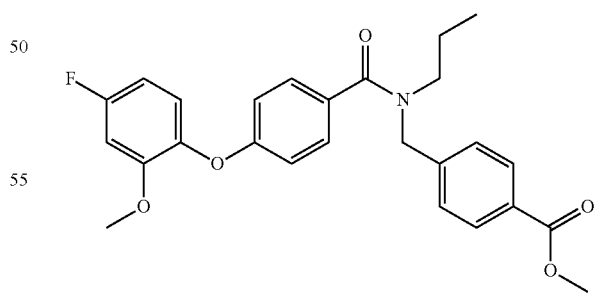

Prepared as described above for Intermediate C66, from methyl 4-((4-bromo-N-propylbenzamido)methyl)benzoate (Intermediate C65b) and 4-fluoro-2-methoxyphenol, except that the mixture was heated thermally at reflux in air for 18 h, the combined organic phases were washed with HCl (1 M), saturated sodium hydrogencarbonate solution and brine (100 mL each), and the residue was purified by silica chromatography (10-20% EtOAc/heptane).

MS ES⁺: 452

Intermediate C67b: Methyl 4-((N-(cyclopropylmethyl)-4-(5-fluoro-2-methoxyphenoxy)benzamido)methyl)benzoate

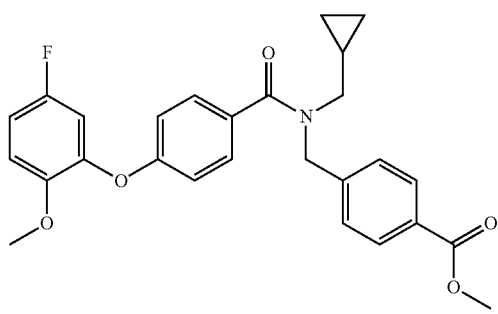 [SMILES: COC(=O)c1ccc(CN(CC2CC2)C(=O)c2ccc(Oc3cc(F)ccc3OC)cc2)cc1]

Prepared as described above for Intermediate C66, from methyl 4-((4-bromo-N-(cyclopropylmethyl)benzamido)methyl)benzoate (Intermediate C65a) and 5-fluoro-2-methoxyphenol, except that the combined organic phases were washed with HCl (1 M), NaOH (2 M) and brine (25 mL each).

$^1$H NMR (400 MHz, CDCl$_3$) δ ppm −0.10-0.30 (m, 2H) 0.34-0.62 (m, 2H) 0.75-1.20 (m, 1H) 3.00-3.60 (m, 2H) 3.78 (s, 3H) 3.91 (s, 3H) 4.70-5.00 (m, 2H) 6.70-7.01 (m, 5H) 7.20-7.50 (m, 4H) 7.96-8.06 (m, 2H)

Intermediate C67c: Methyl 4-((4-(5-fluoro-2-methoxyphenoxy)-N-propylbenzamido)methyl)benzoate

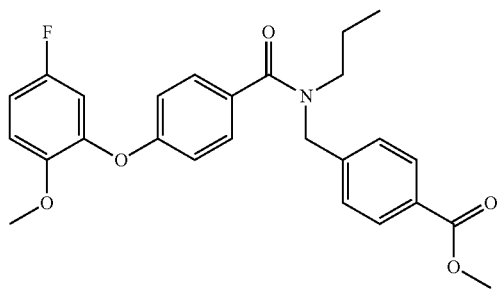 [SMILES: CCCN(Cc1ccc(C(=O)OC)cc1)C(=O)c1ccc(Oc2cc(F)ccc2OC)cc1]

Prepared as described above for Intermediate C66, from methyl 4-((4-bromo-N-propylbenzamido)methyl)benzoate (Intermediate C65b) and 5-fluoro-2-methoxyphenol, except that the mixture was heated under microwave irradiation at 210° C. for 4 h, the combined organic phases were washed with HCl (1 M), saturated sodium hydrogencarbonate solution and brine (50 mL each), the residue was purified by silica chromatography (20-50% EtOAc/heptane), and the material obtained was used in the next step without further purification or characterisation.

Intermediate C67d: Methyl 4-((N-(cyclopropylmethyl)-4-(3-fluoro-2-methoxyphenoxy)benzamido)methyl)benzoate

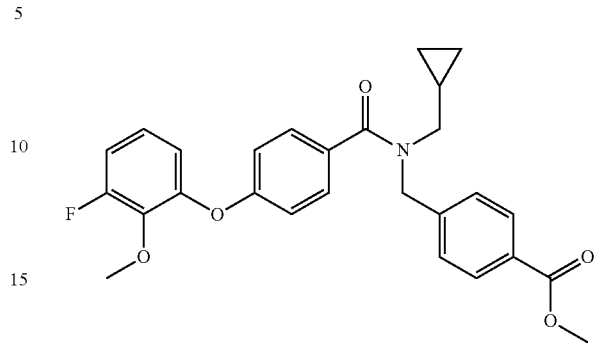

Prepared as described above for Intermediate C66, from methyl 4-((4-bromo-N-(cyclopropylmethyl)benzamido)methyl)benzoate (Intermediate C65a) and 3-fluoro-2-methoxyphenol (prepared as described in Synthetic Communications, 1985, 15(1), 61-69), except that the mixture was heated under microwave irradiation at 210° C. for 5 h, the combined organic phases were washed with HCl (1 M), saturated sodium hydrogencarbonate solution and brine (100 mL each), and the residue was purified by preparative HPLC.

MS ES⁺: 464

Intermediate C67e: Methyl 4-(5-bromo-N-(cyclopropylmethyl)picolinamido)methyl)benzoate

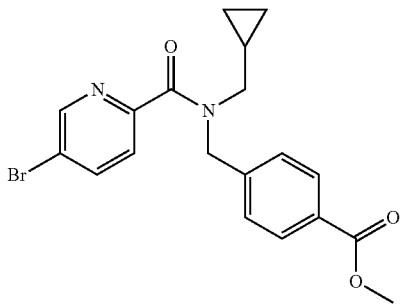 [SMILES: COC(=O)c1ccc(CN(CC2CC2)C(=O)c2ccc(Br)cn2)cc1]

Prepared using the coupling procedure described in Method E4 above, from 5-bromopicolinic acid and methyl 4-(((cyclopropylmethyl)amino)methyl)benzoate hydrochloride (Intermediate B5), using 1.3 eq HATU and 6 eq DIPEA.

MS ES⁺: 403, 405

Intermediate C68: Methyl 4-((N-(cyclopropylmethyl)-5-(2-methoxyphenoxy)picolinamido)methyl)benzoate

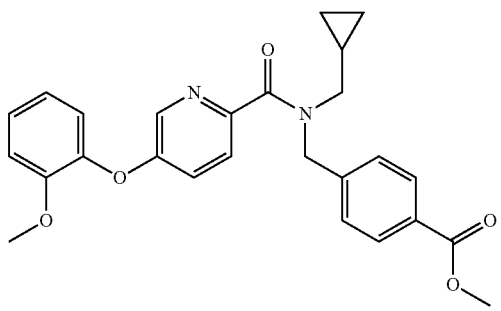 [SMILES: COC(=O)c1ccc(CN(CC2CC2)C(=O)c2ccc(Oc3ccccc3OC)cn2)cc1]

Prepared as described above for Intermediate C66, from methyl 4-((5-bromo-N-(cyclopropylmethyl)picolinamido)methyl)benzoate (Intermediate C67e) and 2-methoxyphenol, except that 5 eq phenol and 2.5 eq copper(I) oxide were used, the mixture was heated thermally at reflux in air for 40 h, the aqueous phase was adjusted to pH ~7, and the residue was purified by silica chromatography (20-40% EtOAc/heptane).

$^1$H NMR (400 MHz, CDCl$_3$) δ ppm −0.10-0.27 (m, 2H) 0.32-0.57 (m, 2H) 0.85-1.35 (m, 1H) 3.27-3.41 (m, 2H) 3.69-3.85 (m, 3H) 3.89 (s, 3H) 4.89-5.05 (m, 2H) 6.87-7.47 (m, 8H) 7.62-7.71 (m, 1H) 7.90-8.06 (m, 2H)

Intermediate C69: Methyl 4-((N-(cyclopropylmethyl)-5-(2-fluorophenoxy)picolinamido)methyl)benzoate

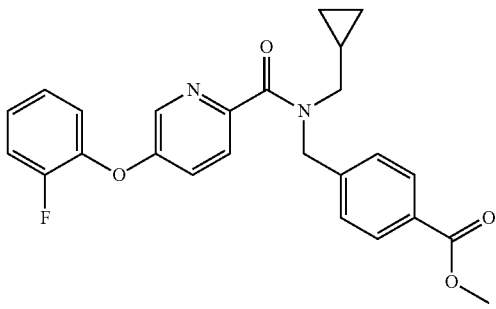 [SMILES: COC(=O)c1ccc(CN(CC2CC2)C(=O)c2ccc(Oc3ccccc3F)cn2)cc1]

Prepared as described above for Intermediate C68, from methyl 4-((5-bromo-N-(cyclopropylmethyl)picolinamido)methyl)benzoate (Intermediate C67e) and 2-fluorophenol, except that 4 eq phenol was used, the mixture was not filtered through diatomaceous earth, and the residue was purified by silica chromatography (40% EtOAc/heptane).

$^1$H NMR (400 MHz, CDCl$_3$) δ ppm −0.50-0.22 (m, 2H) 0.37-0.52 (m, 2H) 0.95-1.10 (m, 1H) 3.28-3.37 (m, 2H) 3.89 (s, 3H) 4.96 (s, 2H) 7.05-7.40 (m, 7H) 7.64-7.74 (m, 1H) 7.91-8.03 (m, 2H), 8.19-8.34 (m, 1H)

Intermediate C70:
5-(2-Fluorophenoxy)pyrimidine-2-carboxylic acid

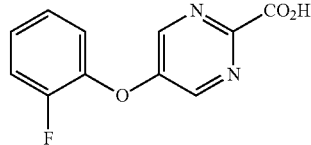 [SMILES: O=C(O)c1ncc(Oc2ccccc2F)cn1]

Step (i) Sodium hydride (60% dispersion in mineral oil, 0.258 g, 6.42 mmol) was added to a solution of 2-fluorophenol (0.492 mL, 5.34 mmol) in pyridine (15 mL) in an ice-water bath. Copper(I) bromide was added, and the mixture heated at 100° C. for 5 h. The mixture was concentrated and the residue triturated with EtOAc and purified by silica chromatography (20% EtOAc/heptane) to give 5-(2-fluorophenoxy)pyrimidine-2-carbonitrile (555 mg, 47%).

$^1$H NMR (400 MHz, CDCl$_3$) δ ppm 7.20-7.40 (m, 4H) 8.46 (s, 2H)

Step (ii) 5-(2-Fluorophenoxy)pyrimidine-2-carbonitrile, NaOH (2 M, 10 mL) and IMS (2 mL) were combined and heated at 70° C. for 18 h. After concentration to remove IMS, HCl (2 M) was added until the pH was 3, and the mixture was extracted with DCM (50 mL). The organic phase was dried and concentrated to give 5-(2-fluorophenoxy)pyrimidine-2-carboxylic acid (250 mg, 48%) as a white solid, which was used in the next step without further purification or characterisation.

Intermediate C71:
5-(2-Methoxyphenoxy)pyrimidine-2-carboxylic acid

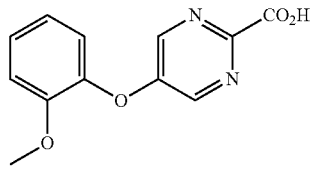 [SMILES: COc1ccccc1Oc1cnc(C(=O)O)nc1]

Step (i) Prepared as for step (i) of Intermediate C70 to give 5-(2-methoxyphenoxy)pyrimidine-2-carbonitrile (555 mg, 47%).

MS ES$^+$: 228

Step (ii) Prepared as for step (ii) of Intermediate C70, from 5-(2-methoxyphenoxy)pyrimidine-2-carbonitrile, to give 5-(2-methoxyphenoxy)pyrimidine-2-carboxylic acid.

$^1$H NMR (400 MHz, CDCl$_3$) δ ppm 3.77 (s, 3H) 7.03-7.07 (m, 2H) 7.15-7.19 (m, 1H) 7.28-7.34 (m, 1H) 8.44 (s, 2H)

Intermediate C72: Methyl 4-((N-(cyclopropylmethyl)-5-(2-fluorophenoxy)pyrimidine-2-carboxamido)methyl)benzoate

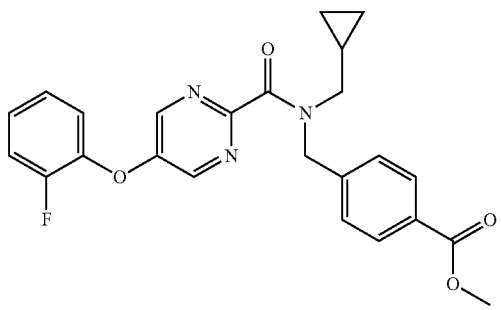 [SMILES: COC(=O)c1ccc(CN(CC2CC2)C(=O)c2ncc(Oc3ccccc3F)cn2)cc1]

Prepared using the coupling procedure described in Method E4 above, from 5-(2-fluorophenoxy)pyrimidine-2-carboxylic acid (Intermediate C70) and methyl 4-(((cyclopropylmethyl)amino)methyl)benzoate hydrochloride (Intermediate B5).

MS ES$^+$: 436

Intermediate C73: Methyl 4-((N-(cyclopropylmethyl)-5-(2-methoxyphenoxy)pyrimidine-2-carboxamido)methyl)benzoate

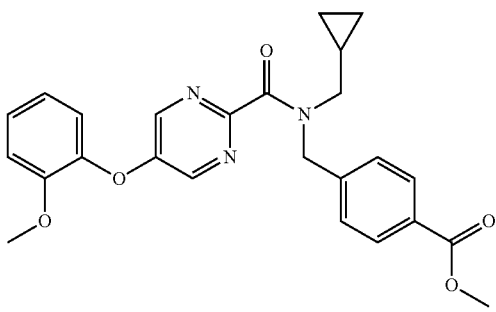 [SMILES: COC(=O)c1ccc(CN(CC2CC2)C(=O)c2ncc(Oc3ccccc3OC)cn2)cc1]

Prepared using the coupling procedure described in Method E4 above, from 5-(2-methoxyphenoxy)pyrimidine-2-carboxylic acid (Intermediate C71) and methyl 4-(((cyclopropylmethyl)amino)methyl)benzoate hydrochloride (Intermediate B5).

MS ES$^+$: 448

Intermediate C74: Methyl 4-((5-(2-methoxyphenoxy)-N-propylpyrimidine-2-carboxamido)methyl)benzoate

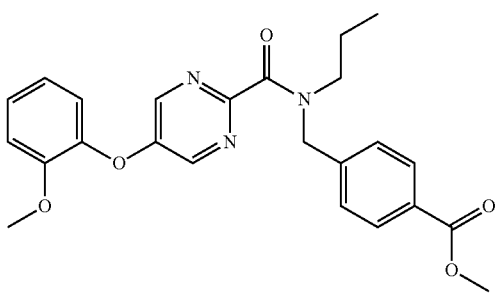 [SMILES: CCCN(Cc1ccc(C(=O)OC)cc1)C(=O)c1ncc(Oc2ccccc2OC)cn1]

Prepared using the coupling procedure described in Method E4 above, from 5-(2-methoxyphenoxy)pyrimidine-2-carboxylic acid (Intermediate C71) and methyl 4-((propylamino)methyl)benzoate hydrochloride (Intermediate B19a).

MS ES$^+$: 436

PREPARATION OF EXAMPLES

Compounds derived from the Intermediates C6 to C74 above were prepared according to Method H1 or H2:

Method H1

Lithium hydroxide or lithium hydroxide monohydrate (5 mmol) was added to a solution of the relevant ester (1 mmol) in water (2 mL) and either THF or 1,4-dioxane (4 mL). In some cases, MeOH was added in addition to THF. The mixture was stirred, typically at RT for 18 h, 50° C. for 4 h or 100° C. for 20 minutes. In some cases the reaction was diluted with NaOH (2 M) and extracted with EtOAc or DCM, and the resulting aqueous phase acidified with HCl (2 M) and extracted with EtOAc. In other cases the crude mixture was partitioned between HCl (2 M) and EtOAc. The combined organic phases from the extraction of the acidic aqueous phase were dried and concentrated. In some cases the residue was loaded onto an anion exchange cartridge. After washing with MeCN, the product was eluted with 1 M HCl/MeCN then concentrated. In some cases the material obtained was purified by reverse-phase chromatography on C18 silica (typically eluted with 5-95% MeOH/H$_2$O with 0.1% NH$_4$OH). In some cases the crude product was heated under reflux in HCl (4 M), allowed to cool and filtered. In some cases the final product was recrystallised, typically using one or more of the following: water, EtOH, EtOAc, methyl acetate, methyl tert-butyl ether, pentane, heptane.

Method H2

Sodium hydroxide (2 M, 6 mmol) was added to a solution of the relevant ester (2 mmol) in THF (3 mL). In some cases, MeOH was added instead of or in addition to THF. The mixture was stirred at RT for 18 h or heated under microwave irradiation at 100° C. for 5 minutes. The mixture was partitioned between HCl (1 M) and EtOAc (30 mL each). The organic phases were dried and concentrated. The residue was loaded onto an anion exchange cartridge. After washing with MeCN, the product was eluted with 4 M HCl/1,4-dioxane then concentrated.

Example 1

4-((N-Ethyl-4-(2-fluorophenoxy)benzamido)methyl)benzoic acid

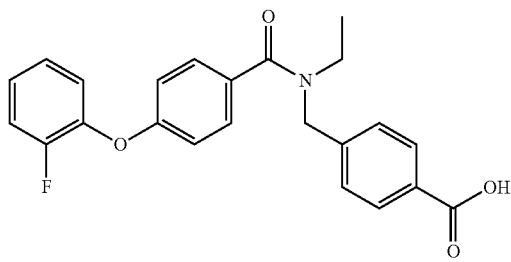 [SMILES: CCN(Cc1ccc(C(=O)O)cc1)C(=O)c1ccc(Oc2ccccc2F)cc1]

Prepared from the parent methyl ester (Intermediate C6) using Method H1.

$^1$H NMR (300 MHz, DMSO-d$_6$) δ ppm 0.84-1.36 (m, 3H) 3.05-3.64 (m, 2H) 4.67 (br s, 2H) 6.73-7.09 (m, 2H) 7.09-7.61 (m, 8H) 7.74-8.05 (m, 2H) 12.90 (br s, 1H)

MS ES$^+$: 394

Example 2

4-((N-(2,2-Difluoroethyl)-4-(2-fluorophenoxy)benzamido)-methyl)benzoic acid

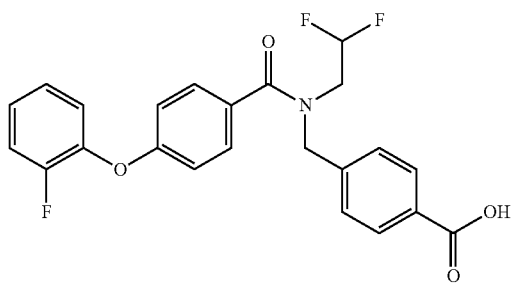 [SMILES: O=C(O)c1ccc(CN(CC(F)F)C(=O)c2ccc(Oc3ccccc3F)cc2)cc1]

Prepared from the parent methyl ester (Intermediate C7) using Method H1.

¹H NMR (300 MHz, DMSO-d$_6$) δ ppm 3.57-3.91 (m, 2H) 4.71 (br s, 2H) 5.95-6.52 (m, 1H) 6.82-7.08 (m, 2H) 7.10-7.57 (m, 8H) 7.79-7.98 (m, 2H) 12.93 (br s, 1H)

MS ES$^+$: 430

Example 3

4-((4-(2-Fluorophenoxy)-N-(2,2,2-trifluoroethyl)benzamido)-methyl)benzoic acid

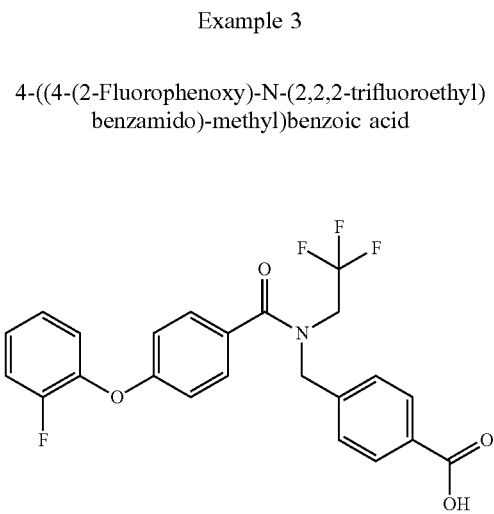

Prepared from the parent methyl ester (Intermediate C8) using Method H1.

¹H NMR (400 MHz, DMSO-d$_6$) δ ppm 4.14-4.36 (m, 2-1) 4.76 (s, 2H) 6.92-7.10 (m, 2H) 7.16-7.37 (m, 5H) 7.39-7.55 (m, 3H) 7.84-7.99 (m, 2H) 12.94 (br s, 1H)

MS ES$^+$: 448

Example 4

4-((4-(2-Fluorophenoxy)-N-isobutylbenzamido)methyl)benzoic acid

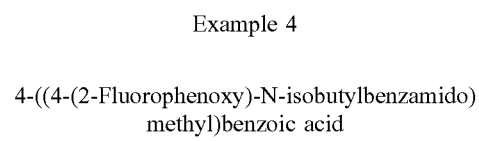

Prepared from the parent methyl ester (Intermediate C9) using Method H1.

¹H NMR (400 MHz, DMSO-d$_6$) δ ppm 0.50-1.08 (m, 6H) 1.77-2.17 (m, 1H) 3.00-3.25 (m, 2H) 4.49-4.86 (m, 2H) 6.88-7.13 (m, 2H) 7.13-7.57 (m, 8H) 7.83-8.04 (m, 2H) 12.69-13.02 (m, 1H)

MS ES$^+$: 422

Example 5

4-((N-(Cyclopropylmethyl)-4-(2-fluorophenoxy)benzamido)-methyl)benzoic acid

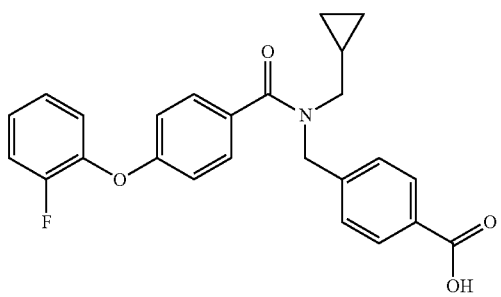 [SMILES: O=C(O)c1ccc(CN(CC2CC2)C(=O)c2ccc(Oc3ccccc3F)cc2)cc1]

Prepared from the parent methyl ester (Intermediate C10) using Method H1.

¹H NMR (400 MHz, DMSO-d$_6$) δ ppm −0.13-0.26 (m, 2H) 0.30-0.50 (m, 2H) 0.75-1.06 (m, 1H) 2.97-3.22 (m, 2H) 4.79 (br s, 2H) 6.88-7.12 (m, 2H) 7.12-7.55 (m, 8H) 7.86-7.97 (m, 2H) 12.87 (br s, 1H)

MS ES$^+$: 420

Example 6

4-((N-(Cyclobutylmethyl)-4-(2-fluorophenoxy)benzamido)-methyl)benzoic acid

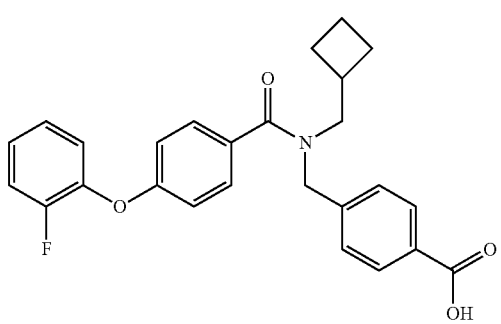 [SMILES: O=C(O)c1ccc(CN(CC2CCC2)C(=O)c2ccc(Oc3ccccc3F)cc2)cc1]

Prepared from the parent methyl ester (Intermediate C11) using Method H1.

¹H NMR (400 MHz, CD$_3$OD) δ ppm 1.37-2.15 (m, 6H) 2.49-2.82 (m, 1H) 3.34-3.58 (m, 2H) 4.60-4.78 (m, 2H) 6.90-7.04 (m, 2H) 7.14-7.29 (m, 5H) 7.33-7.49 (m, 3H) 7.82-8.03 (m, 2H)

MS ES$^+$: 434

Example 7

4-((4-(2-Fluorophenoxy)-N-((3-methoxycyclobutyl)methyl)-benzamido)methyl)benzoic acid (mixture of cis and trans ring isomers)

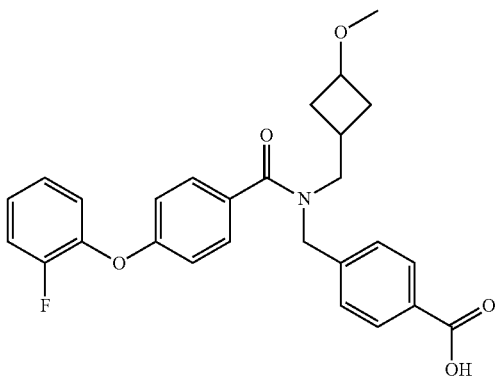 [SMILES: COC1CC(CN(Cc2ccc(C(=O)O)cc2)C(=O)c2ccc(Oc3ccccc3F)cc2)C1]

Prepared from the parent methyl ester (Intermediate C58) using Method H1.

$^1$H NMR (400 MHz, DMSO-d$_6$) δ ppm 1.64-2.30 (m, 4H) 3.04 (br s, 3H) 3.16-3.70 (m, 4H) 4.65 (br s, 2H) 6.85-7.14 (m, 2H) 7.14-7.59 (m, 8H) 7.82-8.00 (m, 2H)

MS ES$^+$: 464

Example 8

4-((4-(2-Fluorophenoxy)-N-isopentylbenzamido)methyl)benzoic acid

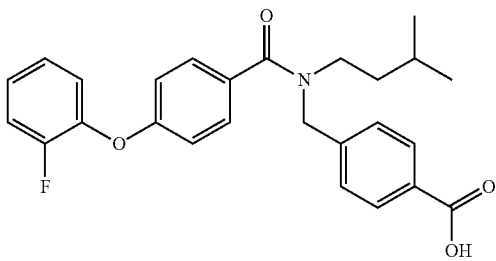 [SMILES: CC(C)CCN(Cc1ccc(C(=O)O)cc1)C(=O)c1ccc(Oc2ccccc2F)cc1]

Prepared from the parent methyl ester (Intermediate C12) using Method H1.

$^1$H NMR (400 MHz, DMSO-d$_6$) δ ppm 0.48-1.00 (m, 6H) 1.39 (br s, 3H) 3.21 (br s, 2H) 4.49-4.84 (m, 2H) 7.01 (br s, 2H) 7.17-7.57 (m, 8H) 7.88-7.97 (m, 2H) 12.90 (br s, 1H)

MS ES$^+$: 436

Example 9

4-((N-(2-Cyclopropylethyl)-4-(2-fluorophenoxy)benzamido)-methyl)benzoic acid

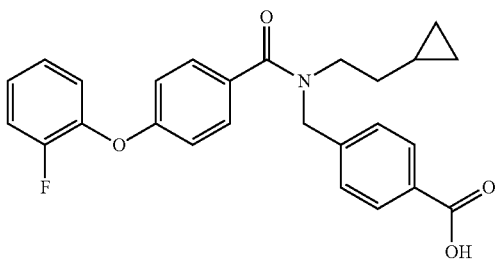 [SMILES: O=C(O)c1ccc(CN(CCC2CC2)C(=O)c2ccc(Oc3ccccc3F)cc2)cc1]

Prepared from the parent methyl ester (Intermediate C13) using Method H1.

$^1$H NMR (400 MHz, CD$_3$OD) δ ppm −0.22-0.17 (m, 2H) 0.26-0.51 (m, 2H) 0.52-0.79 (m, 1H) 1.35-1.64 (m, 2H) 3.35-3.63 (m, 2H) 4.58-4.79 (m, 2H) 6.90-7.08 (m, 2H) 7.13-7.34 (m, 5H) 7.37-7.54 (m, 3H) 8.06-8.22 (m 2H)

MS ES$^+$: 434

Example 10

4-((N-(2-Cyclobutylethyl)-4-(2-fluorophenoxy)benzamido)-methyl)benzoic acid

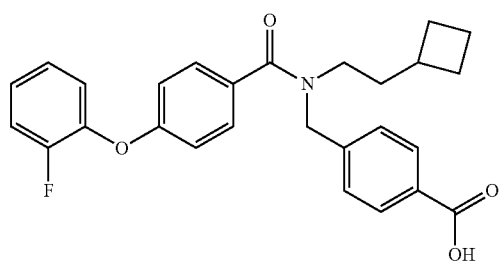 [SMILES: O=C(O)c1ccc(CN(CCC2CCC2)C(=O)c2ccc(Oc3ccccc3F)cc2)cc1]

Prepared from the parent methyl ester (Intermediate C14) using Method H1.

$^1$H NMR (400 MHz, DMSO-d$_6$) δ ppm 1.24-2.30 (m, 9H) 2.88-3.40 (m, 2H) 4.48-4.82 (m, 2H) 7.01 (br s, 2H) 7.19-7.54 (m, 8H) 7.88-7.96 (m, 2H) 12.90 (br s, 1H)

MS ES$^+$: 448

Example 11

4-((N-Benzyl-4-(2-fluorophenoxy)benzamido)methyl)benzoic acid

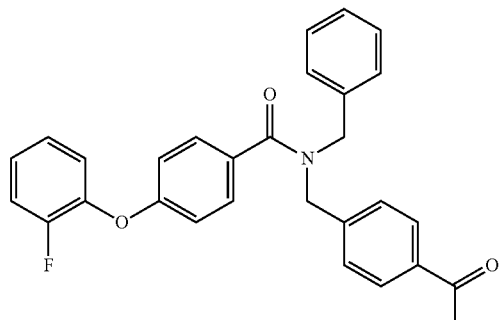

Prepared from the parent methyl ester (Intermediate C15) using Method H1.

$^1$H NMR (400 MHz, DMSO-d$_6$) δ ppm 4.37-4.80 (m, 4H) 6.92-7.06 (m, 2H) 7.11-7.60 (m, 13H) 7.85-7.99 (m, 2H)

MS ES$^+$: 456

Example 12

4-((N-(2-Fluorobenzyl)-4-(2-fluorophenoxy)benzamido)-methyl)benzoic acid

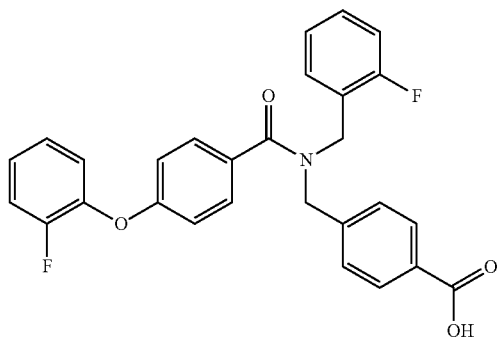 [SMILES: O=C(O)c1ccc(CN(Cc2ccccc2F)C(=O)c2ccc(Oc3ccccc3F)cc2)cc1]

Prepared from the parent methyl ester (Intermediate C16) using Method H1.

$^1$H NMR (400 MHz, DMSO-d$_6$) δ ppm 4.45-4.66 (m, 4H) 6.96-7.03 (m, 2H) 7.03-7.45 (m, 10H) 7.45-7.54 (m, 2H) 7.78-7.89 (m, 2H)

MS ES$^+$: 474

Example 13

4-((4-(2-Fluorophenoxy)-N-(3-methoxybenzyl)benzamido)-methyl)benzoic acid

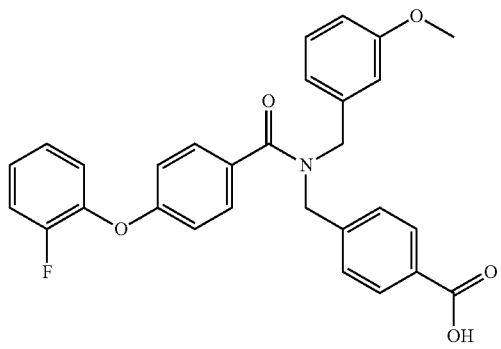 [SMILES: COc1cccc(CN(Cc2ccc(C(=O)O)cc2)C(=O)c2ccc(Oc3ccccc3F)cc2)c1]

Prepared from the parent methyl ester (Intermediate C17) using Method H1.

$^1$H NMR (400 MHz, DMSO-d$_6$) δ ppm 3.72 (s, 3H) 4.42-4.71 (m, 4H) 6.55-7.10 (m, 5H) 7.16-7.62 (m, 9H) 7.76-7.99 (m, 2H) 12.92 (br s, 1H)

MS ES$^+$: 486

Example 14

4-((4-(2-Fluorophenoxy)-N-(4-methoxybenzyl)benzamido)-methyl)benzoic acid

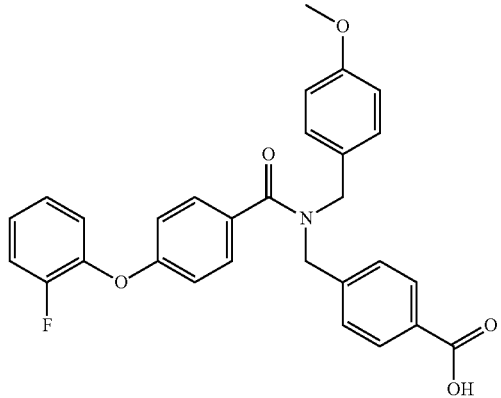 [SMILES: COc1ccc(CN(Cc2ccc(C(=O)O)cc2)C(=O)c2ccc(Oc3ccccc3F)cc2)cc1]

Prepared from the parent methyl ester (Intermediate C18) using Method H1.

$^1$H NMR (400 MHz, DMSO-d$_6$) δ ppm 3.74 (s, 3H) 4.24-4.80 (m, 4H) 6.83-7.65 (m, 14H) 7.84-8.05 (m, 2H) 12.90 (br s, 1H)

MS ES$^+$: 486

Example 15

4-((4-(2-Fluorophenoxy)-N-phenethylbenzamido)methyl)benzoic acid

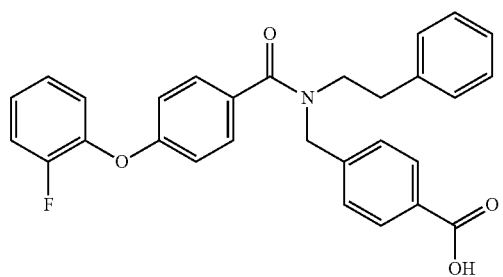 [SMILES: O=C(O)c1ccc(CN(CCc2ccccc2)C(=O)c2ccc(Oc3ccccc3F)cc2)cc1]

Prepared from the parent methyl ester (Intermediate C19) using Method H1.

$^1$H NMR (400 MHz, CDCl$_3$) δ ppm 2.40-3.07 (m, 2H) 3.07-4.11 (m, 2H) 4.11-4.95 (m, 2H) 6.55-7.49 (m, 15H) 7.86-8.05 (m, 2H)

MS ES$^+$: 470

Example 16

4-((4-(2-Fluorophenoxy)-N-(3-(2-fluorophenyl)propyl)benzamido)methyl)benzoic acid

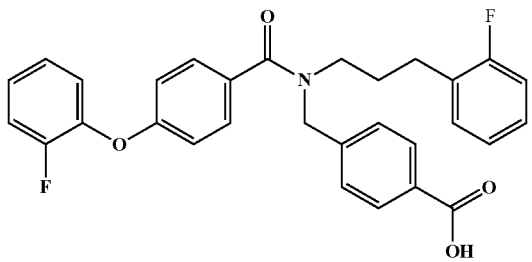 [SMILES: O=C(O)c1ccc(CN(CCCc2ccccc2F)C(=O)c2ccc(Oc3ccccc3F)cc2)cc1]

Prepared from the parent methyl ester (Intermediate C20) using Method H1.

$^1$H NMR (400 MHz, DMSO-d$_6$) δ ppm 1.66-1.98 (m, 2H) 2.17-2.80 (m, 2H) 3.05-3.52 (m, 2H) 4.44-4.90 (m, 2H) 6.83-7.55 (m, 14H) 7.85-8.01 (m, 2H) 12.90 (br s, 1H)

MS ES$^+$: 502

Example 17

4-((4-(2-Fluorophenoxy)-N-(3-(3-fluorophenyl)propyl)benzamido)methyl)benzoic acid

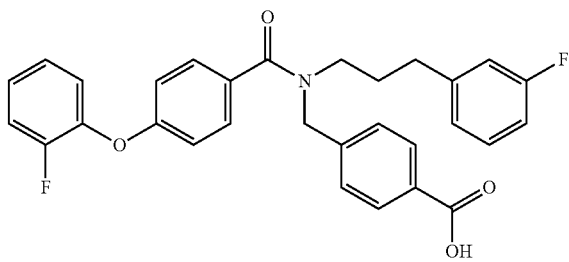 [SMILES: O=C(O)c1ccc(CN(CCCc2cccc(F)c2)C(=O)c2ccc(Oc3ccccc3F)cc2)cc1]

Prepared from the parent methyl ester (Intermediate C21) using Method H1.

$^1$H NMR (400 MHz, DMSO-$d_6$) δ ppm 1.70-1.95 (m, 2H) 2.30-2.40 (m, 2H) 3.30-3.40 (m, 2H) 4.74 (br s, 2H) 6.80-7.56 (m, 14H) 7.87-7.99 (m, 2H) 12.88 (br s, 1H)

MS ES$^+$: 502

Example 18

4-((4-(2-Fluorophenoxy)-N-((trans-2-phenylcyclopropyl)methyl)-benzamido)methyl)benzoic acid

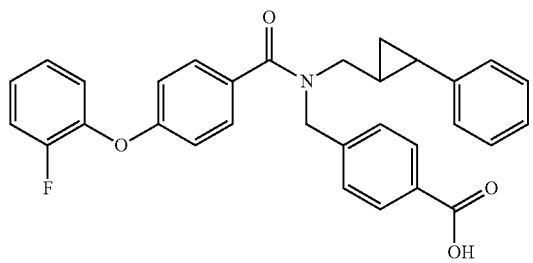 [SMILES: O=C(O)c1ccc(CN(CC2CC2c2ccccc2)C(=O)c2ccc(Oc3ccccc3F)cc2)cc1]

Prepared from the parent methyl ester (Intermediate C22) using Method H1.

$^1$H NMR (400 MHz, CD$_2$Cl$_2$) δ ppm 0.92 (br s, 2H) 1.20-1.35 (m, 1H) 1.52-1.78 (m, 1H) 3.42 (s, 2H) 4.75-4.99 (m, 2H) 6.86-7.10 (m, 4H) 7.10-7.29 (m, 6H) 7.29-7.50 (m, 5H) 8.00-8.12 (m, 2H)

MS ES$^+$: 496

Example 19

(S)-4-((4-(2-Fluorophenoxy)-N-(2-hydroxy-3-phenylpropyl)benzamido)methyl)benzoic acid

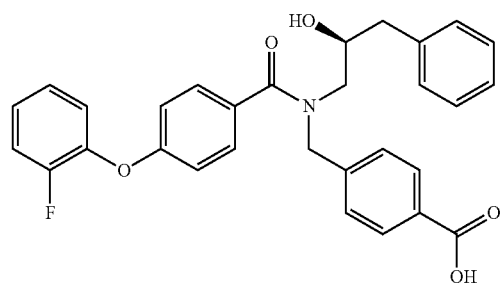 [SMILES: O=C(O)c1ccc(CN(C[C@@H](O)Cc2ccccc2)C(=O)c2ccc(Oc3ccccc3F)cc2)cc1]

Prepared from the parent methyl ester (Intermediate C23) using Method H1.

$^1$H NMR (400 MHz, DMSO-$d_6$) δ ppm 2.60-2.76 (m, 1H) 2.95-3.30 (m, 2H) 3.88-4.17 (m, 1H) 4.65 (br s, 2H) 4.85-4.97 (m, 1H) 5.00-5.29 (m, 1H) 6.85-7.33 (m, 12H) 7.33-7.50 (m, 3H) 7.79-7.90 (m, 2H)

MS ES$^+$: 500

Example 20

(R)-4-((4-(2-Fluorophenoxy)-N-(2-hydroxy-3-phenylpropyl)-benzamido)methyl)benzoic acid

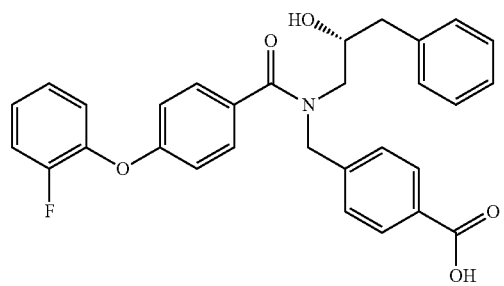 [SMILES: O=C(O)c1ccc(CN(C[C@H](O)Cc2ccccc2)C(=O)c2ccc(Oc3ccccc3F)cc2)cc1]

Prepared from the parent methyl ester (Intermediate C24) using Method H1.

$^1$H NMR (400 MHz, DMSO-$d_6$) δ ppm 2.55-2.79 (m, 1H) 2.92-3.40 (m, 2H) 3.83-4.17 (m, 1H) 4.72 (br s, 2H) 4.85-5.05 (m, 1H) 5.06-5.23 (m, 1H) 6.83-7.53 (m, 15H) 7.84-7.97 (m, 2H)

MS ES$^+$: 500

Example 21

4-((4-(2-Fluorophenoxy)-N-(4-phenylbutyl)-benzamido)methyl)benzoic acid

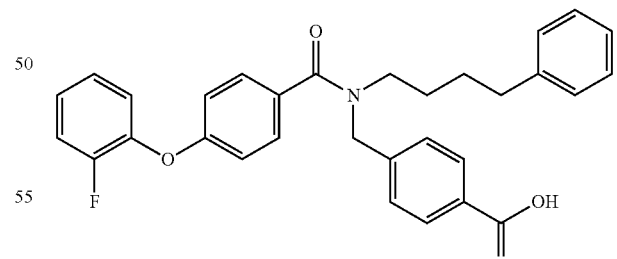

Prepared from the parent methyl ester (Intermediate C25) using Method H1.

$^1$H NMR (400 MHz, DMSO-$d_6$) δ ppm 1.29-1.70 (m, 2H) 2.32-2.84 (m, 2H) 3.10-3.55 (m, 2H) 4.62 (br s, 2H) 6.86-7.46 (m, 15H) 7.77-7.95 (m, 2H) 12.57 (br s, 1H)

MS ES$^+$: 498

Example 22

4-((N-(Cyclopropylmethyl)-4-(o-tolyloxy)benzamido)methyl)benzoic acid

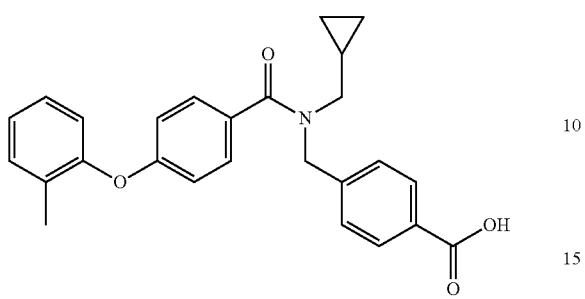

Prepared from the parent methyl ester (Intermediate C26) using Method H1.

$^1$H NMR (400 MHz, DMSO-$d_6$) δ ppm −0.25-0.25 (m 2H) 0.25-0.50 (m, 2H) 0.74-1.11 (m, 1H) 2.13 (s, 3H) 2.87-3.47 (m, 2H) 4.78 (br s, 2H) 6.75-7.62 (m, 10H) 7.83-7.98 (m, 2H) 12.87 (br s, 1H)

MS ES$^+$: 416

Example 23

4-((N-(Cyclobutylmethyl)-4-(o-tolyloxy)benzamido)methyl)benzoic acid

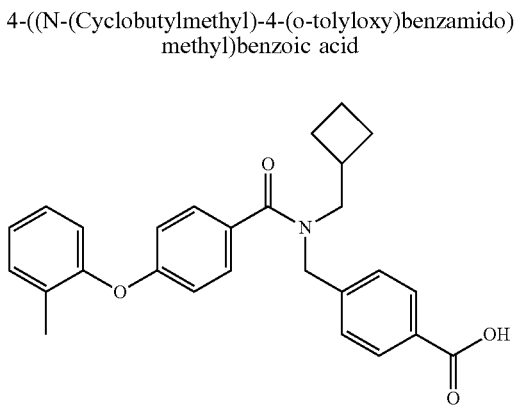

Prepared from the parent methyl ester (Intermediate C27) using Method H1.

$^1$H NMR (400 MHz. DMSO-$d_6$) δ ppm 1.23-1.99 (m, 7H) 2.15 (s, 3H) 2.40-2.74 (m, 2H) 4.65 (br s, 2H) 6.76-7.64 (m, 10H) 7.87-8.02 (m, 2H) 12.90 (br s, 1H)

MS ES$^+$: 430

Example 24

4-((N-Benzyl-4-(o-tolyloxy)benzamido)methyl)benzoic acid

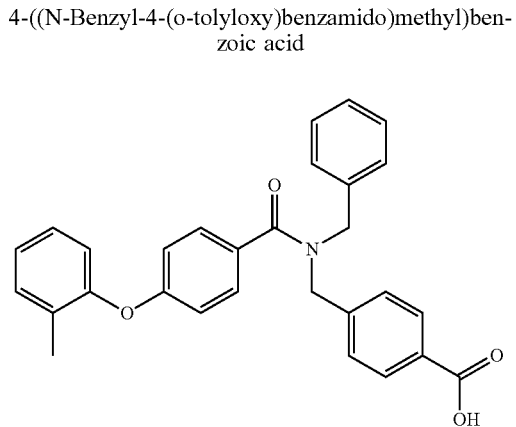

Prepared from the parent methyl ester (Intermediate C28) using Method H1.

$^1$H NMR (400 MHz, DMSO-$d_6$) δ ppm 2.14 (s, 3H) 4.58 (br s, 4H) 6.62-7.04 (m, 3H) 7.07-7.60 (m, 12H) 7.84-8.00 (m, 2H) 12.90 (br s, 1H)

MS ES$^+$: 452

Example 25

4-((N-Phenethyl-4-(o-tolyloxy)benzamido)methyl)benzoic acid

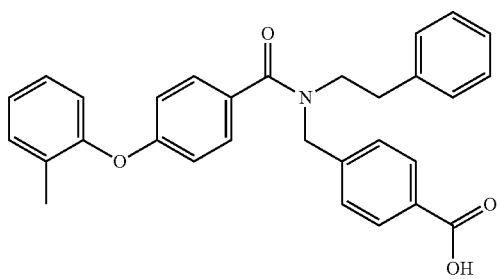 [SMILES: Cc1ccccc1Oc1ccc(C(=O)N(CCc2ccccc2)Cc2ccc(C(=O)O)cc2)cc1]

Prepared from the parent methyl ester (Intermediate C29) using Method H1.

$^1$H NMR (400 MHz, DMSO-$d_6$) δ ppm 2.15 (br s, 3H) 2.72-2.98 (m, 2H) 3.34-3.59 (m, 2H) 4.43-4.88 (m, 2H) 6.82-7.02 (m, 4H) 7.28 (br s, 11H) 7.88-7.96 (m, 2H)

MS ES$^+$: 466

Example 26

4-((N-Phenethyl-4-(2-(trifluoromethyl)phenoxy)benzamido)-methyl)benzoic acid

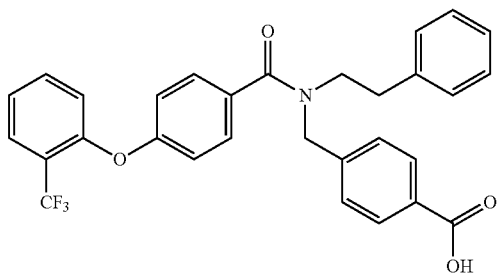 [SMILES: O=C(O)c1ccc(CN(CCc2ccccc2)C(=O)c2ccc(Oc3ccccc3C(F)(F)F)cc2)cc1]

Prepared from the parent methyl ester (Intermediate C30) using Method H1.

$^1$H NMR (400 MHz, DMSO-$d_6$) δ ppm 2.71-2.99 (m, 2H) 3.34-3.59 (m, 2H) 4.43-4.87 (m, 2H) 6.89-7.42 (m, 12H) 7.43-7.54 (m, 1H) 7.64-7.73 (m, 1H) 7.77-7.85 (m, 1H) 7.88-7.98 (m, 2H)

MS ES$^+$: 520

Example 27

4-((N-Benzyl-4-(2-cyanophenoxy)benzamido)methyl)benzoic acid

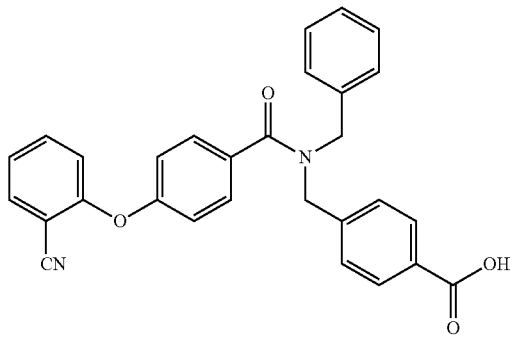 [SMILES: N#Cc1ccccc1Oc1ccc(C(=O)N(Cc2ccccc2)Cc2ccc(C(=O)O)cc2)cc1]

Prepared from the parent methyl ester (Intermediate C31) using Method H1.

$^1$H NMR (400 MHz, DMSO-$d_6$) ppm 4.40-4.76 (m, 4H) 7.00-7.77 (m, 15H) 7.85-8.00 (m, 2H) 12.97 (br s, 1H)

MS ES$^+$: 463

Example 28

4-((N-Ethyl-4-(2-methoxyphenoxy)benzamido)methyl)benzoic acid

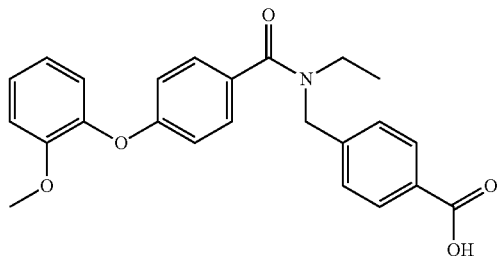 [SMILES: CCN(Cc1ccc(C(=O)O)cc1)C(=O)c1ccc(Oc2ccccc2OC)cc1]

Prepared from the parent methyl ester (Intermediate C32) using Method H1.

$^1$H NMR (400 MHz, DMSO-$d_6$) δ ppm 1.01-1.11 (m, 3H) 3.22-3.33 (m, 2H) 3.73 (s, 3H) 4.68 (br s, 2H) 6.79-6.88 (m, 2H) 6.96-7.03 (m, 1H) 7.07-7.13 (m, 1H) 7.16-7.28 (m, 2H) 7.40 (br s, 4H) 7.89-7.96 (m, 2H) 12.88 (br s, 1H)

MS ES$^+$: 406

Example 29

4-((N-(2,2-Difluoroethyl)-4-(2-methoxyphenoxy)benzamido)-methyl)benzoic acid

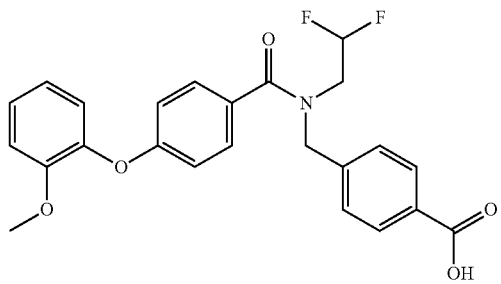 [SMILES: COc1ccccc1Oc1ccc(C(=O)N(Cc2ccc(C(=O)O)cc2)CC(F)F)cc1]

Prepared from the parent methyl ester (Intermediate C33) using Method H1.

$^1$H NMR (400 MHz, DMSO-$d_6$) δ ppm 3.64-3.86 (m, 5H) 4.74 (br s, 2H) 6.07-6.44 (m, 1H) 6.78-6.92 (m, 2H) 6.96-7.03 (m, 1H) 7.07-7.13 (m, 1H) 7.15-7.46 (m, 6H) 7.87-7.97 (m, 2H) 12.93 (br s, 1H)

MS ES$^+$: 442

Example 30

4-((N-Isobutyl-4-(2-methoxyphenoxy)benzamido)methyl)benzoic acid

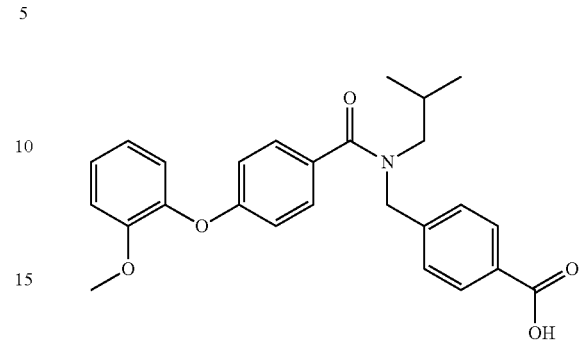

Prepared from the parent methyl ester (Intermediate C34) using Method H1.

$^1$H NMR (400 MHz, DMSO-$d_6$) δ ppm 0.58-0.97 (m, 6H) 1.80-2.13 (m, 1H) 3.06-3.19 (m, 2H) 3.72 (s, 3H) 4.68 (s, 2H) 6.77-6.90 (m, 2H) 6.94-7.05 (m, 1H) 7.05-7.13 (m, 1H) 7.16-7.53 (m, 6H) 7.87-7.97 (m, 2H) 12.91 (br s, 1H)

MS ES$^+$: 434

Example 31

4-((N-(Cyclopropylmethyl)-4-(2-methoxyphenoxy)benzamido)-methyl)benzoic acid

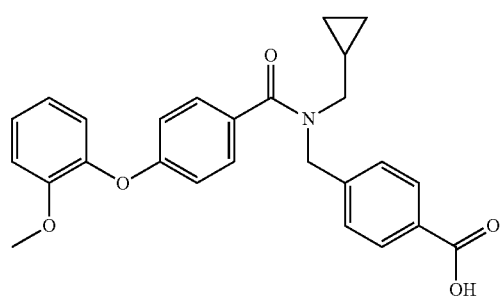 [SMILES: COc1ccccc1Oc1ccc(C(=O)N(Cc2ccc(C(=O)O)cc2)CC2CC2)cc1]

Prepared from the parent methyl ester (Intermediate C35) using Method H1.

$^1$H NMR (400 MHz, DMSO-$d_6$) δ −0.14-0.20 (m, 2H) 0.30-0.44 (m, 2H) 0.81-1.03 (m, 1H) 3.15 (br s, 2H) 3.70 (s, 3H) 4.79 (br s, 2H) 6.78-6.91 (m, 2H) 6.96-7.03 (m, 1H) 7.08-7.14 (m, 1H) 7.16-7.28 (m, 2H) 7.30-7.50 (m, 4H) 7.87-7.96 (m, 2H) 12.88 (s, 1H)

MS ES$^+$: 432

Example 32

4-((4-(2-Methoxyphenoxy)-N-(3-phenylpropyl)benzamido)-methyl)benzoic acid

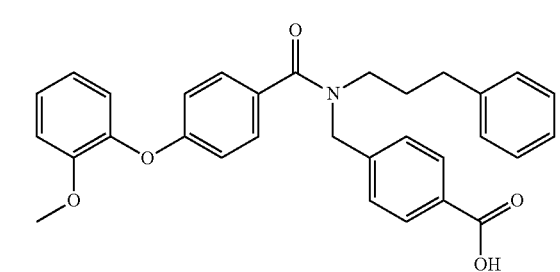 [SMILES: COc1ccccc1Oc1ccc(C(=O)N(CCCc2ccccc2)Cc2ccc(C(=O)O)cc2)cc1]

Prepared from the parent methyl ester (Intermediate C36) using Method H1.

$^1$H NMR (400 MHz, DMSO-d$_6$) δ ppm 1.83 (br s, 2H) 2.40 (br s, 2H) 3.22 (br s, 2H) 3.73 (s, 3H) 4.70 (br s, 2H) 6.77-6.82 (m, 2H) 6.95-7.44 (m, 13H) 7.88-7.93 (m, 2H) 12.89 (s, 1H)

MS ES$^+$: 496

Example 33

4-((N-(3-(3-Fluorophenyl)propyl)-4-(2-methoxyphenoxy)-benzamido)methyl)benzoic acid

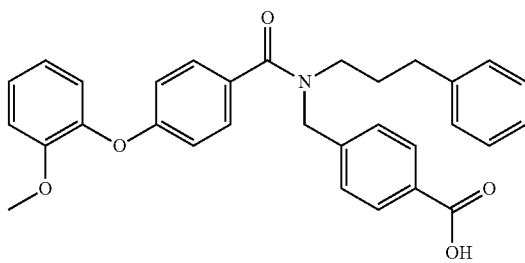

Prepared from the parent methyl ester (Intermediate C37) using Method H1.

$^1$H NMR (400 MHz, DMSO-d$_6$) δ ppm 1.84 (br s, 2H) 2.42 (br s, 2H) 3.21 (br s, 2H) 3.73 (s, 3H) 4.70 (br s, 2H) 6.76-6.82 (m, 2H) 6.83-7.47 (m, 12H) 7.86-7.94 (m, 2H) 12.88 (br s, 1H)

MS ES$^+$: 514

Example 34

4-((N-(Cyclopropylmethyl)-4-(2-ethoxyphenoxy)-benzamido)methyl)benzoic acid

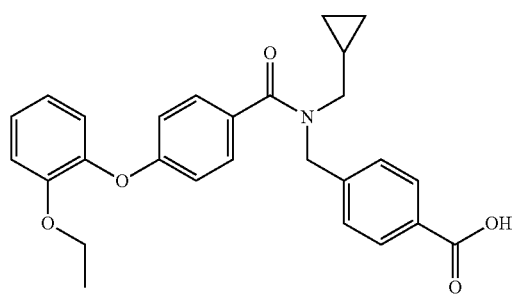 [SMILES: CCOc1ccccc1Oc1ccc(C(=O)N(Cc2ccc(C(=O)O)cc2)CC2CC2)cc1]

Prepared from the parent methyl ester (Intermediate C38) using Method H1.

$^1$H NMR (300 MHz, DMSO-d$_6$) δ ppm −0.24-0.60 (m, 4H) 0.69-1.41 (m, 4H) 2.87-3.31 (m, 2H) 3.80-4.15 (m, 2H) 4.76 (br s, 2H) 6.60-7.57 (m, 1 OH) 7.75-8.00 (m, 2H) 12.86 (br s, 1H)

MS ES$^+$: 446

Example 35

4-((4-(2-Chlorophenoxy)-N-(cyclopropylmethyl) benzamido)-methyl)benzoic acid

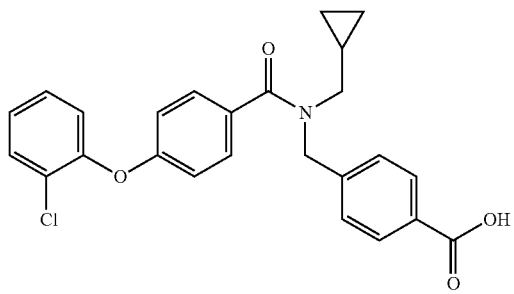 [SMILES: O=C(O)c1ccc(CN(CC2CC2)C(=O)c2ccc(Oc3ccccc3Cl)cc2)cc1]

Prepared from the parent methyl ester (Intermediate C39) using Method H1.

$^1$H NMR (400 MHz, DMSO-d$_6$) ppm ppm −0.30-0.23 (m, 2H) 0.23-0.50 (m, 2H) 0.74-1.12 (m, 1H) 2.81-3.41 (m, 2H) 4.79 (br s, 2H) 6.86-7.04 (m, 2H) 7.12-7.66 (m, 8H) 7.84-7.97 (m, 2H) 12.87 (br s, 1H)

MS ES$^+$: 436

Example 36

4-((4-(2-Chlorophenoxy)-N-phenethylbenzamido) methyl)benzoic acid

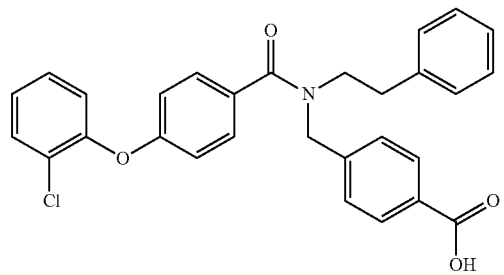 [SMILES: O=C(O)c1ccc(CN(CCc2ccccc2)C(=O)c2ccc(Oc3ccccc3Cl)cc2)cc1]

Prepared from the parent methyl ester (Intermediate C40) using Method H1.

$^1$H NMR (400 MHz, DMSO-d$_6$) δ ppm 2.72-2.95 (m, 2H) 3.35-3.60 (m, 2H) 4.41-4.88 (m, 2H) 6.88-7.01 (m, 3H) 7.14-7.54 (m, 11H) 7.58-7.66 (m, 1H) 7.87-7.98 (m, 2H) 12.89 (br s, 1H)

MS ES$^+$: 486

Example 37

4-((N-(Cyclopropylmethyl)-4-(2,6-difluorophenoxy) benzamido)-methyl)benzoic acid

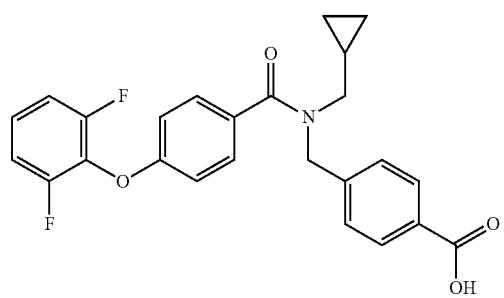 [SMILES: O=C(O)c1ccc(CN(CC2CC2)C(=O)c2ccc(Oc3c(F)cccc3F)cc2)cc1]

Prepared from the parent methyl ester (Intermediate C41) using Method H1.

¹H NMR (400 MHz, DMSO-d₆) δ ppm 0.00 (br s, 2H) 0.38 (br s, 2H) 0.92 (br s, 1H) 3.12 (br s, 2H) 4.80 (br s, 2H) 7.01 (br s, 2H) 7.24-7.56 (m, 7H) 7.84-7.99 (m, 2H) 12.88 (br s, 1H)

MS ES⁺: 438

Example 38

4-((N-(2-Cyclopropylethyl)-4-(2,6-difluorophenoxy)benzamido)-methyl)benzoic acid

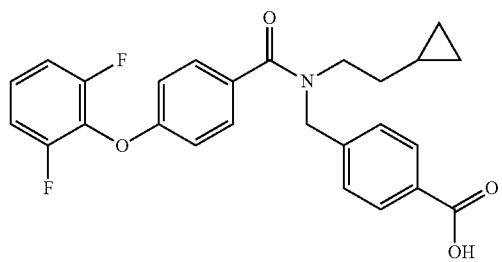

Prepared from the parent methyl ester (Intermediate C42) using Method H1.

¹H NMR (400 MHz, DMSO-d₆) δ ppm −0.27-0.10 (m, 2H) 0.18-0.75 (m, 3H) 1.25-1.57 (m, 2H) 3.14-3.47 (m, 2H) 4.52-4.81 (m, 2H) 6.87-7.11 (m, 2H) 7.22-7.56 (m, 7H) 7.84-8.00 (m, 2H) 12.88 (br s, 1H)

MS ES⁺: 452

Example 39

4-((N-Benzyl-4-(2,6-difluorophenoxy)benzamido)methyl)benzoic acid

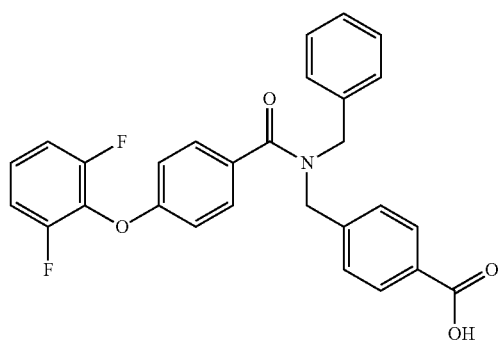 [SMILES: O=C(O)c1ccc(CN(Cc2ccccc2)C(=O)c2ccc(Oc3c(F)cccc3F)cc2)cc1]

Prepared from the parent methyl ester (Intermediate C43) using Method H1.

¹H NMR (400 MHz, DMSO-d₆) δ ppm 4.40-4.68 (m, 4H) 6.95-7.04 (m, 2H) 7.11-7.44 (m, 10H) 7.45-7.55 (m, 2H) 7.86-7.94 (m, 2H)

MS ES⁺: 474

Example 40

4-((N-(Cyclopropylmethyl)-4-(2-fluoro-6-methyl-phenoxy)-benzamido)methyl)benzoic acid

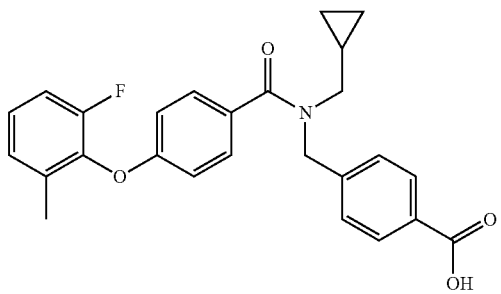 [SMILES: Cc1cccc(F)c1Oc1ccc(C(=O)N(Cc2ccc(C(=O)O)cc2)CC2CC2)cc1]

Prepared from the parent methyl ester (Intermediate C44) using Method H1.

¹H NMR (400 MHz, DMSO-d₆) δ ppm −0.16-0.24 (m, 2H) 0.26-0.48 (m, 2H) 0.77-1.08 (m, 1H) 2.15 (s, 3H) 2.94-3.32 (m, 2H) 4.78 (br s, 2H) 6.88 (br s, 2H) 7.09-7.28 (m, 3H) 7.42 (br s, 4H) 7.85-7.96 (m, 2H) 12.87 (br s, 1H)

MS ES⁺: 434

Example 41

4-((N-(Cyclobutylmethyl)-4-(2-fluoro-6-methylphenoxy)benzamido)methyl)benzoic acid

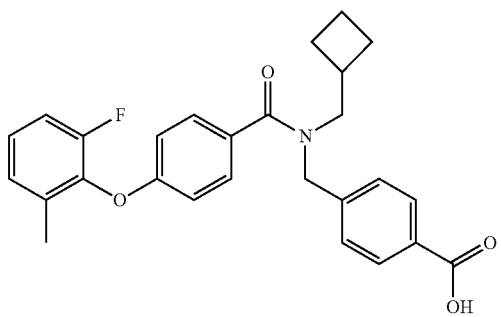 [SMILES: Cc1cccc(F)c1Oc1ccc(C(=O)N(Cc2ccc(C(=O)O)cc2)CC2CCC2)cc1]

Prepared from the parent methyl ester (Intermediate C45) using Method H1.

¹H NMR (400 MHz, DMSO-d₆) δ ppm 1.36-2.01 (m, 6H) 2.16 (s, 3H) 3.22-3.42 (m, 3H) 4.64 (br s, 2H) 6.80-6.95 (m, 2H) 7.17-7.29 (m, 3H) 7.32-7.56 (m, 4H) 7.81-8.02 (m, 2H) 12.88 (br s, 1H)

MS ES⁺: 448

Example 42

4-((4-(2-Chloro-6-fluorophenoxy)-N-(cyclopropylmethyl)-benzamido)methyl)benzoic acid

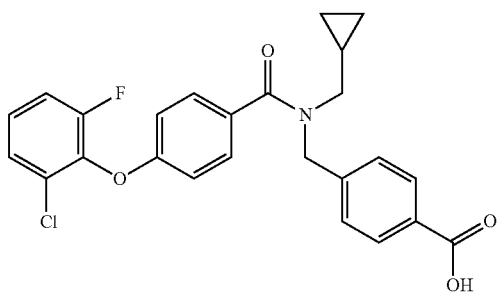 [SMILES: O=C(O)c1ccc(CN(CC2CC2)C(=O)c2ccc(Oc3c(F)cccc3Cl)cc2)cc1]

Prepared from the parent methyl ester (Intermediate C46) using Method H1.

¹H NMR (400 MHz, DMSO-d₆) δ ppm 0.00 (br s, 2H) 0.38 (br s, 2H) 0.93 (br s, 1H) 3.13 (br s, 2H) 4.80 (br s, 2H) 6.95 (br s, 2H) 7.24-7.60 (m, 7H) 7.86-7.99 (m, 2H) 12.88 (br s, 1H)

MS ES⁺: 454

Example 43

4-((4-(2-Chloro-6-fluorophenoxy)-N-(2-cyclopropylethyl)-benzamido)methyl)benzoic acid

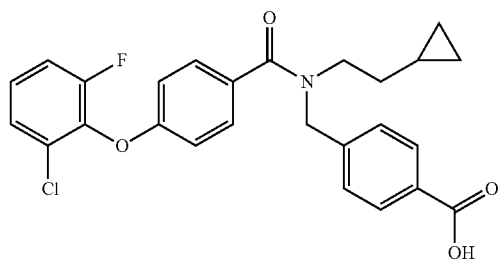 [SMILES: O=C(O)c1ccc(CN(CCC2CC2)C(=O)c2ccc(Oc3c(F)cccc3Cl)cc2)cc1]

Prepared from the parent methyl ester (Intermediate C47) using Method H1.

¹H NMR (400 MHz, DMSO-d₆) δ ppm −0.29-0.77 (m, 5H) 1.23-1.57 (m, 2H) 3.15-3.52 (m, 2H) 4.49-4.84 (m, 2H) 6.95 (m, 2H) 7.21-7.57 (m, 7H) 7.89-7.96 (m, 2H) 12.89 (br s, 1H)

MS ES⁺: 468

Example 44

4-((N-Benzyl-4-(2-chloro-6-fluorophenoxy)benzamido)-methyl)benzoic acid

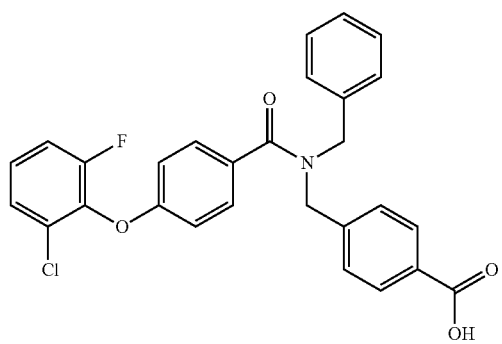

Prepared from the parent methyl ester (Intermediate C48) using Method H1.

¹H NMR (400 MHz, DMSO-d₆) δ ppm 4.39-4.70 (m, 4H) 6.87-6.99 (m, 2H) 7.08-7.59 (m, 12H) 7.86-7.95 (m, 2H) 12.97 (br s, 1H)

MS ES⁺: 490

Example 45

4-((4-(2,6-Dimethylphenoxy)-N-isopentylbenzamido)methyl)benzoic acid

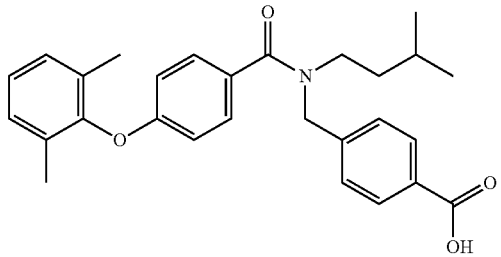 [SMILES: Cc1cccc(C)c1Oc1ccc(C(=O)N(CCC(C)C)Cc2ccc(C(=O)O)cc2)cc1]

Prepared from the parent methyl ester (Intermediate C49) using Method H2.

¹H NMR (400 MHz, DMSO-d₆) δ ppm 0.39-1.61 (m, 9H) 2.06 (s, 6H) 2.75-3.48 (m, 2H) 4.47-4.86 (m, 2H) 6.62-6.89 (m, 2H) 7.05-7.25 (m, 3H) 7.25-7.58 (m, 4H) 7.85-8.02 (m, 2H) 12.89 (br s, 1H)

MS ES⁺: 446

Example 46

4-((N-Benzyl-4-(2,6-dimethylphenoxy)benzamido)methyl)benzoic acid

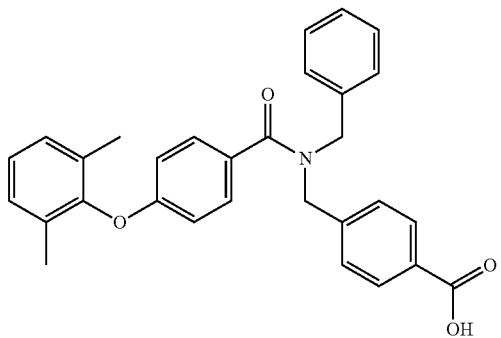 [SMILES: Cc1cccc(C)c1Oc1ccc(C(=O)N(Cc2ccccc2)Cc2ccc(C(=O)O)cc2)cc1]

Prepared from the parent methyl ester (Intermediate C50) using Method H2.

¹H NMR (400 MHz, DMSO-d₆) δ ppm 2.04 (s, 6H) 4.35-4.79 (m, 4H) 6.68-6.87 (m, 2H) 7.02-7.58 (m, 12H) 7.82-8.02 (m, 2H) 12.89 (br s, 1H)

MS ES⁺: 466

Example 47

4-((4-(2,6-Dimethylphenoxy)-N-phenethylbenzamido)methyl)benzoic acid

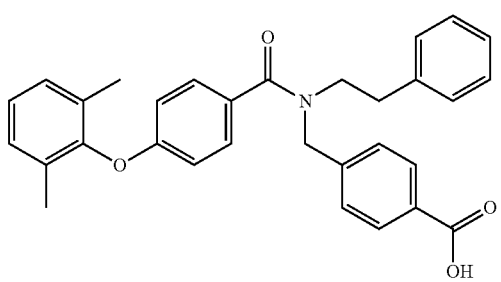 [SMILES: Cc1cccc(C)c1Oc1ccc(C(=O)N(CCc2ccccc2)Cc2ccc(C(=O)O)cc2)cc1]

Prepared from the parent methyl ester (Intermediate C51) using Method H2.

$^1$H NMR (400 MHz, DMSO-d$_6$) δ ppm 2.07 (s, 6H) 2.62-3.04 (m, 2H) 3.10-3.70 (m, 2H) 4.35-4.98 (m, 2H) 6.65-7.63 (m, 14H) 7.85-8.03 (m, 2H)

MS ES$^+$: 480

Example 48

4-((4-(3-Methoxyphenoxy)-N-phenethylbenzamido)methyl)benzoic acid

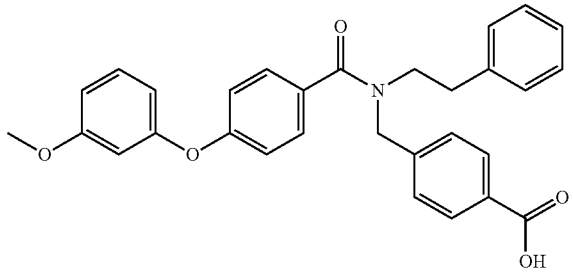 [SMILES: COc1cccc(Oc2ccc(C(=O)N(CCc3ccccc3)Cc3ccc(C(=O)O)cc3)cc2)c1]

Prepared from the parent methyl ester (Intermediate C52) using Method H1.

$^1$H NMR (400 MHz, DMSO-d$_6$) δ ppm 2.72-2.95 (m, 2H) 3.35-3.61 (m, 2H) 3.74 (s, 3H) 4.40-4.88 (m, 2H) 6.54-6.66 (m, 2H) 6.72-6.80 (m, 1H) 6.90-7.11 (m, 3H) 7.13-7.57 (m, 9H) 7.86-8.01 (m, 2H) 12.87 (br s, 1H)

MS ES$^+$: 482

Example 49

4-((4-(4-Methoxyphenoxy)-N-phenethylbenzamido)methyl)benzol acid

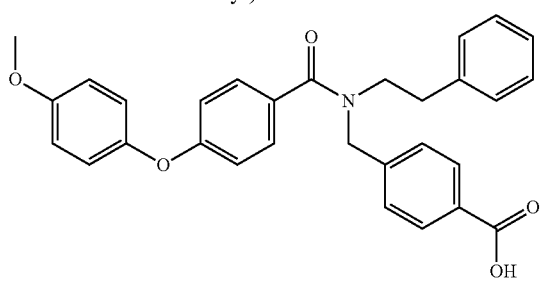

Prepared from the parent methyl ester (Intermediate C53) using Method H1.

$^1$H NMR (400 MHz, DMSO-d$_6$) δ ppm 2.70-2.96 (m, 2H) 3.35-3.57 (m, 2H) 3.76 (s, 3H) 4.40-4.87 (m, 2H) 6.85-7.56 (m, 15H) 7.85-8.00 (m, 2H) 12.90 (br s, 1H)

MS ES$^+$: 482

Example 50

4-((4-(3-Chlorophenoxy)-N-phenethylbenzamido)methyl)benzoic acid

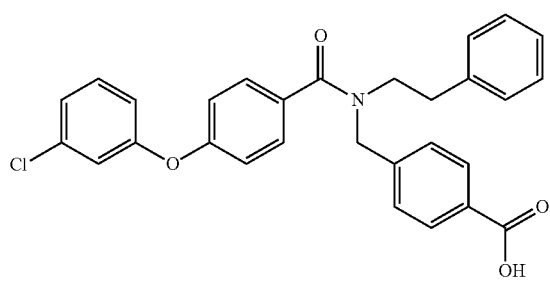 [SMILES: O=C(O)c1ccc(CN(CCc2ccccc2)C(=O)c2ccc(Oc3cccc(Cl)c3)cc2)cc1]

Prepared from the parent methyl ester (Intermediate C54) using Method H1.

$^1$H NMR (400 MHz, DMSO-d$_6$) δ ppm 2.73-2.98 (m, 2H) 3.36-3.62 (m, 2H) 4.42-4.90 (m, 2H) 6.87-7.57 (m, 15H) 7.93 (br s, 2H) 12.90 (br s, 1H)

MS ES$^+$: 486

Example 51

4-((N-(Cyclopropylmethyl)-4-((2-fluorobenzyl)oxy)benzamido)-methyl)benzoic acid

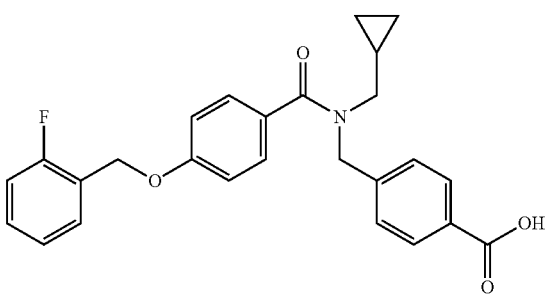 [SMILES: O=C(O)c1ccc(CN(CC2CC2)C(=O)c2ccc(OCc3ccccc3F)cc2)cc1]

Prepared from the parent methyl ester (Intermediate C55) using Method H1.

$^1$H NMR (400 MHz, DMSO-d$_6$) ppm ppm −0.22-0.25 (m, 2H) 0.26-0.47 (m, 2H) 0.77-1.08 (m, 1H) 2.73-3.45 (m, 2H) 4.77 (br s, 2H) 5.15 (s, 2H) 6.98-7.63 (m, 10H) 7.85-7.97 (m, 2H) 12.84 (br s, 1H)

MS ES$^+$: 434

Example 52

4-((N-(Cyclobutylmethyl)-4-((2-fluorobenzyl)oxy)benzamido)-methyl)benzoic acid

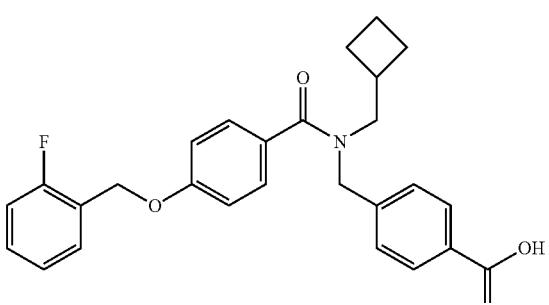

Prepared from the parent methyl ester (Intermediate C56) using Method H1.

$^1$H NMR (400 MHz, DMSO-d$_6$) ppm 1.20-2.20 (m, 7H) 2.26-2.74 (m, 2H) 4.64 (s, 2H) 5.18 (s, 2H) 6.97-7.66 (m, 10H) 7.83-8.07 (m, 2H) 12.81 (br s, 1H)

MS ES$^+$: 448

Example 53

4-((N-Benzyl-4-((2-fluorobenzyl)oxy)benzamido)methyl)benzoic acid

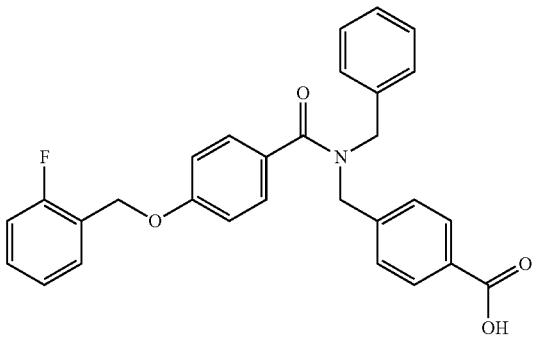 [SMILES: O=C(O)c1ccc(CN(Cc2ccccc2)C(=O)c2ccc(OCc3ccccc3F)cc2)cc1]

Prepared from the parent methyl ester (Intermediate C57) using Method H1.

$^{1}$H NMR (400 MHz, DMSO-d$_{6}$) ppm 4.56 (br s, 4H) 5.16 (s, 2H) 7.00-7.61 (m, 15H) 7.87-7.99 (m, 2H) 12.92 (br s, 1H)

MS ES$^{+}$: 470

Example 54

4-((N-(Cyclopropylmethyl)-2-fluoro-4-(2-fluorophenoxy)-benzamido)methyl)benzoic acid

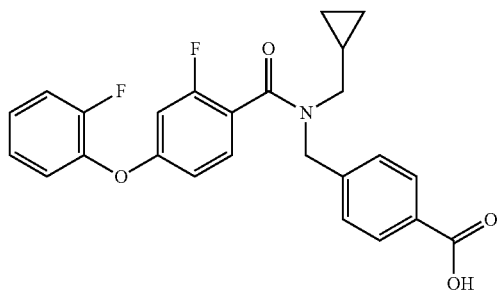 [SMILES: O=C(O)c1ccc(CN(CC2CC2)C(=O)c2ccc(Oc3ccccc3F)cc2F)cc1]

Prepared from the parent methyl ester (Intermediate C59) using Method H1.

$^{1}$H NMR (400 MHz, DMSO-d$_{6}$) δ ppm −0.06-0.28 (m, 2H) 0.31-0.52 (m, 2H) 0.73-1.15 (m, 1H) 2.99-3.41 (m, 2H) 4.55-4.97 (m, 2H) 6.73-7.07 (m, 2H) 7.25-7.56 (m, 7H) 7.86-8.02 (m, 2H) 12.91 (br s, 1H)

MS ES$^{+}$: 438

Example 55

4-((N-Benzyl-4-(2-fluorophenoxy)cyclohexanecarboxamido)-methyl)benzoic acid (ca. 1:1 mixture of cis and trans ring isomers)

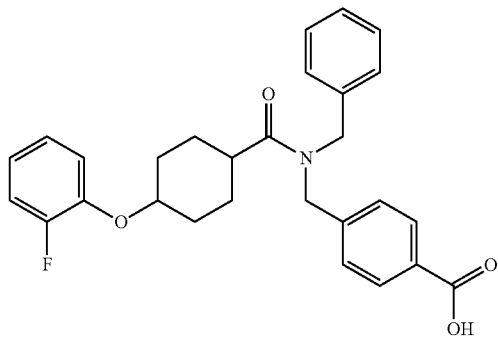 [SMILES: O=C(O)c1ccc(CN(Cc2ccccc2)C(=O)C2CCC(Oc3ccccc3F)CC2)cc1]

Prepared from the parent methyl ester (Intermediate C60) using Method H1.

$^{1}$H NMR (400 MHz, DMSO-d$_{6}$) ppm 1.27-2.13 (m, 8H) 2.61-2.86 (m, 1H) 4.00-4.40 (m, 1H) 4.45-4.73 (m 4H) 6.88-7.00 (m, 1H) 7.05-7.44 (m, 10H) 7.85-8.00 (m, 2H) 12.90 (br s, 1H)

MS ES$^{+}$: 462

Example 56 trans-4-((N-Benzyl-4-(2-methoxyphenoxy)cyclohexanecarboxamido)methyl)benzoic acid

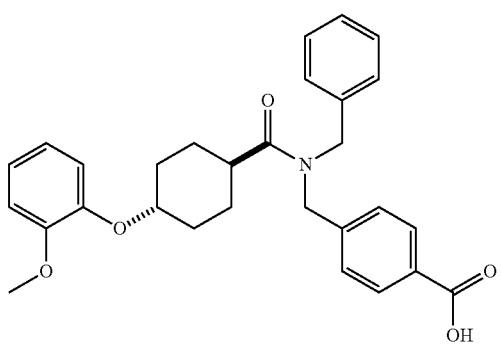

Prepared from the parent methyl ester (Intermediate C61) using Method H1.

$^{1}$H NMR (400 MHz, DMSO-d$_{6}$) ppm 1.10-2.11 (m, 8H) 2.57-2.78 (m, 1H) 3.73 (s, 3H) 4.11-4.25 (m, 1H) 4.46-4.74 (m, 4H) 6.81-7.04 (m, 4H) 7.15-7.44 (m, 7H) 7.86-8.00 (m, 2H) 12.90 (br s, 1H)

MS ES$^{+}$: 474

Example 57 cis-4-((N-(3-(3-Fluorophenyl)propyl)-4-(2-methoxyphenoxy)cyclohexanecarboxamido)methyl)benzoic acid

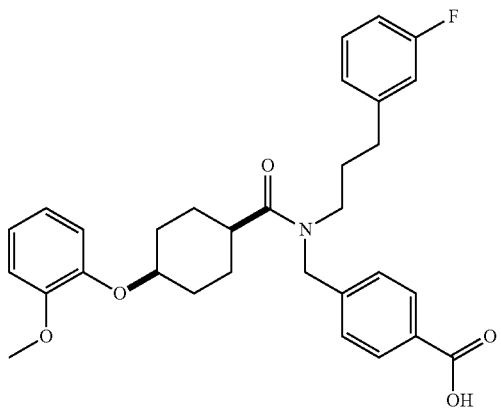

Prepared from the parent methyl ester (Intermediate C62) using Method H1.

$^{1}$H NMR (400 MHz, DMSO-d$_{6}$) ppm 1.34-1.98 (m, 10H) 2.39-2.66 (m, 3H) 3.15-3.40 (m, 2H) 3.71-3.87 (m, 3H) 4.37-4.51 (m, 1H) 4.52-4.78 (m, 2H) 6.79-7.12 (m, 7H) 7.19-7.39 (m, 3H) 7.82-8.01 (m, 2H) 12.80 (br s, 1H)

MS ES$^{+}$: 520

Example 58 trans-4-((N-(3-(3-Fluorophenyl)propyl)-4-(2-methoxyphenoxy)cyclohexanecarboxamido)methyl)benzoic acid

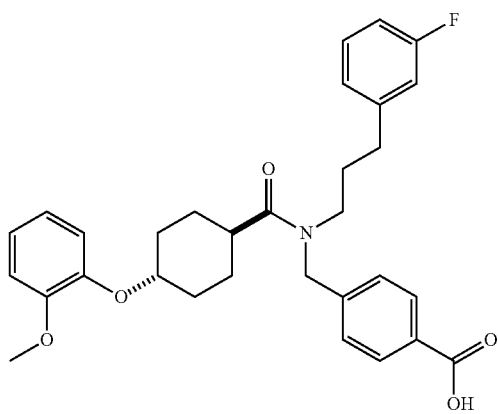

Prepared from the parent methyl ester (Intermediate C63) using Method H1.

$^1$H NMR (400 MHz, DMSO-d$_6$) ppm 1.19-2.13 (m, 10H) 2.36-2.65 (m, 3H) 3.15-3.49 (m, 2H) 3.67-3.81 (m, 3H) 4.09-4.24 (m, 1H) 4.51-4.78 (m, 2H) 6.79-7.10 (m, 7H) 7.18-7.40 (m, 3H) 7.81-8.00 (m, 2H) 12.86 (br s, 1H)

MS ES$^+$: 520

Example 59

2-Fluoro-4-((4-(2-fluorophenoxy)-N-(3-methoxybenzyl)benzamido)methyl)benzoic acid

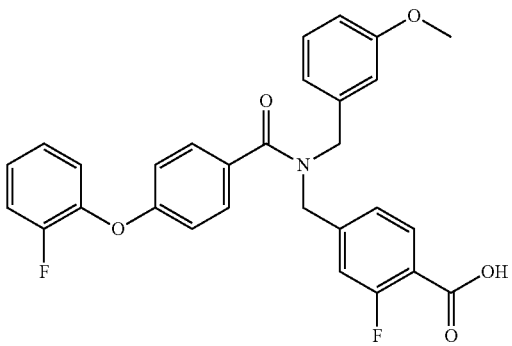 [SMILES: COc1cccc(CN(Cc2ccc(C(=O)O)c(F)c2)C(=O)c2ccc(Oc3ccccc3F)cc2)c1]

Prepared from the parent methyl ester (Intermediate C64) using Method H1.

$^1$H NMR (300 MHz, CDCl$_3$) δ ppm 3.79 (s, 3H) 4.34-4.91 (m, 4H) 6.57-7.34 (m, 12H) 7.34-7.61 (m, 2H) 7.90-8.07 (m, 1H)

MS ES$^+$: 504

Example 60

4-((4-(2-Fluorophenoxy)-N-propylbenzamido)methyl)benzoic acid

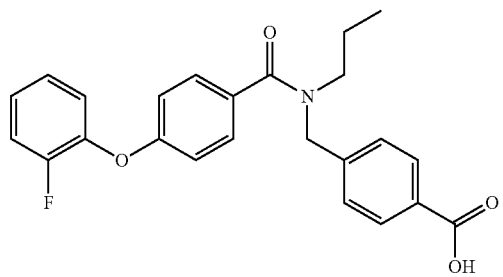 [SMILES: CCCN(Cc1ccc(C(=O)O)cc1)C(=O)c1ccc(Oc2ccccc2F)cc1]

Prepared from the parent methyl ester (Intermediate C25a) using Method H1.

$^1$H NMR (400 MHz, CDCl$_3$) δ ppm 0.65-1.06 (m, 3H) 1.48-1.79 (m, 2H) 3.11-3.52 (m, 2H), 4.56-4.85 (m, 2H) 6.87-7.52 (m, 10H) 8.06-8.12 (m, 2H)

MS ES$^+$: 408

Example 61

4-((4-(2-Methoxyphenoxy)-N-(2,2,2-trifluoroethyl)benzamido)methyl)benzoic acid

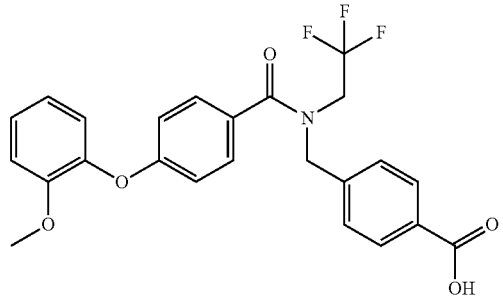 [SMILES: COc1ccccc1Oc1ccc(C(=O)N(Cc2ccc(C(=O)O)cc2)CC(F)(F)F)cc1]

Prepared from the parent methyl ester (Intermediate C40a) using Method H1.

$^1$H NMR (400 MHz, CDCl$_3$) δ ppm 3.79 (s, 3H) 3.84-4.12 (m, 2H) 4.77-4.95 (m, 2H) 6.85-7.47 (m, 10H) 8.03-8.12 (m, 2H)

MS ES$^+$: 460

Example 62

4-((4-(2-Methoxyphenoxy)-N-propylbenzamido)methyl)benzoic acid

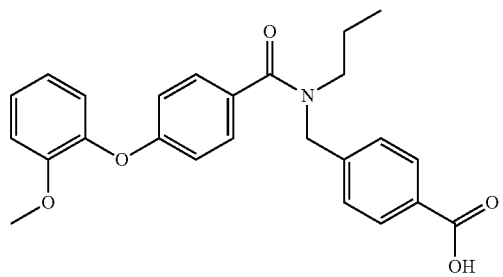 [SMILES: CCCN(Cc1ccc(C(=O)O)cc1)C(=O)c1ccc(Oc2ccccc2OC)cc1]

Prepared from the parent methyl ester (Intermediate C40b) using Method H1.

$^1$H NMR (400 MHz, CDCl$_3$) δ ppm 0.65-1.05 (m, 3H) 1.41-1.78 (m, 2H) 3.12-3.52 (m, 2H), 3.80 (s, 3H) 4.55-4.87 (m, 2H) 6.81-7.51 (m, 10H) 8.04-8.12 (m, 2H)

MS ES$^+$: 420

Example 63

4-((N-(2,2-Difluoropropyl)-4-(2-methoxyphenoxy)-benzamido)methyl)benzoic acid

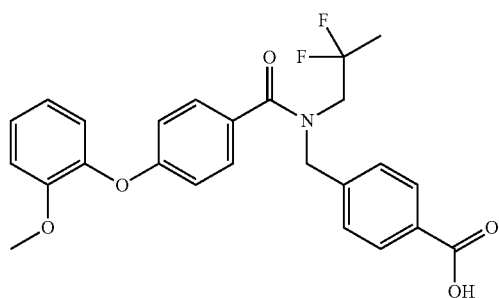 [SMILES: COc1ccccc1Oc1ccc(C(=O)N(Cc2ccc(C(=O)O)cc2)CC(C)(F)F)cc1]

Prepared from the parent methyl ester (Intermediate C40c) using Method H1.

$^1$H NMR (400 MHz, CDCl$_3$) δ ppm 1.32-1.84 (m, 3H) 3.45-4.02 (m, 5H) 4.65-5.06 (m, 2H) 6.79-7.50 (nm 10H) 7.99-8.15 (m, 2H)

MS ES$^+$: 456

Example 64

4-((4-(2-Methoxyphenoxy)-N-(3,3,3-trifluoropropyl)-benzamido)methyl)benzoic acid

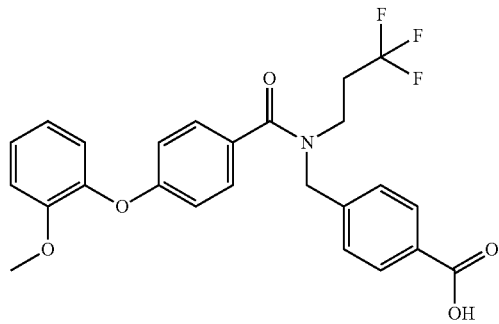 [SMILES: COc1ccccc1Oc1ccc(C(=O)N(CCC(F)(F)F)Cc2ccc(C(=O)O)cc2)cc1]

Prepared from the parent methyl ester (Intermediate C40d) using Method H1.

$^1$H NMR (400 MHz, CDCl$_3$) δ ppm 2.35-2.67 (m, 2H) 3.50-3.69 (m, 5H) 4.58-4.81 (m, 2H) 6.80-7.48 (m, 10H) 8.06-8.14 (m, 2H)

MS ES$^+$: 474

Example 65

4-((N-Butyl-4-(2-methoxyphenoxy)benzamido)methyl)benzoic acid

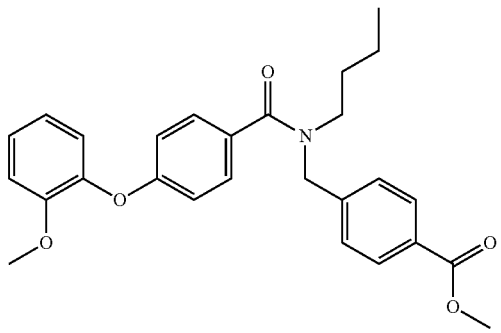 [SMILES: CCCCN(Cc1ccc(C(=O)OC)cc1)C(=O)c1ccc(Oc2ccccc2OC)cc1]

Prepared from the parent methyl ester (Intermediate C40e) using Method H1.

$^1$H NMR (400 MHz, CDCl$_3$) δ ppm 0.67-1.01 (m, 3H) 1.01-1.74 (m, 4H) 3.11-3.56 (m, 2H) 4.56-4.90 (m, 2H) 6.80-7.58 (m, 10H) 8.03-8.14 (m, 2H)

MS ES$^+$: 434

Example 66

4-((N-(Cyclopropylmethyl)-2-fluoro-4-(2-methoxyphenoxy)benzamido)methyl)benzoic acid

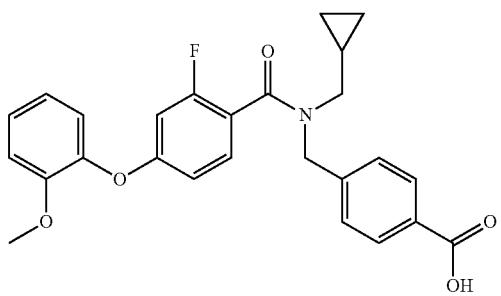 [SMILES: COc1ccccc1Oc1ccc(C(=O)N(Cc2ccc(C(=O)O)cc2)CC2CC2)c(F)c1]

Prepared from the parent methyl ester (Intermediate C65) using Method H1.

$^1$H NMR (400 MHz, DMSO-d$_6$) δ ppm −0.06-0.29 (m, 2H) 0.30-0.53 (m, 2H) 0.78-1.16 (m, 1H) 2.98-3.45 (m, 2H) 3.77 (s, 3H) 4.57-4.98 (m, 2H) 6.59-6.87 (m, 2H) 6.98-7.51 (m, 7H) 7.84-8.00 (m, 2H) 12.90 (br s, 1H)

MS ES$^+$: 450

Example 67

4-((N-(Cyclopropylmethyl)-4-(2-fluoro-6-methoxyphenoxy)benzamido)methyl)benzoic acid

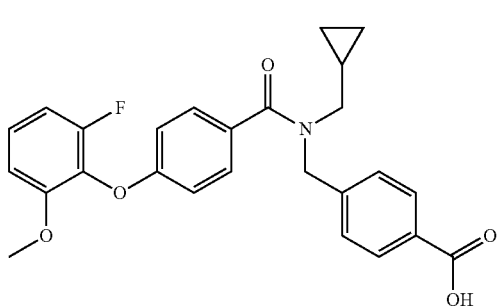 [SMILES: COc1cccc(F)c1Oc1ccc(C(=O)N(Cc2ccc(C(=O)O)cc2)CC2CC2)cc1]

Prepared from the parent methyl ester (Intermediate C66) using Method H1.

¹H NMR (400 MHz, CDCl₃) δ ppm −0.10-0.28 (m, 2H) 0.37-0.58 (m, 2H) 0.78-1.15 (m, 1H) 2.98-3.50 (m, 2H) 3.79 (s, 3H) 4.68-5.05 (m, 2H) 6.69-7.50 (m, 9H) 8.02-8.11 (m, 2H)

MS ES⁺: 450

Example 68

4-((N-(Cyclopropylmethyl)-4-(4-fluoro-2-methoxyphenoxy)benzamido)methyl)benzoic acid

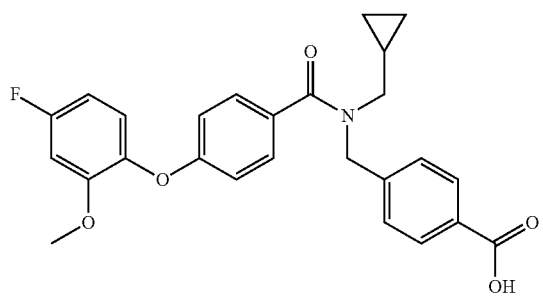 [SMILES: COc1cc(F)ccc1Oc1ccc(C(=O)N(Cc2ccc(C(=O)O)cc2)CC2CC2)cc1]

Prepared from the parent methyl ester (Intermediate C67) using Method H1.

¹H NMR (400 MHz, CDCl₃) δ ppm −0.09-0.29 (m, 2H) 0.44-0.58 (m, 2H) 0.78-1.17 (m, 1H) 3.01-3.55 (m, 2H) 3.78 (s, 3H) 4.70-5.05 (m, 2H) 6.70-7.52 (m, 9H) 8.03-8.12 (m, 2H)

MS ES⁺: 450

Example 69

4-((N-(Cyclopropylmethyl)-5-(2-methoxyphenoxy)-picolinamido)methyl)benzoic acid

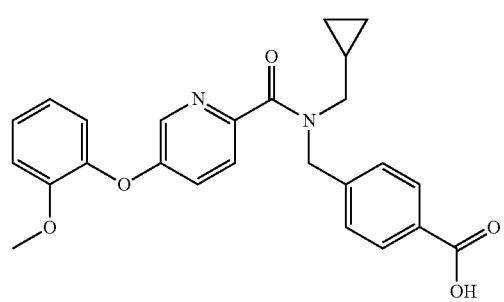 [SMILES: COc1ccccc1Oc1ccc(C(=O)N(Cc2ccc(C(=O)O)cc2)CC2CC2)nc1]

Prepared from the parent methyl ester (Intermediate C68) using Method H1.

¹H NMR (400 MHz, CDCl₃) δ ppm −0.08-0.68 (m, 4H) 0.85-1.33 (m, 1H) 3.16-3.56 (m, 2H) 3.61-4.04 (m, 3H) 4.78-5.19 (m, 2H) 6.80-8.55 (m, 11H)

MS ES⁺: 433

Example 70

4-((4-(o-Tolyloxy)-N-(2,2,2-trifluoroethyl)benzamido)methyl)benzoic acid

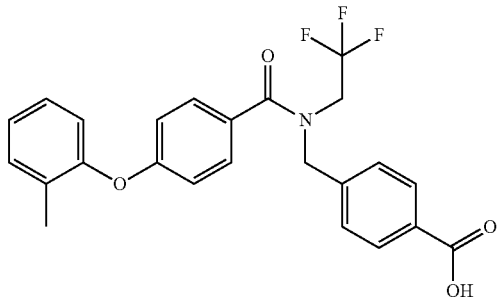 [SMILES: Cc1ccccc1Oc1ccc(C(=O)N(Cc2ccc(C(=O)O)cc2)CC(F)(F)F)cc1]

Prepared from the parent methyl ester (Intermediate C40f) using Method H1.

¹H NMR (400 MHz, CDCl₃) δ ppm 2.18 (s, 3H) 4.02 (br s, 2H) 4.85 (br s, 2H) 6.81-7.58 (m, 10H) 8.00-8.20 (m, 2H)

MS ES⁺: 444

Example 71

4-((4-(2-Fluorophenoxy)-N-(3,3,3-trifluoropropyl)benzamido)methyl)benzoic acid

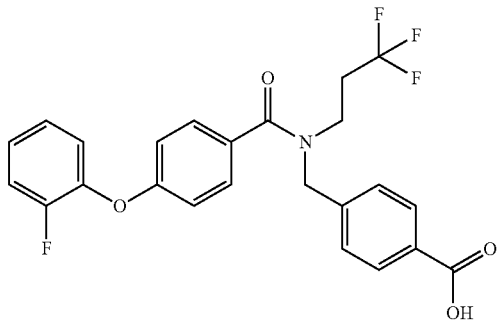 [SMILES: O=C(O)c1ccc(CN(CCC(F)(F)F)C(=O)c2ccc(Oc3ccccc3F)cc2)cc1]

Prepared from the parent methyl ester (Intermediate C25b) using Method H1.

¹H NMR (400 MHz, CDCl₃) δ ppm 2.35-2.65 (m, 2H) 3.53-3.68 (m, 2H) 4.60-4.78 (m, 2H) 6.88-7.45 (m, 10H) 8.06-8.13 (m, 2H)

MS ES⁺: 462

Example 72

4-((4-(2-Chlorophenoxy)-N-(2,2,2-trifluoroethyl)benzamido)methyl)benzoic acid

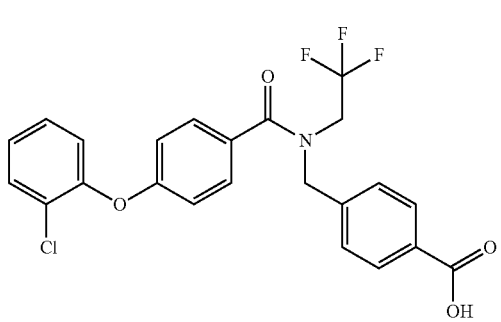 [SMILES: O=C(O)c1ccc(CN(CC(F)(F)F)C(=O)c2ccc(Oc3ccccc3Cl)cc2)cc1]

Prepared from the parent methyl ester (Intermediate C40g) using Method H1.
¹H NMR (400 MHz, CDCl₃) δ ppm 3.81-4.18 (m, 2H) 4.84 (br s, 2H) 6.88-7.57 (m, 10H) 8.01-8.16 (m, 2H)
MS ES⁺: 464

Example 73

4-((N-Ethyl-4-(o-tolyloxy)benzamido)methyl)benzoic acid

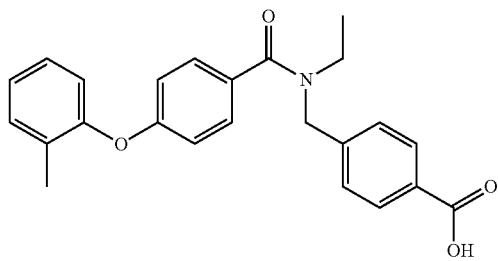 [SMILES: CCN(Cc1ccc(C(=O)O)cc1)C(=O)c1ccc(Oc2ccccc2C)cc1]

Prepared from the parent methyl ester (Intermediate C40h) using Method H1.
¹H NMR (400 MHz, DMSO-d₆) δ ppm 0.92-1.12 (m, 3H) 2.11 (s, 3H) 3.08-3.40 (m, 2H) 4.46-4.78 (m, 2H) 6.74-7.50 (m, 10H) 7.82-7.93 (m, 2H)
MS ES⁺: 390

Example 74

4-((N-(2,2-Difluoropropyl)-4-(2-fluorophenoxy)benzamido)methyl)benzoic acid

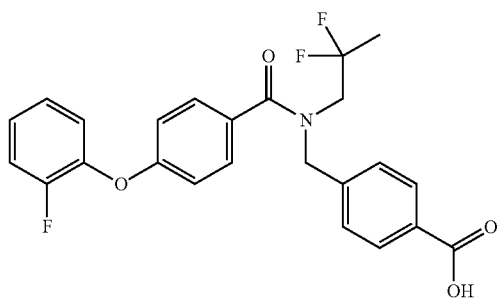 [SMILES: CC(F)(F)CN(Cc1ccc(C(=O)O)cc1)C(=O)c1ccc(Oc2ccccc2F)cc1]

Prepared from the parent methyl ester (Intermediate C25c) using Method H1.
¹H NMR (400 MHz, CDCl₃) δ ppm 1.24-1.92 (m, 3H) 3.36-4.08 (m, 2H) 4.57-5.13 (m, 2H) 6.79-7.58 (m, 10H) 7.90-8.20 (m, 2H)
MS ES⁺: 444

Example 75

4-((N-Butyl-4-(2-fluorophenoxy)benzamido)methyl)benzoic acid

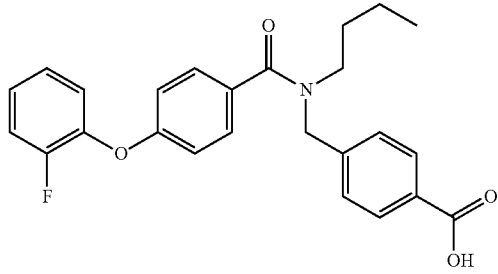 [SMILES: CCCCN(Cc1ccc(C(=O)O)cc1)C(=O)c1ccc(Oc2ccccc2F)cc1]

Prepared from the parent methyl ester (Intermediate C25d) using Method H1.
¹H NMR (400 MHz, CDCl₃) δ ppm 0.66-1.77 (m, 7H) 3.08-3.57 (m, 2H) 4.49-4.93 (m, 2H) 6.81-7.57 (m, 10H) 8.04-8.18 (m, 2H)
MS ES⁺: 422

Example 76

4-((4-(2-Chlorophenoxy)-N-ethylbenzamido)methyl)benzoic acid

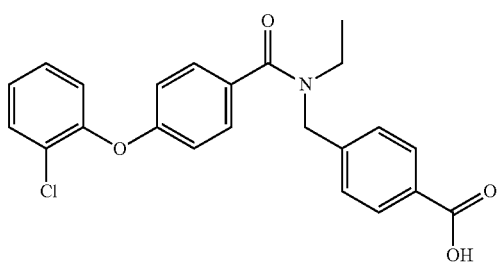 [SMILES: CCN(Cc1ccc(C(=O)O)cc1)C(=O)c1ccc(Oc2ccccc2Cl)cc1]

Prepared from the parent methyl ester (Intermediate C40i) using Method H1.
¹H NMR (400 MHz, DMSO-d₆) δ ppm 0.78-1.23 (m, 3H) 2.98-3.65 (m, 2H) 4.40-4.82 (m, 2H) 6.70-7.70 (m, 1 OH) 7.77-8.01 (m, 2H)
MS ES⁺: 410

Example 77

4-((N-(Cyclopropylmethyl)-5-(2-fluorophenoxy)picolinamido)methyl)benzoic acid

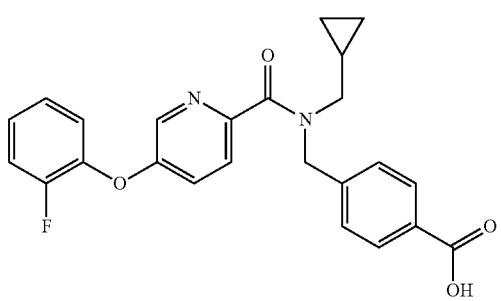 [SMILES: O=C(O)c1ccc(CN(CC2CC2)C(=O)c2ccc(Oc3ccccc3F)cn2)cc1]

Prepared from the parent methyl ester (Intermediate C69) using Method H1.
¹H NMR (400 MHz, CDCl₃) δ ppm −0.06-0.25 (m, 2H) 0.38-0.56 (m, 2H) 0.77-1.33 (m, 1H) 3.27-3.40 (m, 2H) 4.99 (s, 2H) 7.07-8.44 (m, 11H)
MS ES⁺: 421

Example 78

4-((4-(2-Chlorophenoxy)-N-(2,2-difluoroethyl)benzamido)methyl)benzoic acid

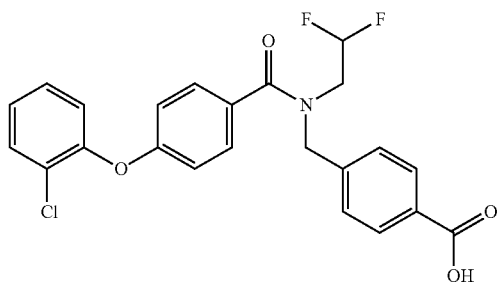 [SMILES: O=C(O)c1ccc(CN(CC(F)F)C(=O)c2ccc(Oc3ccccc3Cl)cc2)cc1]

Prepared from the parent methyl ester (Intermediate C40j) using Method H1.

$^1$H NMR (400 MHz, CDCl$_3$) δ ppm 3.59-3.81 (m, 2H) 4.80 (br s, 2H) 5.05-6.40 (m, 1H) 6.81-7.53 (m, 10H) 8.04-8.17 (m, 2H)

MS ES$^+$: 446

Example 79

4-((N-(Cyclopropylmethyl)-4-(5-fluoro-2-methoxyphenoxy)benzamido)methyl)benzoic acid

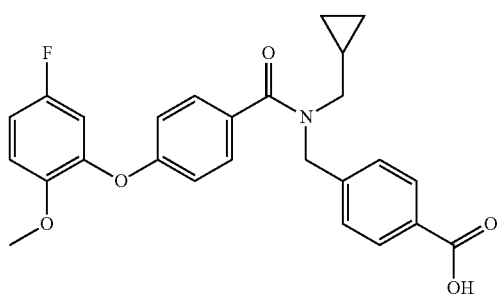 [SMILES: COc1ccc(F)cc1Oc1ccc(C(=O)N(Cc2ccc(C(=O)O)cc2)CC2CC2)cc1]

Prepared from the parent methyl ester (Intermediate C67b) using Method H1.

$^1$H NMR (400 MHz, CDCl$_3$) δ −0.12-0.32 (m, 2H) 0.41-0.58 (m, 2H) 0.78-1.15 (m, 1H) 3.02-3.52 (m, 2H) 3.78 (s, 3H) 4.68-5.08 (m, 2H) 6.69-7.08 (m, 5H) 7.19-7.58 (m, 4H) 8.04-8.12 (m, 2H)

MS ES$^+$: 450

Example 80

4-((4-(4-Fluoro-2-methoxyphenoxy)-N-propylbenzamido)methyl)benzoic acid

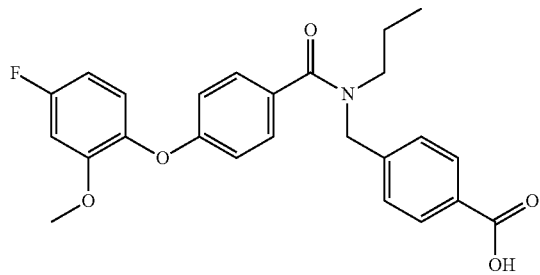 [SMILES: CCCN(Cc1ccc(C(=O)O)cc1)C(=O)c1ccc(Oc2ccc(F)cc2OC)cc1]

Prepared from the parent methyl ester (Intermediate C67a) using Method H1.

$^1$H NMR (300 MHz, CDCl$_3$) δ ppm 0.65-1.08 (m, 3H) 1.47-1.74 (m, 2H) 3.10-3.50 (m, 2H), 3.77 (s, 3H) 4.55-4.98 (m, 2H) 6.58-7.58 (m, 91H) 7.90-8.23 (m, 2H)

MS ES$^+$: 438

Example 81

4-((4-(5-Fluoro-2-methoxyphenoxy)-N-propylbenzamido)methyl)benzoic acid

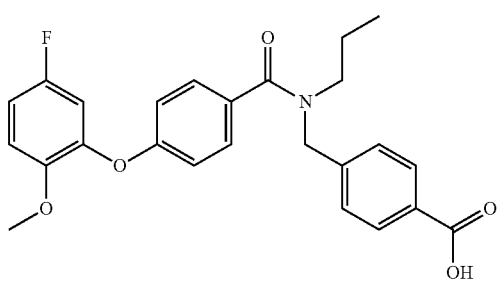 [SMILES: CCCN(Cc1ccc(C(=O)O)cc1)C(=O)c1ccc(Oc2cc(F)ccc2OC)cc1]

Prepared from the parent methyl ester (Intermediate C67c) using Method H1.

$^1$H NMR (400 MHz, CDCl$_3$) δ ppm 0.65-1.12 (m, 3H) 1.40-1.84 (m, 2H) 3.03-3.58 (m, 2H), 3.78 (s, 3H) 4.48-5.01 (m, 2H) 6.67-7.12 (m, 5H) 7.20-7.67 (m, 4H) 8.00-8.22 (m, 2H)

MS ES$^+$: 438

Example 82

4-((N-(Cyclopropylmethyl)-4-(3-fluoro-2-methoxyphenoxy)benzamido)methyl)benzoic acid

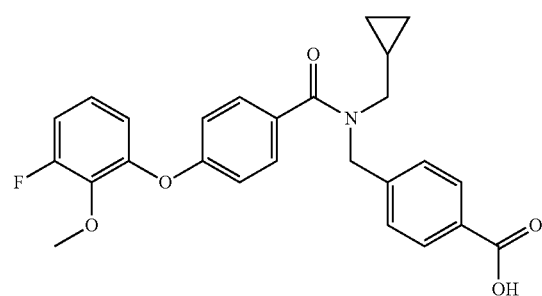 [SMILES: COc1c(F)cccc1Oc1ccc(C(=O)N(Cc2ccc(C(=O)O)cc2)CC2CC2)cc1]

Prepared from the parent methyl ester (Intermediate C67d) using Method H1.

$^1$H NMR (400 MHz, CDCl$_3$) δ −0.09-0.27 (m, 2H) 0.42-0.58 (m, 2H) 0.78-1.15 (m, 1H) 3.03-3.55 (m, 2H) 3.86 (s, 3H) 4.70-5.08 (m, 2H) 6.72-6.87 (m, 1H) 6.87-7.08 (m, 4H) 7.22-7.58 (m, 4H) 8.03-8.12 (m, 2H)

MS ES$^+$: 450

Example 83

4-((N-(Cyclopropylmethyl)-5-(2-fluorophenoxy)pyrimidine-2-carboxamido)methyl)benzoic acid

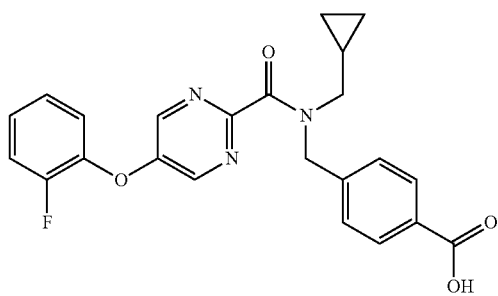 [SMILES: O=C(O)c1ccc(CN(CC2CC2)C(=O)c2ncc(Oc3ccccc3F)cn2)cc1]

Prepared from the parent methyl ester (Intermediate C72) using Method H1.

$^1$H NMR (400 MHz, CDCl$_3$) δ −0.06-0.20 (m, 2H) 0.38-0.57 (m, 2H) 0.91-1.14 (m, 1H) 3.01-3.43 (m, 2H) 4.64-5.06 (m, 2H), 7.12-7.33 (m, 4H) 7.40-7.53 (m, 2H) 8.01-8.10 (m, 2H) 8.38-8.57 (m, 2H)

MS ES$^+$: 422

Example 84

4-((N-(Cyclopropylmethyl)-5-(2-methoxyphenoxy)pyrimidine-2-carboxamido)methyl)benzoic acid

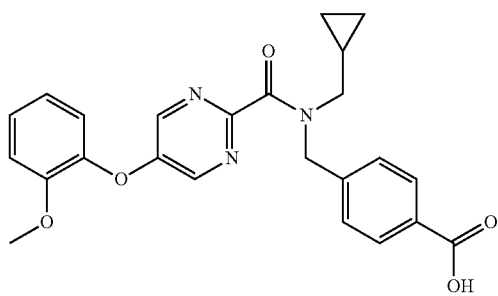 [SMILES: COc1ccccc1Oc1cnc(C(=O)N(Cc2ccc(C(=O)O)cc2)CC2CC2)nc1]

Prepared from the parent methyl ester (Intermediate C73) using Method H1.

$^1$H NMR (300 MHz, DMSO-d$_6$) δ −0.12-0.20 (m, 2H) 0.26-0.42 (m, 2H) 0.76-1.12 (m, 1H) 2.82-3.30 (m, 2H) 3.68-3.76 (m, 3H) 4.35-4.79 (m, 2H), 6.95-7.34 (m, 6H) 7.69-7.82 (m, 2H) 8.39-8.49 (m, 2H)

MS ES$^+$: 434

Example 85

4-((5-(2-Methoxyphenoxy)-N-propylpyrimidine-2-carboxamido)methyl)benzoic acid

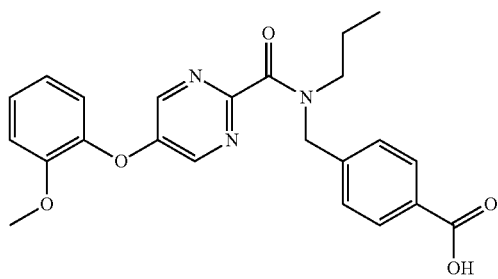 [SMILES: CCCN(Cc1ccc(C(=O)O)cc1)C(=O)c1ncc(Oc2ccccc2OC)cn1]

Prepared from the parent methyl ester (Intermediate C74) using Method H1.

$^1$H NMR (400 MHz, CDCl$_3$) δ ppm 0.63-0.99 (m, 3H) 1.48-1.77 (m, 2H) 3.03-3.50 (m, 2H), 3.71-3.86 (m, 3H) 4.49-4.93 (m, 2H) 6.93-7.53 (m, 6H) 7.96-8.14 (m, 2H) 8.28-8.52

MS ES$^+$: 422

3. Biological Efficacy of Compounds of the Invention

In Vitro LPA5 Receptor Assay

Engagement of the LPA5 receptor by its ligand, oleoyl-L-α-lysophosphatidic acid (LPA), leads to the release of intracellular stores of calcium into the cytoplasm mediated through a Gq-driven increase in inositol triphosphate (IP3) levels. Gq is a heterotrimeric G protein subunit that activates phospholipase C.

The ability of test compounds to prevent LPA-driven intracellular release of stored calcium from RH7777 cells expressing human LPA5 receptors was assayed by stimulating the cells with LPA in the presence of various test compounds to measure the test compounds' antagonism, i.e. activity in vitro.

Approximately 10,000 cells in normal culture medium (Minimal Essential Media, 10% Foetal Calf Serum) were dispensed per assay well in a black clear bottom poly-D-lysine coated 384 well plate (Corning). Cells were allowed to settle for thirty minutes at room temperature before being incubated overnight at 37° C., 5% CO$_2$. Sixteen to twenty hours after dispensing, the cells were loaded with a calcium-sensitive fluorescent dye by replacing the culture medium with assay buffer (1× Hanks buffered saline, 25 mM HEPES, 0.1% w/v fatty acid free BSA (bovine serum albumin), pH7.4) containing 1.25 mM probenecid and 1× Calcium 5 Reagent (Molecular Devices). Cells were incubated at 37° C. for one hour to allow for dye uptake.

To test for antagonist activity, test compounds at a final concentration range between 0.32 nM-10 µM (diluted in assay buffer) were added to the assay wells and allowed to incubate for fifteen minutes. After incubation with test compounds the assay plate was placed in a FLIPR Tetra system (Molecular Devices) and LPA (diluted in assay buffer) was added to give a final concentration equivalent to its determined EC$_{90}$ against LPA5 receptor. Ligand-dependent changes in intracellular calcium levels were determined by measuring changes in fluorescence of the dye over 515-575 nM following excitation over 470-495 nM. Readings from control wells that did not contain test compounds enabled percentage inhibition curves to be plotted using a 4-parameter curve fit algorithm and IC$_{50}$ values to be calculated for each compound.

Results

| Example No. | Mean IC$_{50}$ (nM) | Example No. | Mean IC$_{50}$ (nM) |
|---|---|---|---|
|  |  | 1 | 840 |
| 2 | 690 | 3 | 43 |
| 4 | 63 | 5 | 16 |
| 6 | 24 | 7 | 31 |
| 8 | 32 | 9 | 15 |
| 10 | 48 | 11 | 6 |
| 12 | 9 | 13 | 3 |
| 14 | 2 | 15 | 120 |
| 16 | 1 | 17 | 1 |
| 18 | 2 | 19 | 9 |
| 20 | 40 | 21 | 11 |
| 22 | 24 | 23 | 44 |
| 24 | 7 | 25 | 29 |
| 26 | 260 | 27 | 200 |
| 28 | 45 | 29 | 43 |
| 30 | 12 | 31 | 5 |
| 32 | 0.4 | 33 | 0.4 |
| 34 | 460 | 35 | 7 |
| 36 | 24 | 37 | 28 |
| 38 | 140 | 39 | 11 |
| 40 | 31 | 41 | 89 |
| 42 | 17 | 43 | 58 |
| 44 | 11 | 45 | 99 |
| 46 | 17 | 47 | 11 |
| 48 | 3300 | 49 | 4600 |
| 50 | 3600 | 51 | 53 |
| 52 | 370 | 53 | 58 |
| 54 | 26 | 55 | 690 |
| 56 | 180 | 57 | 410 |
| 58 | 32 | 59 | 6 |
| 60 | 60 | 61 | 8 |
| 62 | 9 | 63 | 10 |
| 64 | 7 | 65 | 4 |
| 66 | 5 | 67 | 5 |
| 68 | 10 | 69 | 8 |
| 70 | 140 | 71 | 83 |
| 72 | 42 | 73 | 890 |
| 74 | 98 | 75 | 22 |
| 76 | 140 | 77 | 74 |
| 78 | 170 | 79 | 68 |
| 80 | 45 | 83 | 350 |
| 84 | 91 | 85 | 120 |

In Vivo Farnesyl Pyrophosphate-Induced Inflammatory Model

Farnesyl pyrophosphate (FPP) is an endogenous ligand for the LPA5 receptor, with a reported in-vitro EC$_{50}$ of 49 nM and 3-fold selectivity over other LPA receptors (Williams et al. (2009), 'Unique Ligand Selectivity of the GPR92/LPA5 Lysophosphatidate Receptor Indicates Role in Human Platelet Activation', J Biol. Chem., 284(25):17304-17319). The FPP-induced hyperalgesia model is a pharmacodynamic rat model which involves inducing pain by injecting FPP, an agonist of LPA5 receptor, into the plantar surface of the hindpaw. Pre-treatment with a LPA5 receptor antagonist prevents the hyperalgesia induced by FPP.

In adult male rats baseline measurements were taken by assessing the withdrawal threshold to a painful pressure stimulus applied to the hindpaw according to the Randall-Selitto method (Randall and Selitto (1957), 'A method for measurement of analgesic activity on inflamed tissue', Arch Int Pharmacodyn Ther., 111(4):409-19). The animals were then administered an intraperitoneal (ip) or oral (po) dose of test compound or vehicle 30 to 120 minutes prior to an intra-plantar injection of FPP (100 µL at 32 nM) or saline vehicle. Withdrawal responses were reassessed at 30 and 90 minutes after injection of FPP in the ipsilateral paw.

Results

| Compound of Example No. | Route | In vivo efficacy (minimum effective dose (MED) mg/kg) |
|---|---|---|
| 3 | po | ≤10 |
| 4 | po | ≤10 |
| 4 | ip | 1 |
| 5 | po | ≤10 |
| 5 | ip | 0.3 |
| 8 | po | 100 |
| 11 | po | ≤10 |
| 24 | po | 30 |
| 29 | po | 3 |
| 31 | po | 1 |
| 40 | po | 60 |

In Vitro LPA1 Receptor Assay

Engagement of the LPA1 receptor by its ligand, oleoyl-L-α-lysophosphatidic acid (LPA), leads to the release of intracellular stores of calcium into the cytoplasm mediated through a Gq-driven increase in inositol triphosphate (IP3) levels. Gq is a heterotrimeric G protein subunit that activates phospholipase C.

The ability of test compounds to prevent LPA-driven intracellular release of stored calcium from RH7777 cells expressing human LPA1 receptors was assayed by stimulating the cells with LPA in the presence of various test compounds to measure the test compounds' antagonism, i.e. activity in vitro.

Approximately 10,000 cells in normal culture medium (Dulbecco's Modified Eagle Media, 10% Foetal Calf Serum) were dispensed per assay well in a black clear bottom collagen coated 384 well plate (Beckton Dickinson). Cells were allowed to settle for thirty minutes at room temperature before being incubated overnight at 37° C., 5% $CO_2$. Sixteen to twenty hours after dispensing, the cells were loaded with a calcium-sensitive fluorescent dye by replacing the culture medium with assay buffer (1× Hanks buffered saline, 25 mM HEPES, 0.1% w/v fatty acid free BSA (bovine serum albumin), pH7.4) containing 1.25 mM probenecid and 1× Calcium 5 Reagent (Molecular Devices). Cells were incubated at 37° C. for one hour to allow for dye uptake.

To test for antagonist activity, test compounds at a final concentration range between 0.32 nM-10 µM (diluted in assay buffer) were added to the assay wells and allowed to incubate for twenty five minutes. After incubation with test compounds the assay plate was placed in a FLIPR Tetra system (Molecular Devices) and LPA (diluted in assay buffer) was added to give a final concentration equivalent to its determined EC$_{80}$ against LPA1 receptor. Ligand-dependent changes in intracellular calcium levels were determined by measuring changes in fluorescence of the dye over 515-575 nM following excitation over 470-495 nM. Readings from control wells that did not contain test compounds enabled percentage inhibition curves to be plotted using a 4-parameter curve fit algorithm and IC$_{50}$ values to be calculated for each compound.

| Example No. | Mean IC$_{50}$ (nM) | Example No. | Mean IC$_{50}$ (nM) |
|---|---|---|---|
| 3 | 35 | 4 | 49 |
| 5 | 46 | 8 | 46 |
| 11 | 6 | 13 | 4 |
| 14 | 2 | 17 | 0.4 |
| 18 | 1 | 19 | 7 |

-continued

| Example No. | Mean IC$_{50}$ (nM) | Example No. | Mean IC$_{50}$ (nM) |
|---|---|---|---|
| 20 | 12 | 22 | 30 |
| 24 | 11 | 25 | 14 |
| 28 | 46 | 29 | 34 |
| 30 | 12 | 31 | 4 |
| 32 | 2 | 33 | 0.3 |
| 36 | 24 | 37 | 25 |
| 38 | 36 | 40 | 160 |
| 45 | 75 | 46 | 19 |
| 47 | 22 | 54 | 27 |
| 58 | 17 | | |
| 60 | 33 | 61 | 4 |
| 62 | 5 | 63 | 7 |
| 64 | 9 | 65 | 5 |
| 66 | 7 | 67 | 7 |
| 68 | 13 | 69 | 12 |
| 70 | 47 | 71 | 59 |
| 72 | 29 | 73 | 120 |
| 74 | 40 | 75 | 31 |
| 76 | 130 | 77 | 86 |
| 78 | 390 | 79 | 94 |
| 80 | 110 | 83 | 540 |
| 84 | 170 | 85 | 180 |

In Vivo Bleomycin Induced Scleroderma Model
Experimental Outline

Adult male C57BL/6 mice, aged 8-10 weeks, were assigned to groups and allowed to acclimatise for a week. On Day −1, the back skin of the animals was shaved. From Day 0, animals were administered with 100 μl of a 1 mg/ml solution of bleomycin sulphate in phosphate buffered saline (PBS) by intradermal injection in the shaved skin. Injections were repeated in a one square centimeter area every other day for four weeks. A group of ten animals (Control group) was injected with an identical volume of PBS. Treatments were given according to the administration schedule shown in the table below. Animals were weighed at the beginning of the experiment on Day 0 and then twice weekly throughout the study. At the end of the experiment, on Day 28, animals were culled and samples of back skin were taken for further analysis. All groups were n=10; the vehicle was distilled water and the administration volume was 10 ml/kg for oral gavage (p.o.); administration volume was 25 μl for topical application.

| Group | Substance | Dose | Route | Administration Frequency | Skin sensitisation |
|---|---|---|---|---|---|
| 1 | Vehicle | n/a | p.o. | BID, Day 0-Day 28 | PBS, i.d., QAD, Day 0-Day 28 |
| 2 | Vehicle | n/a | p.o. | BID, Day 0-Day 28 | Bleomycin, i.d., QAD, Day 0-Day 28 |
| 3 | Imatinib mesylate | 150 mg/kg | p.o. | BID, Day 0-Day 28 | |
| 4 | Compound of Example 5 | 30 mg/kg | p.o. | BID, Day 0-Day 28 | |
| 5 | Compound of Example 5 | 30 mg/kg | p.o. | BID, Day 14-Day 28 | |
| 6 | "Protopic" (trade mark) | 0.1% | topical | BID, Day 0-Day 28 | |
| 7 | Betamethasone | 0.1% | topical | BID, Day 0-Day 9 SID, Day 10-Day 28 | |

Results

Bodyweights were graphed along with the standard error of the mean (SEM); Skin samples (two punch biopsies per animal, 4 mm in diameter each) samples were hydrolyzed and hydroxyproline content of the samples was determined from analysis in a semi-automated process using a continuous flow analyzer. Autoanalyser readings were calibrated against hydroxyproline standards and collagen content calculated. The bodyweight loss observed in the Example 5 compound-treated groups did not differ from the bodyweight loss observed in the vehicle-treated group. Some weight loss<10% was observed with bleomycin treatment. Bleomycin administration induced a highly significant increase in skin collagen content when compared to the control, saline-injected, group (p<0.01). Imatinib and Betamethasone 0.1% induced a non-significant reduction in skin collagen content when compared to the vehicle-treated group. The Example 5 compound administered from Day 0 and from Day 14 induced a significant reduction in skin collagen content when compared to the vehicle-treated group (p<0.05). Protopic 0.1% induced a highly significant reduction in skin collagen content when compared to the vehicle-treated group (p<0.001). Thus, the compound of Example 5 demonstrated an anti-fibrotic effect in an in vivo bleomycin-induced scleroderma model as measured by collagen skin content.

The invention claimed is:

1. A compound of formula (I), or a pharmaceutically acceptable salt thereof:

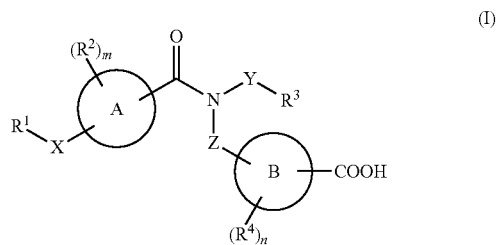

wherein

R$^1$ represents a C$_5$-C$_{10}$ aryl group substituted by at least one substituent chosen from halogen, cyano, nitro, carboxyl, hydroxyl, C$_3$-C$_6$ cycloalkyl, C$_1$-C$_6$ alkoxy, C$_1$-C$_6$ alkoxycarbonyl, C$_1$-C$_6$ alkoxycarbonylamino, C$_1$-C$_6$ haloalkoxy, —NR$^5$R$^6$, C$_3$-C$_6$ cycloalkylamino, C$_1$-C$_6$ alkylthio, C$_1$-C$_6$ alkylcarbonyl, C$_1$-C$_6$ alkylcarbonyloxy, C$_1$-C$_6$ alkylcarbonylamino, sulphonamido, C$_1$-C$_6$ alkylsulphonyl, C$_1$-C$_6$ alkylsulphonylamino, —C(O)NR$^7$R$^8$, C$_1$-C$_6$ alkyl, or a saturated or unsaturated 5- to 6-membered carbocyclic or heterocyclic ring comprising at least one heteroatom chosen from nitrogen, oxygen, or sulphur, wherein the alkyl group is unsubstituted or substituted by at least one halogen, hydroxyl, carboxyl, or $C_1$-$C_6$ alkoxycarbonyl group, and wherein the 5- to 6-membered carbocyclic or heterocyclic ring is unsubstituted or substituted by at least one substituent chosen from halogen, hydroxyl, oxo, carboxyl, cyano, $C_1$-$C_6$ alkyl, $C_1$-$C_6$ alkoxycarbonyl, or $C_1$-$C_6$ hydroxyalkyl;

X is chosen from an oxygen atom, —$CH_2$—, —$OCH_2$—, —$CH_2O$—, —$CH_2CH_2$—, —$CH_2NR^{17}$—, —$NR^{17}CH_2$—, —CHF—, or —$CF_2$—;

m is chosen from 0, 1, or 2;

each $R^2$ is independently chosen from a halogen atom, a hydroxyl, $C_1$-$C_6$ alkyl, difluoromethyl, trifluoromethyl, $C_1$-$C_6$ alkoxy, difluoromethoxy, trifluoromethoxy, or $NR^{15}R^{16}$ group;

Y represents $CR^9R^{10}$, wherein $R^9$ and $R^{10}$ are each independently chosen from a hydrogen atom or a methyl group;

$R^3$ is chosen from $C_1$-$C_8$ alkyl, $C_2$-$C_8$ alkenyl, or a saturated or unsaturated 3- to 10-membered carbocyclic or heterocyclic ring system comprising at least one ring heteroatom chosen from nitrogen, oxygen, or sulphur, wherein the alkyl, alkenyl, carbocyclic and heterocyclic ring systems are unsubstituted or substituted by at least one substituent chosen from halogen, cyano, hydroxyl, $C_3$-$C_6$ cycloalkyl, $C_1$-$C_6$ alkoxy, $C_5$-$C_6$ aryloxy, $C_5$-$C_6$aryl$C_1$-$C_6$alkyloxy, $C_1$-$C_6$ alkoxycarbonyl, $C_1$-$C_6$ alkoxycarbonylamino, $C_1$-$C_6$ alkoxycarbonyloxy, $C_1$-$C_6$ haloalkyl, $C_1$-$C_6$ haloalkoxy, —$NR^{13}R^{14}$, $C_3$-$C_6$ cycloalkylamino, $C_1$-$C_6$ alkylthio, $C_1$-$C_6$ alkylcarbonyl, $C_1$-$C_6$ alkylcarbonyloxy, $C_1$-$C_6$ alkylcarbonylamino, sulphonamido, $C_1$-$C_6$ alkylsulphonyl, $C_1$-$C_6$ alkylsulphonylamino, $C_1$-$C_6$ alkyl, or a saturated or unsaturated 3- to 10-membered carbocyclic or heterocyclic ring system comprising at least one ring heteroatom chosen from nitrogen, oxygen, or sulphur, wherein the carbocyclic or heterocyclic ring system is unsubstituted or substituted by least one substituent chosen from halogen, hydroxyl, oxo, carboxyl, cyano, $C_1$-$C_6$ alkyl, $C_1$-$C_6$ alkoxy, $C_1$-$C_6$ alkoxycarbonyl, or $C_1$-$C_6$ hydroxyalkyl;

and wherein the 3- to 10-membered carbocyclic or heterocyclic ring systems are monocyclic or polycyclic;

Z represents $CR^{11}R^{12}$, wherein $R^{11}$ and $R^{12}$ are each independently chosen from a hydrogen atom or a methyl group, with the proviso that both cannot simultaneously represent a methyl group;

n is chosen from 0, 1, or 2;

each $R^4$ is independently chosen from a halogen atom, hydroxyl, $C_1$-$C_6$ alkyl, difluoromethyl, trifluoromethyl, $C_1$-$C_6$ alkoxy, difluoromethoxy, trifluoromethoxy, or $NR^{18}R^{19}$ group;

$R^5$ and $R^6$ are each independently chosen from a hydrogen atom or a $C_1$-$C_6$ alkyl group, or $R^5$ and $R^6$ together with the nitrogen atom to which they are attached form a 4- to 7-membered saturated heterocycle;

$R^7$ and $R^8$ are each independently chosen from a hydrogen atom or a $C_1$-$C_6$ alkyl group, or $R^7$ and $R^8$ together with the nitrogen atom to which they are attached form a 4- to 7-membered saturated heterocycle;

$R^{13}$ and $R^{14}$ are each independently chosen from a hydrogen atom or a $C_1$-$C_6$ alkyl group, or $R^{13}$ and $R^{14}$ together with the nitrogen atom to which they are attached form a 4- to 7-membered saturated heterocycle;

$R^{15}$ and $R^{16}$ are each independently chosen from a hydrogen atom or a $C_1$-$C_6$ alkyl group, or $R^{15}$ and $R^{16}$ together with the nitrogen atom to which they are attached form a 4- to 7-membered saturated heterocycle;

$R^{17}$ is chosen from a hydrogen atom or a $C_1$-$C_6$ alkyl group;

$R^{18}$ and $R^{19}$ are each independently chosen from a hydrogen atom or a $C_1$-$C_6$ alkyl group, or $R^{18}$ and $R^{19}$ together with the nitrogen atom to which they are attached form a 4 to 7-membered saturated heterocycle; and A and B are each independently chosen from a saturated or unsaturated 5- to 10-membered carbocyclic or heterocyclic ring system comprising at least one ring heteroatom chosen from nitrogen, oxygen, or sulphur, wherein the 5- to 10-membered carbocyclic or heterocyclic ring system is monocyclic or polycyclic.

2. The compound according to claim 1, wherein $R^1$ represents a $C_5$-$C_{10}$ aryl group substituted by one or two substituents independently chosen from halogen, cyano, $C_1$-$C_2$ alkoxy, or $C_1$-$C_2$ alkyl unsubstituted or substituted by at least one halogen atom.

3. The compound according to claim 1, wherein X is chosen from an oxygen atom or —$CH_2O$—.

4. The compound according to claim 1, wherein each $R^2$ is independently chosen from a halogen atom or a $C_1$-$C_6$ alkyl group.

5. The compound according to claim 1, wherein Y represents $CH_2$.

6. The compound according to claim 1, wherein $R^3$ represents a $C_1$-$C_3$ alkyl group.

7. The compound according to claim 1, wherein $R^3$ represents a saturated or unsaturated 3- to 6-membered carbocyclic or heterocyclic ring comprising at least one heteroatom chosen from nitrogen, oxygen, or sulphur.

8. The compound according to claim 6, wherein $R^3$ represents a $C_1$-$C_3$ alkyl group unsubstituted or substituted by at least one substituent chosen from fluorine, chlorine, hydroxyl, $C_3$-$C_6$ cycloalkyl, $C_1$-$C_2$ alkoxy, phenoxy, benzyloxy, trifluoromethyl, $C_1$-$C_2$ alkyl, or a saturated or unsaturated 3- to 6-membered carbocyclic or heterocyclic ring comprising at least one heteroatom chosen from nitrogen, oxygen, or sulphur, wherein the carbocyclic or heterocyclic ring is unsubstituted or substituted by least one substituent chosen from halogen, $C_1$-$C_2$ alkyl, or $C_1$-$C_2$ alkoxy.

9. The compound according to claim 1, wherein Z represents $CH_2$.

10. The compound according to claim 1, wherein n is chosen from 0 or 1, and $R^4$ is chosen from a halogen atom, $C_1$-$C_6$ alkyl, or $C_1$-$C_6$ alkoxy group.

11. The compound according to claim 1, wherein A and B are each independently chosen from cyclopentyl, cyclohexyl, cyclopentenyl, cyclohexenyl, phenyl, pyrrolidinyl, piperidinyl, piperazinyl, morpholinyl, thiomorpholinyl, oxadiazolyl, tetrahydrofuranyl, naphthyl, benzofuranyl, benzothienyl, benzodioxolyl, benzoxazolyl, quinolinyl, oxazolyl, thiadiazolyl, 2,3-dihydrobenzofuranyl, tetrahydropyranyl, pyrazolyl, imidazo[1,2-a]pyridinyl, pyrazinyl, thiazolidinyl, indanyl, thienyl, isoxazolyl, pyridazinyl, pyrrolyl, furanyl, thiazolyl, isothiazolyl, indolyl, isoindolyl, imidazolyl, pyrimidinyl, benzimidazolyl, triazolyl, tetrazolyl, or pyridinyl.

12. The compound according to claim 1, wherein A and B each represent phenyl.

13. A compound chosen from:
4-((N-Ethyl-4-(2-fluorophenoxy)benzamido)methyl)benzoic acid,
4-((N-(2,2-Difluoroethyl)-4-(2-fluorophenoxy)benzamido)methyl)benzoic acid,
4-((4-(2-Fluorophenoxy)-N-(2,2,2-trifluoroethyl)benzamido)methyl)benzoic acid,
4-((4-(2-Fluorophenoxy)-N-isobutylbenzamido)methyl)benzoic acid,
4-((N-(Cyclopropylmethyl)-4-(2-fluorophenoxy)benzamido)methyl)benzoic acid,
4-((N-(Cyclobutylmethyl)-4-(2-fluorophenoxy)benzamido)methyl)benzoic acid,
4-((4-(2-Fluorophenoxy)-N-((3-methoxycyclobutyl)methyl)benzamido)-methyl)benzoic acid,
4-((4-(2-Fluorophenoxy)-N-isopentylbenzamido)methyl)benzoic acid,
4-((N-(2-Cyclopropylethyl)-4-(2-fluorophenoxy)benzamido)methyl)benzoic acid,
4-((N-(2-Cyclobutylethyl)-4-(2-fluorophenoxy)benzamido)methyl)benzoic acid,
4-((N-Benzyl-4-(2-fluorophenoxy)benzamido)methyl)benzoic acid,
4-((N-(2-Fluorobenzyl)-4-(2-fluorophenoxy)benzamido)methyl)benzoic acid,
4-((4-(2-Fluorophenoxy)-N-(3-methoxybenzyl)benzamido)methyl)benzoic acid,
4-((4-(2-Fluorophenoxy)-N-(4-ethoxybenzyl)benzamido)methyl)benzoic acid,
4-((4-(2-Fluorophenoxy)-N-phenethylbenzamido)methyl)benzoic acid,
4-((4-(2-Fluorophenoxy)-N-(3-(2-fluorophenyl)propyl)benzamido)-methyl)benzoic acid,
4-((4-(2-Fluorophenoxy)-N-(3-(3-fluorophenyl)propyl)benzamido)-methyl)benzoic acid,
4-((4-(2-Fluorophenoxy)-N-((trans-2-phenylcyclopropyl)methyl)-benzamido)methyl)benzoic acid,
(S)-4-((4-(2-Fluorophenoxy)-N-(2-hydroxy-3-phenylpropyl)-benzamido)methyl)benzoic acid,
(R)-4-((4-(2-Fluorophenoxy)-N-(2-hydroxy-3-phenylpropyl)benzamido)-methyl)benzoic acid,
4-((4-(2-Fluorophenoxy)-N-(4-phenylbutyl)benzamido)methyl)benzoic acid,
4-((N-(Cyclopropylmethyl)-4-(o-tolyloxy)benzamido)methyl)benzoic acid,
4-((N-(Cyclobutylmethyl)-4-(o-tolyloxy)benzamido)methyl)benzoic acid,
4-((N-Benzyl-4-(o-tolyloxy)benzamido)methyl)benzoic acid,
4-((N-Phenethyl-4-(o-tolyloxy)benzamido)methyl)benzoic acid,
4-((N-Phenethyl-4-(2-(trifluoromethyl)phenoxy)benzamido)methyl)benzoic acid,
4-((N-Benzyl-4-(2-cyanophenoxy)benzamido)methyl)benzoic acid,
4-((N-Ethyl-4-(2-methoxyphenoxy)benzamido)methyl)benzoic acid,
4-((N-(2,2-Difluoroethyl)-4-(2-methoxyphenoxy)benzamido)methyl)benzoic acid,
4-((N-Isobutyl-4-(2-methoxyphenoxy)benzamido)methyl)benzoic acid,
4-((N-(Cyclopropylmethyl)-4-(2-methoxyphenoxy)benzamido)-methyl)benzoic acid,
4-((4-(2-Methoxyphenoxy)-N-(3-phenylpropyl)benzamido)methyl)benzoic acid,
4-((N-(3-(3-Fluorophenyl)propyl)-4-(2-methoxyphenoxy)benzamido)-methyl)benzoic acid,
4-((N-(Cyclopropylmethyl)-4-(2-ethoxyphenoxy)benzamido)methyl)benzoic acid,
4-((4-(2-Chlorophenoxy)-N-(cyclopropylmethyl)benzamido)methyl)benzoic acid,
4-((4-(2-Chlorophenoxy)-N-phenethylbenzamido)methyl)benzoic acid,
4-((N-(Cyclopropylmethyl)-4-(2,6-difluorophenoxy)benzamido)-methyl)benzoic acid,
4-((N-(2-Cyclopropylethyl)-4-(2,6-difluorophenoxy)benzamido)-methyl)benzoic acid,
4-((N-Benzyl-4-(2,6-difluorophenoxy)benzamido)methyl)benzoic acid,
4-((N-(Cyclopropylmethyl)-4-(2-fluoro-6-methylphenoxy)benzamido)-methyl)benzoic acid,
4-((4-(Cyclobutylmethyl)-4-(2-fluoro-6-methylphenoxy)benzamido)-methyl)benzoic acid,
4-((4-(2-Chloro-6-fluorophenoxy)-N-(cyclopropylmethyl)benzamido)-methyl)benzoic acid,
4-((4-(2-Chloro-6-fluorophenoxy)-N-(2-cyclopropylethyl)benzamido)-methyl)benzoic acid,
4-((N-Benzyl-4-(2-chloro-6-fluorophenoxy)benzamido)methyl)benzoic acid,
4-((4-(2,6-Dimethylphenoxy)-N-isopentylbenzamido)methyl)benzoic acid,
4-((N-Benzyl-4-(2,6-dimethylphenoxy)benzamido)methyl)benzoic acid,
4-((4-(2,6-Dimethylphenoxy)-N-phenethylbenzamido)methyl)benzoic acid,
4-((4-(3-Methoxyphenoxy)-N-phenethylbenzamido)methyl)benzoic acid,
4-((4-(4-Methoxyphenoxy)-N-phenethylbenzamido)methyl)benzoic acid,
4-((4-(3-Chlorophenoxy)-N-phenethylbenzamido)methyl)benzoic add,
4-((N-(Cyclopropylmethyl)-4-((2-fluorobenzyl)oxy)benzamido)-methyl)benzoic add,
4-((N-(Cyclobutylmethyl)-4-((2-fluorobenzyl)oxy)benzamido)-methyl)benzoic add,
4-((N-Benzyl-4-((2-fluorobenzyl)oxy)benzamido)methyl)benzoic add,
4-((N-(Cyclopropylmethyl)-2-fluoro-4-(2-fluorophenoxy)-benzamido)methyl)benzoic add,
4-((N-Benzyl-4-(2-fluorophenoxy)cyclohexanecarboxamido)-methyl)benzoic acid,
trans-4-((N-Benzyl-4-(2-methoxyphenoxy)cyclohexanecarboxamido)-methyl)benzoic acid,
cis-4-((N-(3-(3-Fluorophenyl)propyl)-4-(2-methoxyphenoxy)cyclohexanecarboxamido)methyl)benzoic acid,
trans-4-((N-(3-(3-Fluorophenyl)propyl)-4-(2-methoxyphenoxy)cyclohexanecarboxamido)methyl)benzoic acid
2-Fluoro-4-((4-(2-fluorophenoxy)-N-(3-methoxybenzyl)benzamido)-methyl)benzoic acid,
4-((4-(2-Fluorophenoxy)-N-propylbenzamido)methyl)benzoic acid,
4-((4-(2-Methoxyphenoxy)-N-(2,2,2-trifluoroethyl)benzamido)methyl)benzoic acid,
4-((4-(2-methoxyphenoxy)-N-propylbenzamido)methyl)benzoic acid,
4-((N-(2,2-difluoropropyl)-4-(2-methoxyphenoxy)-benzamido)methyl)benzoic acid,
4-((4-(2-methoxyphenoxy)-N-(3,3,3-trifluoropropyl)-benzamido)methyl)benzoic acid,
4-((N-butyl-4-(2-methoxyphenoxy)benzamido)methyl)benzoic acid, 4-((N-(cyclopropylmethyl)-2-fluoro-4-(2-methoxyphenoxy)-benzamido)methyl)benzoic acid,
4-((N-(cyclopropylmethyl)-4-(2-fluoro-6-methoxyphenoxy)-benzamido)methyl)benzoic acid,
4-((N-(cyclopropylmethyl)-4-(4-fluoro-2-methoxyphenoxy)-benzamido)methyl)benzoic acid,
4-((N-(cyclopropylmethyl)-5-(2-methoxyphenoxy)-picolinamido)methyl)benzoic acid,
4-((4-(o-Tolyloxy)-N-(2,2,2-trifluoroethyl)benzamido)methyl)benzoic acid,
4-((4-(2-Fluorophenoxy)-N-(3,3,3-trifluoropropyl)benzamido)methyl)benzoic acid,
4-((4-(2-Chlorophenoxy)-N-(2,2,2-trifluoroethyl)benzamido)methyl)benzoic add,
4-((N-Ethyl-4-(o-tolyloxy)benzamido)methyl)benzoic add,
4-((N-(2,2-Difluoropropyl)-4-(2-fluorophenoxy)benzamido)methyl)benzoic add,
4-((N-Butyl-4-(2-fluorophenoxy)benzamido)methyl)benzoic acid,
4-((4-(2-Chlorophenoxy)-N-ethylbenzamido)methyl)benzoic add,
4-((N-(Cyclopropylmethyl)-5-(2-fluorophenoxy)picolinamido)methyl)benzoic add,
4-((4-(2-Chlorophenoxy)-N-(2,2-difluoroethyl)benzamido)methyl)benzoic add,
4-((N-(Cyclopropylmethyl)-4-(5-fluoro-2-methoxyphenoxy)benzamido)methyl)benzoic add,
4-((4-(4-Fluoro-2-methoxyphenoxy)-N-propylbenzamido)methyl)benzoic add,
4-((4-(5-Fluoro-2-methoxyphenoxy)-N-propylbenzamido)methyl)benzoic add,
4-((N-(Cyclopropylmethyl)-4-(3-fluoro-2-methoxyphenoxy)benzamido)methyl)benzoic add,
4-((N-(Cyclopropylmethyl)-5-(2-fluorophenoxy)pyrimidine-2-carboxamido)methyl)benzoic add,
4-((N-(Cyclopropylmethyl)-5-(2-methoxyphenoxy)pyrimidine-2-carboxamido)methyl)benzoic add, or
4-((5-(2-Methoxyphenoxy)-N-propylpyrimidine-2-carboxamido)methyl)benzoic add,
or a pharmaceutically acceptable salt thereof.

14. A process for preparing the compound according to claim 1, comprising hydrolysing a compound of formula (II) in the presence of a base:

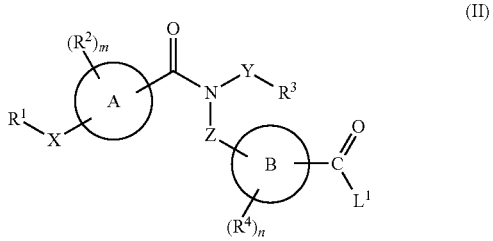

(II)

wherein $L^1$ is an alkoxy group;
and optionally thereafter carrying out at least one of the following procedures:
removing any protecting groups; or
forming a pharmaceutically acceptable salt.

15. A pharmaceutical composition comprising the compound according to claim 1 and a pharmaceutically acceptable adjuvant, diluent, or carrier.

16. A method of treating a patient suffering from a condition whose development or symptoms are linked to LPAR5 activity comprising administering to the patient a pharmaceutically effective amount of the compound according to claim 1,
wherein the condition is chosen from fibrosis, liver diseases, atherosclerosis, inflammatory diseases, gastrointestinal tract diseases, and pain disorders.

17. A method of treating a patient suffering from a condition whose development or symptoms are linked to LPAR1 activity comprising administering to the patient a pharmaceutically effective amount of the compound according to claim 1,
wherein the condition is chosen from fibrosis, liver diseases, atherosclerosis, inflammatory diseases, gastrointestinal tract diseases, and pain disorders.

18. A method of treating a patient suffering from a condition chosen from pain disorders, atherosclerosis or fibrosis comprising administering to the patient a pharmaceutically effective amount of the compound according to claim 1.

19. The compound according to claim 7, wherein $R^3$ represents a saturated or unsaturated 3- to 6-membered carbocyclic ring unsubstituted or substituted by at least one substituent chosen from fluorine, chlorine, hydroxyl, $C_3$-$C_6$ cycloalkyl, $C_1$-$C_2$ alkoxy, phenoxy, benzyloxy, trifluoromethyl, $C_1$-$C_2$ alkyl, or a saturated or unsaturated 3- to 6-membered carbocyclic or heterocyclic ring comprising at least one heteroatom chosen from nitrogen, oxygen, or sulphur, wherein the carbocyclic or heterocyclic ring is unsubstituted or substituted by least one substituent chosen from halogen, $C_1$-$C_2$ alkyl, or $C_1$-$C_2$ alkoxy.

20. The compound according to claim 1, wherein A and B are each independently chosen from cyclopentyl, cyclohexyl, cyclopentenyl, cyclohexenyl, phenyl, pyrrolidinyl, piperidinyl, piperazinyl, morpholinyl, thiomorpholinyl, oxadiazolyl, tetrahydrofuranyl, naphthyl, benzofuranyl, benzothienyl, benzodioxolyl, benzoxazolyl, quinolinyl, oxazolyl, 1,2,3-thiadiazolyl, 2,3-dihydrobenzofuranyl, tetrahydropyranyl, pyrazolyl, imidazo[1,2-a]pyridinyl, pyrazinyl, thiazolidinyl, indanyl, thienyl, isoxazolyl, pyridazinyl, pyrrolyl, furanyl, thiazolyl, isothiazolyl, indolyl, isoindolyl, imidazolyl, pyrimidinyl, benzimidazolyl, triazolyl, tetrazolyl, or pyridinyl.

21. A pharmaceutical composition comprising the compound according to claim 1 and a pharmaceutically acceptable adjuvant, diluent, or carrier, and at least one other therapeutic agent.

22. The compound 4-((N-(cyclopropylmethyl)-4-(2-fluorophenoxy)benzamido)methyl)benzoic acid.

23. The compound 4-((N-(cyclopropylmethyl)-4-(2-fluorophenoxy)benzamido)methyl)benzoic acid or a pharmaceutically acceptable salt thereof.

24. The compound 4-((N-(cyclopropylmethyl)-4-(2-methoxyphenoxy)benzamido)methyl)benzoic acid.

25. The compound 4-((N-(cyclopropylmethyl)-4-(2-methoxyphenoxy)benzamido)methyl)benzoic acid or a pharmaceutically acceptable salt thereof.

* * * * *

UNITED STATES PATENT AND TRADEMARK OFFICE
CERTIFICATE OF CORRECTION

PATENT NO. : 9,464,060 B2  
APPLICATION NO. : 14/463780  
DATED : October 11, 2016  
INVENTOR(S) : William Buffham et al.

Page 1 of 2

It is certified that error appears in the above-identified patent and that said Letters Patent is hereby corrected as shown below:

In the Specification

Column 12, Line 6, "(xiii)cyclobutylmethyl" should read as --(xiii) cyclobutylmethyl--.

Column 12, Line 12, "(xix)benzyl" should read as --(xix) benzyl--.

In the Claims

Claim 13, Column 108, Line 36, "add," should read as --acid,--.

Claim 13, Column 108, Line 38, "add," should read as --acid,--.

Claim 13, Column 108, Line 40, "add," should read as --acid,--.

Claim 13, Column 108, Line 42, "add," should read as --acid,--.

Claim 13, Column 108, Line 44, "add," should read as --acid,--.

Claim 13, Column 109, Line 14, "add," should read as --acid,--.

Claim 13, Column 109, Line 16, "add," should read as --acid,--.

Claim 13, Column 109, Line 18, "add," should read as --acid,--.

Claim 13, Column 109, Line 22, "add," should read as --acid,--.

Claim 13, Column 109, Line 24, "add," should read as --acid,--.

Claim 13, Column 109, Line 26, "add," should read as --acid,--.

Signed and Sealed this  
Third Day of January, 2017

Michelle K. Lee  
*Director of the United States Patent and Trademark Office*

CERTIFICATE OF CORRECTION (continued)
U.S. Pat. No. 9,464,060 B2

Claim 13, Column 109, Line 28, "add," should read as --acid,--.

Claim 13, Column 109, Line 30, "add," should read as --acid,--.

Claim 13, Column 109, Line 32, "add," should read as --acid,--.

Claim 13, Column 109, Line 34, "add," should read as --acid,--.

Claim 13, Column 109, Line 36, "add," should read as --acid,--.

Claim 13, Column 109, Line 38, "add," should read as --acid,--.

Claim 13, Column 109, Line 40, "add," should read as --acid,--.